(12) United States Patent
Kassis

(10) Patent No.: US 11,001,894 B2
(45) Date of Patent: *May 11, 2021

(54) METHODS OF DETECTING SIGNATURES OF DISEASE OR CONDITIONS IN BODILY FLUIDS

(71) Applicant: President and Fellows of Harvard College, Cambridge, MA (US)

(72) Inventor: Amin I. Kassis, Chestnut Hill, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 135 days.

This patent is subject to a terminal disclaimer.

(21) Appl. No.: 15/617,577

(22) Filed: Jun. 8, 2017

(65) Prior Publication Data
US 2018/0119226 A1    May 3, 2018

Related U.S. Application Data

(60) Continuation of application No. 15/338,786, filed on Oct. 31, 2016, which is a continuation of application No. 15/069,173, filed on Mar. 14, 2016, now abandoned, which is a continuation of application No. 14/812,315, filed on Jul. 29, 2015, now abandoned, which is a continuation of application No. 13/349,670, filed on Jan. 13, 2012, now abandoned, which is a division of application No. 12/836,191, filed on Jul. 14, 2010, now abandoned, which is a continuation of application No. PCT/US2009/031395, filed on Jan. 19, 2009.

(60) Provisional application No. 61/073,434, filed on Jun. 18, 2008, provisional application No. 61/022,033, filed on Jan. 18, 2008.

(51) Int. Cl.
| *C12Q 1/68* | (2018.01) |
| *C12Q 1/6886* | (2018.01) |
| *G01N 33/50* | (2006.01) |
| *G01N 33/569* | (2006.01) |
| *G01N 33/574* | (2006.01) |
| *C12Q 1/6883* | (2018.01) |

(52) U.S. Cl.
CPC ......... *C12Q 1/6886* (2013.01); *C12Q 1/6883* (2013.01); *G01N 33/505* (2013.01); *G01N 33/5023* (2013.01); *G01N 33/5047* (2013.01); *G01N 33/5052* (2013.01); *G01N 33/5055* (2013.01); *G01N 33/5091* (2013.01); *G01N 33/569* (2013.01); *G01N 33/57407* (2013.01); *G01N 33/57434* (2013.01); *G01N 33/57449* (2013.01); *G01N 33/57484* (2013.01); *C12Q 2600/106* (2013.01); *C12Q 2600/156* (2013.01); *C12Q 2600/158* (2013.01); *G01N 2570/00* (2013.01)

(58) Field of Classification Search
None
See application file for complete search history.

(56) References Cited

U.S. PATENT DOCUMENTS

| 4,683,195 A | 7/1987 | Mullis et al. |
| 4,683,202 A | 7/1987 | Mullis |
| 4,814,434 A | 3/1989 | Goldfarb |
| 4,843,155 A | 6/1989 | Chomczynski |
| 4,868,103 A | 9/1989 | Stavrianopoulos et al. |
| 5,043,267 A | 8/1991 | Richards |
| 5,077,216 A | 12/1991 | Morganelli et al. |
| 5,459,039 A | 10/1995 | Modrich et al. |
| 5,498,531 A | 3/1996 | Jarrell |
| 5,514,598 A | 5/1996 | Doody |
| 5,594,637 A | 1/1997 | Eisenberg et al. |
| 5,631,169 A | 5/1997 | Lakowicz et al. |
| 5,854,033 A | 12/1998 | Lizardi |
| 6,117,985 A | 9/2000 | Thomas et al. |
| 6,172,198 B1 | 1/2001 | Sinosich |
| 6,258,540 B1 | 7/2001 | Lo et al. |
| 6,631,330 B1 | 10/2003 | Poynard |
| 6,660,477 B2 | 12/2003 | Kluwe |
| 6,664,056 B2 | 12/2003 | Lo et al. |

(Continued)

FOREIGN PATENT DOCUMENTS

| CN | 1668922 A | 9/2005 |
| EP | 2161577 A1 | 3/2010 |

(Continued)

OTHER PUBLICATIONS

Palmer et al. 2006. BMC Genomics. 7:115, fifteen pages 2006. (Year: 2006).*

(Continued)

*Primary Examiner* — Juliet C Switzer

(74) *Attorney, Agent, or Firm* — Nixon Peabody LLP; David S. Resnick; Nicole D. Kling

(57) ABSTRACT

Methods and compositions for diagnosing the presence of a cancer cell in an individual are provided. Methods and compositions for identifying a tumor-specific signature in an individual having cancer are also provided. Methods and compositions for diagnosing the presence of an infectious agent in an individual and/or for identifying an infectious agent-specific signature in an infected individual are provided. Methods and compositions for diagnosing the presence of a disease in an individual are also provided. Methods and compositions for identifying a disease-specific signature in an individual having the disease are also provided.

10 Claims, 19 Drawing Sheets

(56) References Cited

U.S. PATENT DOCUMENTS

| | | |
|---|---|---|
| 6,867,236 B1 | 3/2005 | Breitner et al. |
| 6,986,995 B2 | 1/2006 | Rose et al. |
| 7,009,038 B2 | 3/2006 | Depre et al. |
| 7,157,235 B2 | 1/2007 | Breit et al. |
| 7,235,359 B2 | 6/2007 | Lo et al. |
| 7,294,465 B2 | 11/2007 | Somlo et al. |
| 7,432,107 B2 | 10/2008 | Spanuth |
| 7,445,886 B2 | 11/2008 | Giroir et al. |
| 7,459,280 B2 | 12/2008 | Wang et al. |
| 7,488,584 B2 | 2/2009 | Wang et al. |
| 7,604,948 B2 | 10/2009 | Amaral et al. |
| 7,645,576 B2 | 1/2010 | Lo et al. |
| 7,651,838 B2 | 1/2010 | Paterlini-Brechot |
| 7,655,399 B2 | 2/2010 | Cantor et al. |
| 7,662,578 B2 | 2/2010 | Devarajan |
| 7,670,764 B2 | 3/2010 | Oh et al. |
| 7,670,769 B2 | 3/2010 | Lee |
| 7,723,117 B2 | 5/2010 | Delacourte et al. |
| 2001/0051341 A1 | 12/2001 | Lo et al. |
| 2001/0051344 A1 | 12/2001 | Shalon et al. |
| 2002/0045176 A1 | 4/2002 | Lo et al. |
| 2002/0119118 A1 | 8/2002 | Fong et al. |
| 2002/0192642 A1 | 12/2002 | Lo et al. |
| 2003/0064380 A1 | 4/2003 | Rao et al. |
| 2004/0009518 A1 | 1/2004 | Lo et al. |
| 2004/0038201 A1 | 2/2004 | Nau et al. |
| 2004/0086864 A1 | 5/2004 | Lo et al. |
| 2004/0137452 A1 | 7/2004 | Levett et al. |
| 2004/0203037 A1 | 10/2004 | Lo et al. |
| 2004/0265932 A1 | 12/2004 | Henslee et al. |
| 2005/0130245 A1 | 6/2005 | Houle et al. |
| 2005/0148023 A1 | 7/2005 | Thadhani et al. |
| 2005/0164233 A1 | 7/2005 | Byrne et al. |
| 2005/0164241 A1 | 7/2005 | Hahn et al. |
| 2005/0181386 A1 | 8/2005 | Diamond et al. |
| 2005/0266432 A1 | 12/2005 | Oliphant et al. |
| 2005/0282185 A1 | 12/2005 | Lo Yuk-Ming et al. |
| 2006/0019278 A1 | 1/2006 | Lo et al. |
| 2006/0051873 A1 | 3/2006 | FitzGerald |
| 2006/0088836 A1 | 4/2006 | Wohlgemuth et al. |
| 2006/0094067 A1 | 5/2006 | Herwig |
| 2006/0115832 A1 | 6/2006 | Hoon |
| 2006/0115854 A1 | 6/2006 | Goldknopf et al. |
| 2006/0115855 A1 | 6/2006 | Goldknopf et al. |
| 2006/0166283 A1 | 7/2006 | Delacourte et al. |
| 2006/0172429 A1 | 8/2006 | Nilsson et al. |
| 2006/0210562 A1 | 9/2006 | Zaghouani et al. |
| 2006/0234301 A1 | 10/2006 | Dotan et al. |
| 2006/0252068 A1 | 11/2006 | Lo et al. |
| 2006/0252071 A1 | 11/2006 | Lo et al. |
| 2006/0257901 A1 | 11/2006 | Karumanchi |
| 2006/0259990 A1 | 11/2006 | Von Der Kammer et al. |
| 2006/0259991 A1 | 11/2006 | Von Der Kammer et al. |
| 2007/0015172 A1 | 1/2007 | Zhang et al. |
| 2007/0037179 A1 | 2/2007 | Liboni et al. |
| 2007/0099209 A1 | 5/2007 | Clarke et al. |
| 2007/0134689 A1 | 6/2007 | Chow |
| 2007/0141625 A1 | 6/2007 | Santos et al. |
| 2007/0148661 A1 | 6/2007 | Vance et al. |
| 2007/0162983 A1 | 7/2007 | Hesterkamp et al. |
| 2007/0207466 A1 | 9/2007 | Cantor et al. |
| 2007/0218469 A1 | 9/2007 | Navon |
| 2007/0218519 A1 | 9/2007 | Urdea et al. |
| 2007/0224638 A1 | 9/2007 | Melanitou-McClymont |
| 2007/0264197 A1 | 11/2007 | Lamping et al. |
| 2007/0275402 A1 | 11/2007 | Lo et al. |
| 2008/0026378 A1 | 1/2008 | Bottazzo et al. |
| 2008/0026405 A1 | 1/2008 | Lovell et al. |
| 2008/0038730 A1 | 2/2008 | Von der Kammer et al. |
| 2008/0039402 A1 | 2/2008 | Mossalayi et al. |
| 2008/0051334 A1 | 2/2008 | Pohlner et al. |
| 2008/0057590 A1 | 3/2008 | Urdea et al. |
| 2008/0108509 A1 | 5/2008 | Haupl et al. |
| 2008/0152589 A1 | 6/2008 | Schofield et al. |
| 2008/0153090 A1 | 6/2008 | Lo et al. |
| 2008/0220013 A1 | 9/2008 | Hochstrasser et al. |
| 2008/0227709 A1 | 9/2008 | Pascual et al. |
| 2008/0261226 A1 | 10/2008 | Wang et al. |
| 2008/0269103 A1 | 10/2008 | Von Der Kammer et al. |
| 2008/0274118 A1 | 11/2008 | Aukerman et al. |
| 2008/0286263 A1 | 11/2008 | Leeds et al. |
| 2009/0023166 A1 | 1/2009 | Jeannin et al. |
| 2009/0041862 A1 | 2/2009 | Schofield et al. |
| 2009/0054321 A1 | 2/2009 | O'Neill et al. |
| 2009/0061425 A1 | 3/2009 | Lo et al. |
| 2009/0104605 A1 | 4/2009 | Siuzdak et al. |
| 2009/0110667 A1 | 4/2009 | Mozaffarian et al. |
| 2009/0130683 A1 | 5/2009 | Gaffney et al. |
| 2009/0155230 A1 | 6/2009 | Salonen et al. |
| 2009/0155776 A1 | 6/2009 | Lo et al. |
| 2009/0162842 A1 | 6/2009 | Lo et al. |
| 2009/0170102 A1 | 7/2009 | Lo et al. |
| 2009/0176217 A1 | 7/2009 | Sella-Tavor et al. |
| 2009/0196927 A1 | 8/2009 | Panitch et al. |
| 2009/0202469 A1 | 8/2009 | Maruyama et al. |
| 2009/0239241 A1 | 9/2009 | Ray et al. |
| 2009/0239242 A1 | 9/2009 | Kilty et al. |
| 2009/0258025 A1 | 10/2009 | Godowski et al. |
| 2009/0263474 A1 | 10/2009 | Banchereau et al. |
| 2009/0263796 A1 | 10/2009 | Wohlgemuth et al. |
| 2009/0274709 A1 | 11/2009 | Xu et al. |
| 2009/0275046 A1 | 11/2009 | Goldknopf et al. |
| 2009/0305265 A1 | 12/2009 | Snider et al. |
| 2009/0317797 A1 | 12/2009 | Paterlini et al. |
| 2009/0318354 A1 | 12/2009 | Cahill et al. |
| 2009/0318392 A1 | 12/2009 | Oresic et al. |
| 2009/0324611 A1 | 12/2009 | Eriksson |
| 2010/0009352 A1 | 1/2010 | Gough et al. |
| 2010/0009356 A1 | 1/2010 | Snider et al. |
| 2010/0021929 A1 | 1/2010 | Pow |
| 2010/0028356 A1 | 2/2010 | Schofield et al. |
| 2010/0055722 A1 | 3/2010 | Nayak et al. |
| 2010/0056523 A1 | 3/2010 | Heerding et al. |
| 2010/0062463 A1 | 3/2010 | Bergmann et al. |
| 2010/0068705 A1 | 3/2010 | Helgadottir et al. |
| 2010/0068711 A1 | 3/2010 | Umansky et al. |
| 2010/0075891 A1 | 3/2010 | Ayalon-Soffer et al. |
| 2010/0081142 A1 | 4/2010 | Chen et al. |
| 2010/0092983 A1 | 4/2010 | Liew |
| 2010/0098705 A1 | 4/2010 | Eugen-Olsen et al. |
| 2010/0104579 A1 | 4/2010 | Hubner et al. |
| 2010/0105086 A1 | 4/2010 | Landolfo et al. |
| 2010/0105623 A1 | 4/2010 | Weinberger et al. |
| 2010/0112587 A1 | 5/2010 | Hare et al. |
| 2010/0120041 A1 | 5/2010 | Quaggin |
| 2010/0120050 A1 | 5/2010 | Gadkar et al. |
| 2010/0120056 A1 | 5/2010 | Bar-Or et al. |
| 2010/0120076 A1 | 5/2010 | Braun et al. |
| 2010/0120629 A1 | 5/2010 | Ellis et al. |
| 2010/0124746 A1 | 5/2010 | Liew |
| 2010/0124756 A1 | 5/2010 | Ray et al. |
| 2010/0131286 A1 | 5/2010 | Houlgatte et al. |
| 2010/0137263 A1 | 6/2010 | Smith |
| 2010/0137393 A1 | 6/2010 | Bottazzo et al. |
| 2010/0143951 A1 | 6/2010 | Kronenberg et al. |
| 2010/0159486 A1 | 6/2010 | Liotta et al. |
| 2010/0167320 A1 | 7/2010 | Beernink et al. |
| 2010/0167937 A1 | 7/2010 | Goldknopf et al. |
| 2010/0169988 A1 | 7/2010 | Kohli et al. |
| 2010/0184031 A1 | 7/2010 | Raes et al. |
| 2011/0033839 A1 | 2/2011 | Kassis |
| 2011/0251097 A1 | 10/2011 | Song et al. |
| 2012/0021404 A1 | 1/2012 | Melkonyan et al. |
| 2012/0040846 A1 | 2/2012 | Kassis |
| 2012/0053073 A1 | 3/2012 | Kassis |
| 2018/0258488 A1 | 9/2018 | Kassis |

FOREIGN PATENT DOCUMENTS

| | | |
|---|---|---|
| JP | H11118792 A | 4/1999 |
| JP | H11295304 A | 10/1999 |
| JP | 2005-531785 A | 10/2005 |
| JP | 2007211020 A | 8/2007 |
| KR | 20100044307 A | 4/2010 |

(56) References Cited

FOREIGN PATENT DOCUMENTS

| | | |
|---|---|---|
| WO | 1994/016101 A2 | 7/1994 |
| WO | 0114881 A1 | 3/2001 |
| WO | 2002/028999 A2 | 4/2002 |
| WO | 2002/070748 A2 | 9/2002 |
| WO | 02068685 A2 | 9/2002 |
| WO | 03019193 A1 | 3/2003 |
| WO | 2004/024098 A2 | 3/2004 |
| WO | 2004/040016 A2 | 5/2004 |
| WO | 2004/050704 A1 | 6/2004 |
| WO | 2004/071269 A2 | 8/2004 |
| WO | 2004/076639 A2 | 9/2004 |
| WO | 2004/079012 A1 | 9/2004 |
| WO | 2005/007836 A1 | 1/2005 |
| WO | 2005/012907 A1 | 2/2005 |
| WO | 2005017192 A2 | 2/2005 |
| WO | 2005/020784 A2 | 3/2005 |
| WO | 2005/033341 A2 | 4/2005 |
| WO | 2005/052592 A2 | 6/2005 |
| WO | 2005/095644 A2 | 10/2005 |
| WO | 2005/103712 A2 | 11/2005 |
| WO | 2005/111626 A2 | 11/2005 |
| WO | 2005/114222 A1 | 12/2005 |
| WO | 2006/020269 A2 | 2/2006 |
| WO | 2006/020899 A2 | 2/2006 |
| WO | 2006/026020 A2 | 3/2006 |
| WO | 2006/048778 A1 | 5/2006 |
| WO | 2006/050475 A2 | 5/2006 |
| WO | 2006/061609 A2 | 6/2006 |
| WO | 2006/073941 A2 | 7/2006 |
| WO | 2006/105907 A1 | 10/2006 |
| WO | 2006/114661 A1 | 11/2006 |
| WO | 2006/125117 A2 | 11/2006 |
| WO | 2006/133423 A1 | 12/2006 |
| WO | 2006/134390 A2 | 12/2006 |
| WO | 2007/047907 A2 | 4/2007 |
| WO | 2007/082733 A1 | 7/2007 |
| WO | 2007076411 A1 | 7/2007 |
| WO | 2007/098585 A1 | 9/2007 |
| WO | 2007/112999 A2 | 10/2007 |
| WO | 2007/119179 A2 | 10/2007 |
| WO | 2007/131345 A1 | 11/2007 |
| WO | 2008/003826 A1 | 1/2008 |
| WO | 2008/010660 A1 | 1/2008 |
| WO | 2008/014314 A2 | 1/2008 |
| WO | 2008/014516 A2 | 1/2008 |
| WO | 2008/028257 A1 | 3/2008 |
| WO | 2008/042012 A1 | 4/2008 |
| WO | 2008/043725 A1 | 4/2008 |
| WO | 2008/043782 A2 | 4/2008 |
| WO | 2008/046509 A1 | 4/2008 |
| WO | 2008/046510 A1 | 4/2008 |
| WO | 2008/046511 A1 | 4/2008 |
| WO | 2008/046512 A1 | 4/2008 |
| WO | 2008/063369 A2 | 5/2008 |
| WO | 2008/064336 A2 | 5/2008 |
| WO | 2008/082519 A2 | 7/2008 |
| WO | 2008/084331 A2 | 7/2008 |
| WO | 2008/085035 A1 | 7/2008 |
| WO | 2008/089936 A1 | 7/2008 |
| WO | 2008/095261 A1 | 8/2008 |
| WO | 2008/100596 A2 | 8/2008 |
| WO | 2008/120684 A1 | 10/2008 |
| WO | 2008/125651 A2 | 10/2008 |
| WO | 2008/127317 A2 | 10/2008 |
| WO | 2008/129296 A2 | 10/2008 |
| WO | 2008/132464 A2 | 11/2008 |
| WO | 2008/137835 A2 | 11/2008 |
| WO | 2008/147938 A2 | 12/2008 |
| WO | 2008/154238 A1 | 12/2008 |
| WO | 2008/156867 A1 | 12/2008 |
| WO | 2009/000520 A1 | 12/2008 |
| WO | 2009/001392 A1 | 12/2008 |
| WO | 2009/003142 A1 | 12/2008 |
| WO | 2009/014639 A2 | 1/2009 |
| WO | 2009/017444 A2 | 2/2009 |
| WO | 2009/032722 A1 | 3/2009 |
| WO | 2009/034470 A2 | 3/2009 |
| WO | 2009/043848 A2 | 4/2009 |
| WO | 2009/050444 A1 | 4/2009 |
| WO | 2009/053523 A1 | 4/2009 |
| WO | 2009/053537 A1 | 4/2009 |
| WO | 2009/055487 A1 | 4/2009 |
| WO | 2009/058168 A1 | 5/2009 |
| WO | 2009/059259 A2 | 5/2009 |
| WO | 2009/060035 A1 | 5/2009 |
| WO | 2009/068591 A2 | 6/2009 |
| WO | 2009/074331 A2 | 6/2009 |
| WO | 2009/075566 A1 | 6/2009 |
| WO | 2009/075579 A1 | 6/2009 |
| WO | 2009/080780 A1 | 7/2009 |
| WO | 2009/083950 A2 | 7/2009 |
| WO | 2009/092068 A1 | 7/2009 |
| WO | 2009/092382 A1 | 7/2009 |
| WO | 2009/097450 A1 | 8/2009 |
| WO | 2009/100131 A2 | 8/2009 |
| WO | 2009/100342 A2 | 8/2009 |
| WO | 2009/121152 A2 | 10/2009 |
| WO | 2009/121951 A1 | 10/2009 |
| WO | 2009/122387 A1 | 10/2009 |
| WO | 2009/127644 A2 | 10/2009 |
| WO | 2010/005750 A2 | 1/2010 |
| WO | 2010/011506 A2 | 1/2010 |
| WO | 2010/012306 A1 | 2/2010 |
| WO | 2010/018185 A1 | 2/2010 |
| WO | 2010/019553 A1 | 2/2010 |
| WO | 2010/022210 A2 | 2/2010 |
| WO | 2010/024776 A1 | 3/2010 |
| WO | 2010/025434 A1 | 3/2010 |
| WO | 2010/039714 A1 | 4/2010 |
| WO | 2010/041046 A2 | 4/2010 |
| WO | 2010/046137 A1 | 4/2010 |
| WO | 2010/046503 A2 | 4/2010 |
| WO | 2010/047448 A1 | 4/2010 |
| WO | 2010/048346 A1 | 4/2010 |
| WO | 2010/048347 A2 | 4/2010 |
| WO | 2010/048497 A1 | 4/2010 |
| WO | 2010/053587 A2 | 5/2010 |
| WO | 2010/054167 A2 | 5/2010 |
| WO | 2010/054389 A1 | 5/2010 |
| WO | 2010/059242 A2 | 5/2010 |
| WO | 2010/059996 A1 | 5/2010 |
| WO | 2010/061283 A2 | 6/2010 |
| WO | 2010/063009 A1 | 6/2010 |
| WO | 2010/066000 A1 | 6/2010 |
| WO | 2010/068686 A2 | 6/2010 |
| WO | 2012/012693 A2 | 1/2012 |
| WO | 2012/012694 A2 | 1/2012 |
| WO | 2012/012704 A2 | 1/2012 |
| WO | 2012/012709 A2 | 1/2012 |
| WO | 2012/012714 A2 | 1/2012 |
| WO | 2012/012717 A1 | 1/2012 |
| WO | 2012012725 A2 | 1/2012 |
| WO | 2012/115885 A1 | 8/2012 |

OTHER PUBLICATIONS

Herwig et al. Clinical Prostate Cancer. vol. 3. 184-188 2004 (Year: 2004).*
Lee (Clinical Chemistry, 47:8, 1350-1352 (2001)) (Year: 2001).*
Michiels et al. Lancet, 2005; 365:488-492 (Year: 2005).*
Slonin, Nature Genetics Supplement, vol. 32, Dec. 2002, pp. 502-508 (Year: 2002).*
Baker. Journal of the National Cancer Institute, vol. 95, No. 7, Apr. 2, 2003 (Year: 2003).*
Thisted (1998) What is a P-value? University of Chicago, May 1998. accessed from http://www.stat.uchicago.edu/~thisted (Year: 1998).*
De Visser et al. (Nature Reviews, vol. 6, Jan. 2006, pp. 24-37) (Year: 2006).*
Tang et al. Journal of Cerebral Blood Flow & Metabolism (2006) 26, 1089-1102 (Year: 2006).*
Rennert et al. Journal of Interferon & Cytokine Research 26:820-826 (2006). (Year: 2006).*

(56) References Cited

OTHER PUBLICATIONS

Affymetrix Show Results printout. Search query BAK1 against HG-U133 Plus 2 microarray. obtained from https://www.affymetrix.com/analysis/netaffx/showresults.affx on Nov. 1, 2019. one page. (Year: 2019).*

Affymetrix Show Results printout. Search query EGFR against HG-U133 Plus 2 microarray. obtained from https://www.affymetrix.com/analysis/netaffx/showresults.affx on Nov. 1, 2019. one page. (Year: 2019).*

Affymetrix Show Results printout. Search query ERBB2 against HG-U133 Plus 2 microarray. obtained from https://www.affymetrix.com/analysis/netaffx/showresults.affx on Nov. 1, 2019. two pages. (Year: 2019).*

Ye et al. (Cancer 2007;109:1729-35) (Year: 2007).*

Vernimmen et al. (British Journal of Cancer (2003) 89, 899-906) (Year: 2003).*

Abravaya et al., "Detection of point mutations with a modified ligase chain reaction (Gap-LCR)," Nucleic Acids Res. 23:675-682 (1995).

Allen, Lee-Ann H.,"Modulating Phagocyte Activation: The Pros and Cons of Helicobacter pylori Virulence Factors," Journal of Experimental Medicine, May 1, 2000, pp. 1451-1454, vol. 191, No. 9, The Rockefeller University Press.

Avagyan, et al., "Immune Blood Biomarkers of Alzheimer Disease Patients," Journal of Neuroimmunology, 210 (2009) 67-72.

Baker, Stuart G., "The Central Role of Receiver Operating Characteristic (ROC) Curves in Evaluating Tests for the Early Detection of Cancer," Journal of the National Cancer Institute, vol. 95, No. 7, Apr. 2, 2003.

Balagurumoorthy et al., Genome-subtractive cancer-specific blood assay. Cancer Research. AACR Annual Meeting. Apr. 18-22, 2009. Abstract #2562.

Barany, "Genetic disease detection and DNA amplification using cloned thermostable ligase," Proc. Natl. Acad. Sci. USA 88:189-193 (1991).

Bergsmedh, A., et al. 2006 Molecular Cancer Research 4: 187-195.

Bidwell, Bradley N. et al. Silencing of Irf7 pathways in breast cancer cells promotes bone metastasis through immune escape. Nature Medicine. col. 18, No. 8. Aug. 2012.

Biswas, Subhra K. et al. A distinct and unique transcriptional program expressed by tumor-associated macrophages (defective NF-KB and enhanced IRF-3/STAT1 activation). Blood. Mar. 1, 2006. vol. 101. No. 5.

Bitterman, et al., "Alveolar Macrophage Replication. One Mechanism for the Expansion of the Mononuclear Phagocyte Population in the Chronically Inflamed Lung," The Journal of Clinical Investigations, Inc., vol. 74, Aug. 1984, 460-469.

Caruso, R. A., et al.,2012 Exp Oncol 34: 306-311.

Chakraborty, A., et al., "A Spontaneous Murine Melanoma Lung Metastasis Comprised of Host X Tumor Hybrids," Cancer Research, 60, 2512-2519, May 1, 2000.

Cheung, M., et al., "Prenatal Diagnosis of Sickle Cell Anemia and Thalassaemia By Analysis of Fetal Cells in Maternal Blood," Nature Genetics, vol. 14, Nov. 1996.

Chiu et al., "Noninvasive prenatal diagnosis of fetal chromosomal aneuploidy by massively parallel genomic sequencing of DNA in maternal plasma," Proc Natl Acad Sci USA, 105:20458-20463 (2008).

Cohen et al., "Emerging technologies for sequencing antisense oligonucleotides: capillary electrophoresis and mass spectrometry," Adv. Chromatogr., 36:127-162 (1996).

Colcher, D., et al., "A Spectrum of Monoclonal Antibodies Reactive with Human Mammary Tumor Cells," Proc. Natl. Acad. Sci. USA, vol. 78, No. 5, pp. 3199-3203, May 1981.

Colcher, D., et al., "Prolonged Binding of a Radiolabeled Monoclonal Antibody (B72.3) Used for the in Situ Radioimmunodetection of Human Colon Carcinoma Xenografts," Cancer Research, 44, 5744-5751, Dec. 1984.

Coleman, R.; Of mouse and man—what is the value of the mouse in predicting gene expression in humans?; Drug Discovery Today. 2003. 8: 233-235.

Cotton et al., "Reactivity of cytosine and thymine in single-base-pair mismatches with hydroxylamine and osmium tetroxide and its application to the study of mutations," Proc. Natl. Acad. Sci., 85:4397-4401 (1988).

Cotton, "Current methods of mutation detection," Mutat. Res., 285:125-144 (1993).

Cronin et al., "Cystic fibrosis mutation detection by hybridization to light-generated DNA probe arrays," Human Mutation, 7:244-255 (1996).

Du et al., Genomic profiles for human peripheral blood T cells, B cells, natural killer cells, monocytes, and polymorponuclear cells: Comparisons to ischemic stroke, migrane, and Tourette syndrome, Genomics. 2006. 87: 693-703.

Efron, "Empirical Bayes Estimates for Large-Scale Prediction Problems," J Am Stat Assoc, 104:1015-1028 (2009).

Ehnfors, J., et al., 2009 Cell Death and Differentiation 16: 749-757.

Engels, Eric A., "Infectious Agents as Causes of Non-Hodgkin Lymphoma," Cancer Epidemiol Biomarkets Prev 2007, 16(3), Mar. 2007.

English Translation of Office Action issued for corresponding JP Patent Application No. 2010-543301, dated Aug. 13, 2013.

European Search Report issued from corresponding EP Application No. 11810446.2, dated Nov. 14, 2013.

European Search Report issued from corresponding European Patent Application No. 11810447.0, dated Feb. 18, 2014.

Examination Report issued in corresponding Australian Patent Application No. 2011280997, dated Aug. 14, 2014.

Examination Report issued in corresponding Australian Patent Application No. 2011281007, dated Aug. 7, 2014.

Examination Report issued in corresponding Australian Patent Application No. 2011281012, dated Aug. 7, 2014.

Examination Report issued in corresponding Australian Patent Application No. 2011280936, dated Aug. 7, 2014.

Examination Report issued in corresponding Australian Patent Application No. 2011280944, dated Jul. 26, 2014.

Examination Report issued in corresponding Australian Patent Application No. 2011281017, dated Aug. 7, 2014.

Examination Report issued in corresponding New Zealand Patent Application No. 602007, dated Feb. 26, 2014.

Examination Report issued in corresponding New Zealand Patent Application No. 607305, dated Jul. 2, 2013.

Examination Report issued in corresponding New Zealand Patent Application No. 621533, dated Feb. 26, 2014.

Examination Report issued in corresponding NZ Patent Application No. 703445, dated Jan. 22, 2015.

Examination Report issued in corresponding NZ Patent Application No. 703450, dated Jan. 22, 2015.

Examination Report received in corresponding New Zealand Application No. 711367, dated Sep. 9, 2015.

Examination Report relating to corresponding NZ Patent Application No. 586834, dated Feb. 24, 2011.

Extended European Search Report issued in corresponding European Application No. 11810453.8 dated Feb. 6, 2014.

Extended European Search Report issued in corresponding European Application No. 11810457.9 dated Dec. 4, 2013.

Extended European Search Report issued in corresponding European Application No. 11810461.1 dated Mar. 21, 2014.

Extended European Search Report issued in corresponding European Application No. 11810462.9 dated Dec. 13, 2013.

Extended European Search Report issued in corresponding European Application No. 11810464.5 dated Dec. 13, 2013.

Extended European Search Report relating to corresponding EP Application No. 09703015.9, dated Feb. 6, 2012.

Gasparini et al., "Restriction site generating-polymerase chain reaction (RG-PCR) for the probeless detection of hidden genetic variation: application to the study of some common cystic fibrosis mutations," Mol. Cell Probes, 6:1-7 (1992).

Michiels, et al., "Prediction of Cancer Outcome With Microarrays: A Multiple Random Validation Strategy," Lancet, 2005, 365: 488-492.

(56) References Cited

OTHER PUBLICATIONS

Myers et al., "Detection of single base substitutions by ribonuclease cleavage at mismatches in RNA:DNA duplexes," Science, 230:1242-1246 (1985).
Myers et al., "Detection of single base substitutions in total genomic DNA," Nature, 313:495-498 (1985).
Naeve et al., "Accuracy of automated DNA sequencing: a multi-laboratory comparison of sequencing results," Biotechniques 19:448-453 (1995).
Nakazawa et al., "UV and skin cancer: specific p53 gene mutation in normal skin as a biologically relevant exposure measurement," Proc. Natl. Acad. Sci., 91:360-364 (1994).
Nanni et al.; Differential gene expression profiling in genetic and multifactorial cardiovascular diseases; Journal of Molecular and Cellular Cardiology. 2006. 41 (6): 934-948.
Office Action issued for corresponding AU Patent Application No. 2009205956, dated Sep. 13, 2013.
Office Action issued for corresponding Canadian Patent Application No. 2 ,712, 303, dated Mar. 19, 2013.
Office Action issued for corresponding Chinese Patent Application No. 200980109695.4, dated Mar. 5, 2013.
Office Action issued for corresponding JP Patent Application No. 2010-543301, dated Aug. 13, 2013.
Office Action issued for corresponding New Zealand Patent Application No. 602007 dated Aug. 24, 2012.
Office Action issued for corresponding U.S. Appl. No. 13/188,683, dated Apr. 23, 2013.
Office Action issued for corresponding U.S. Appl. No. 13/188,683, dated Feb. 21, 2014.
Office Action issued for corresponding U.S. Appl. No. 13/188,964 dated Aug. 14, 2012.
Office Action issued for corresponding U.S. Appl. No. 13/188,964, dated Jun. 4, 2013.
Office Action issued for corresponding U.S. Appl. No. 13/349,670, dated Jun. 7, 2013.
Office Action issued in corresponding Chinese Application No. 200980109695.4 dated Jan. 16, 2014.
Office Action issued in corresponding Chinese Application No. 200980109695.4 dated Sep. 29, 2014.
Office Action issued in corresponding Chinese Application No. 201180046173.1 dated Jan. 28, 2014.
Office Action issued in corresponding Chinese Application No. 201180046173.1, dated Jan. 18, 2016.
Office Action issued in corresponding Chinese Application No. 201180046174.6 dated Feb. 8, 2014.
Office Action issued in corresponding Chinese Patent Application No. 2011800461731, dated Dec. 23, 2014.
Office Action issued in corresponding Eurasian Application No. 201390149, dated Feb. 12, 2015.
Office Action issued in corresponding Eurasian Application No. 201390150, dated Mar. 17, 2015.
Office Action issued in corresponding European Application No. 09703015.9 dated Apr. 22, 2014.
Office Action issued in corresponding European Application No. 09703015.9, dated Jul. 6, 2015.
Office Action issued in corresponding European Application No. 11810446.2 dated Jul. 17, 2014.
Office Action issued in corresponding European Application No. 11810447.0, dated Jan. 21, 2016.
Office Action issued in corresponding European Application No. 11810461.1, dated Dec. 15, 2015.
Office Action issued in corresponding European Application No. 11810457.9, dated Feb. 12, 2015.
Office Action issued in corresponding IL Application No. 224321, dated Nov. 26, 2015.
Office Action issued in corresponding Israeli Application No. 207027 dated Jul. 23, 2014.
Office Action issued in corresponding Israeli Patent Application No. 224321, dated Dec. 28, 2014.
Office Action issued in corresponding Japanese Application No. 2013-521843, dated Sep. 8, 2015.
Office Action issued in corresponding Japanese Patent Application No. 2010-543301, dated Jul. 8, 2014.
Office Action issued in corresponding Japanese Patent Application No. 2014-025368, dated Jan. 27, 2015.
Office Action issued in corresponding Korean Application No. 10-2010-7018216, dated Mar. 7, 2016.
Office Action issued in corresponding Mexican Application No. Mx/A/2013/000917, dated Oct. 13, 2015.
Office Action issued in corresponding Mexican Patent Application No. Mx/a/2010/007822, dated Feb. 4, 2014.
Office Action issued in corresponding Mexican Patent Application No. Mx/a/2010/007822, dated Oct. 14, 2014.
Office Action issued in corresponding New Zealand Patent Application No. 607304, dated Jul. 2, 2013.
Office Action issued in corresponding U.S. Appl. No. 12/836,191, dated Dec. 5, 2014.
Office Action issued in corresponding U.S. Appl. No. 13/188,683, dated Feb. 21, 2014.
Office Action issued in corresponding U.S. Appl. No. 13/188,964, dated Jul. 2, 2014.
Office Action issued in corresponding U.S. Appl. No. 13/349,670, dated Jul. 2, 2014.
Office Action issued in corresponding U.S. Appl. No. 13/836,191, dated May 8, 2014.
Office Action received in corresponding Chinese Application 201180046174.6, dated Apr. 17, 2015.
Office Action received in corresponding European Application 11810453.8, dated Apr. 29, 2015.
Office Action received in corresponding Mexican Application No. Mx/A/2010/007822 dated Jun. 26, 2015.
Gautier, L., et al., "Affy-Analysis of Affymetirix GeneChip Data at the Probe Level," Bioinformatics, vol. 20, No. 3, 2004, pp. 307-315.
Gibbs et al., "Detection of single DNA base differences by competitive oligonucleotide priming," Nucl. Acids Res., 17:2437-2438 (1989).
Ginos, M., et al., "Identification of a Gene Expression Signature Associate with Recurrent Disease in Squamous Cell Carcinoma of the Head and Neck," Cancer Research, 64, 55-63, Jan. 1, 2004.
Griffin et al., "DNA sequencing. Recent innovations and future trends," Appl. Biochem. Biotechnol., 38:147-159 (1993).
Grigoriadis, et al., "Establishment of the Epithelial-Specific Transcriptome of Normal and Malignant Human Breast Cells Based on MPSS and Array Expression Data," Breast Cancer Research, vol. 8, No. 5, 1-15, 2006.
Guatelli et al., "Isothermal, in vitro amplification of nucleic acids by a multienzyme reaction modeled after retroviral replication," Proc. Natl. Acad. Sci. USA 87:1874-1878 (1990).
Guha, K.D., Scientisti Develope Novel Cancer Blood Test, The Harvard Crimson. Apr. 28, 2009, available via url: <thecrimson. com/article/2009/4/28/scientists-develop-novelcancer-blood-test!>.
Haakenson, Joshua et al. HDAC6 and Ovarian Cancer. Int. J. Mol. Sci. 2013, 14, 9514-9535.
Hage et al., "Recent advances in chromatographic and electrophoretic methods for the study of drug-protein interactions," J. Chromatogr. B. Biomed. Sci. Appl., 12:499-525 (1997).
Haupl et al.; Reactivation of Rheumatoid Arthritis After Pregnancy; Arthritis and Rheumatism. 2008. 58(10): 2981-2992.
Hayashi, "PCR-SSCP: a method for detection of mutations," Genet. Anal. Tech. Appl., 9:73-79 (1992).
Heegaard, "Capillary electrophoresis for the study of affinity interactions," J. Mol. Recognit., 11 :141-148 (1998).
Herwig, R., et al., "Ability of PSA-Positive Circulating Macrophages to Detect Prostate Cancer," The Prostate 62:290-298, 2005.
Herwig, R., et al., "Measurement of Intracellular Versus Extracellular Prostate-Specific Antigen Levels in Peripheral Macrophages: A New Approach to Noninvasive Diagnosis of Prostate Cancer," Clinical Prostate Cancer, vol. 3, No. 3, 184-188, 2004.
Holmgren, L., et al., "Horizontal Transfer of DNA by the Uptake of Apoptotic Bodies," Blood, vol. 93, No. 11 Jun. 1, 1999, pp. 3956-3963.

(56) References Cited

OTHER PUBLICATIONS

Hoshikawa et al.; Hypoxia induces different genes in the lungs of rats compared with mice; Physical Genomics 2003 vol. 12 pp. 209-219.
Hsu et al., "Detection of DNA point mutations with DNA mismatch repair enzymes," Carcinogenesis, 15:1657-1662 (1994).
Huber, W., et al., Variance Stabilization Applied to Microarray Data Calibration and to the Quantification of Differential Expression, Bioinformatics, vol. 18, Suppl. 1, 2002 S96-S104.
International Search Report and Written Opinion relating to corresponding PCT/US20 11/044973, dated Mar. 13, 2012.
International Search Report and Written Opinion relating to corresponding PCT/US2009/031395, dated Mar. 30, 2009.
International Search Report and Written Opinion relating to corresponding PCT/US2011/044969, dated Mar. 23, 2012.
International Search Report and Written Opinion relating to corresponding PCT/US2011/044991, dated Mar. 16, 2012.
International Search Report and Written Opinion relating to corresponding PCT/US2011/044996, dated Mar. 14, 2012.
International Search Report and Written Opinion relating to corresponding PCT/US2011/0450002, dated Mar. 15, 2012.
International Search Report and Written Opinion relating to corresponding PCT/US2011/045009, dated Dec. 14, 2011.
International Search Report and Written Opinion relating to corresponding PCT/US2011/045018, dated Mar. 6, 2012.
Kang et al., "Adenoviral gene transfer of Caenorhabditis elegans n-3 fatty acid desaturase optimizes fatty acid composition in mammalian cells," Proc. Natl. Acad. Sci., 98:4050-4054 (2001).
Kang et al., "Essential fatty acid metabolism in cultured human airway epithelial cells," Biochim. Biophys. Acta., 1128:267-274 (1992).
Kassis, A., et al., "Antibody-Dependant Signal Amplification in Tumor Xenografts after Pretreatment with Biotinylated Monoclonal Antibody and Avidin or Streptavidin," J. Nucl. Med. 1996, 37:343-352.
Keen et al., "Rapid detection of single base mismatches as heteroduplexes on Hydrolink gels," Trends Genet., 7:5 (1991).
Kozal et al., "Extensive polymorphisms observed in HIV-1 clade B protease gene using high-density oligonucleotide arrays," Nature Medicine, 2:753-759 (1996).
Kravtsov, A., et al., "Flow Cytofluorometric Assay of Human Whole Blood Leukocyte DNA Degradation in Response to Yersinia Pestis and *Staphylococcus aureus*." Abstract.
Kravtsov, A., et al., "Flow Cytofluorometric Assay of Human Whole Blood Leukocyte DNA Degradation in Response to Yersinia Pestis and *Staphylococcus aureus*." Proceedings of SPIE, 4241:260-267 (2001).
Kwoh et al., "Transcription-based amplification system and detection of amplified human immunodeficiency virus type 1 with a bead-based sandwich hybridization format," Proc. Natl. Acad. Sci.,86:1173-1177 (1989).
Landegran et al., "A ligase-mediated gene detection technique," Science 241:1077-1080 (1988).
Lau, Sean K. et al. A Specific Marker of Macrophages in Paraffin-Embedded Tissue Samples. Am J Clin Pathol 2004; 122:794-801.
Lee, Jae K., "Analysis Issues for Gene Expression Array Data," Clinical Chemistry, 47:8, 1350-1352 (2001).
Li et al., "Replacing PCR with COLD-PCR enriches variant DNA sequences and redefines the sensitivity of genetic testing," Nat. Med. 14:579-584 (2008).
Lin M., et al., "Decreased Expression of Cellular Prostatic Acid Phosphatase Increases Tumorigenicity of Human Prostate Cancer Cells," The Journal of Urology, vol. 166, 1943-1950, Nov. 2001.
Linehan et al.; The Genetics Basis of Cancer of the Kidney; The Jouranl of Urology vol. 170 2163-2172 Dec. 2003.
Liotta, L., et al., "Cancer's Deadly Signature," Nature Genetics, vol. 33, Jan. 2003.
Liu et al.; Comparison of differentially expressed genes in T lymphocytes between human autoimmune disease and murine models of autoimmune disease; Clinical Immunology. 2004. 112: 225-230.
Liu, Edison T., "Mechanism-Derived Gene Expression Signatures and Predictive Biomarkers in Clinical Oncology," PNAS, Mar. 8, 2005, vol. 102, No. 10, 3531-3532.
Lizardi et al. "Exponential amplification of recombinant-RNA hybridization probes," Bio/Technology 6:1197-1202 (1988).
Lobenhofer, E., et al., "Progress in the Application of DNA Microarrays," Environmental Health Perspectives, vol. 109, No. 9, Sep. 2001.
Loring et al.; A Gene Expression Profile of Alzheimer's Disease; (DNA and Cell Biology vol. 20 No. 11 pp. 683-695 2001).
Lu et al. "MicroRNA expression profiles classify human cancers", Nature vol. 435, Jun. 9, 2005. 834-838. DOI: 10.1038/nature03702.
Maxam et al., "A new method for sequencing DNA," Proc. Natl. Acad. Sci., 74:560-564 (1977).
McLaren, et al., "Antigen-Specific Gene Expression Profiles of Peripheral Blood Mononuclear Cells Do Not Reflect Those of T-Lymphocyte Subsets," Clinical and Diagnostic Laboratory Immunology, Sep. 2004, vol. 11, No. 5, 977-982.
McLerran, D., et al., "Analytical Validation of Serum Proteomic Profiling for Diagnosis of Prostate Cancer: Sources of Sample Bias," Clinical Chemistry, 54:1, 44-52, 2008.
Zimmet et al: "Polyploidy: occurrence in nature, mechanisms, and significance for the megakaryocyte-platelet system", Experimental hematology, Jan. 1, 2000 (Jan. 1, 2000 ), pp. 3-16, XP055185388, Netherlands DOI: 10.1 016/S0301-472X(99)00124-1 Retrieved from the Internet: URL:http://www.ncbi.nlm.nih.gov/pubmed/1 0658672.
Office Action received in corresponding South Korean Application 10-2010-7018216, dated Jun. 10, 2015.
Office Action received in corresponding Taiwanese Application 100126110, dated Apr. 24, 2015.
Office Action received in corresponding U.S. Appl. No. 13/811,682 dated Jul. 31, 2015.
Office Action received in corresponding U.S. Appl. No. 13/811,695 dated Aug. 3, 2015.
Office Action received in corresponding U.S. Appl. No. 13/811,701 dated Aug. 10, 2015.
Office Action received in corresponding U.S. Appl. No. 13/811,705 dated Aug. 10, 2015.
Office Action received in corresponding U.S. Appl. No. 13/811,706 dated Aug. 3, 2015.
Office Action relating to corresponding CA Application No. 2,712,303, dated Apr. 24, 2012.
Orita et al., "Detection polymorphisms of human DNA by gel electrophoresis as single-strand conformation polymorphisms," Proc. Natl. Acad. Sci., 86:2766-2771 (1989).
Palmer, et al., "Cell-Type Specific Gene Expression Profiles of Leukocytes in Human Peripheral Blood," BMC Genomics, 2006,7:115.
Perou, C., et al., "Molecular Portraits of Human Breast Tumors," Nature, vol. 406, Aug. 17, 2000.
Powell, A. Harvard gazette. Apr. 20, 2009, available via url: news.harvard.edu/gazette/story/2009/04/hms-professor-devises-single- test-for-cancers/>.
Prodromou et al., Recursive PCR: a novel technique for total gene synthesis, Protein Eng. 5:827-829(1992).
Prossner, "Detecting single-base mutations," Tibtech, 11:238-246 (1993).
Ransohoff, David F., "Bias as a Threat to the Validity of Cancer Molecular-Marker Research," Nature, vol. 5, Feb. 2005, 142-149.
Rivas et al., New developments in the study of biomolecular associations via sedimentation equilibrium, Trends Biochem. Sci., 18:284-287 (1993).
Rogler, G. et al. Isolation and phenotypic characterization of colonic macrophages. Clin Exp Immunol 1998; 112:205-215.
Rosenbaum et al. "Temperature-gradient gel electrophoresis. Thermodynamic analysis of nucleic acids and proteins in purified form and in cellular extracts". Biophys. Chem. 26, Elsevier 235-246 (1987).

(56) References Cited

OTHER PUBLICATIONS

Saiki et al., "Analysis of enzymatically amplified beta-globin and HLA-DQ alpha DNA with allele-specific oligonucleotide probes," Nature, 324:163-166 (1986).
Saiki et al., "Genetic analysis of amplified DNA with immobilized sequence-specific oligonucleotide probes," Proc. Natl. Acad. Sci. ,86:6230-6234 (1989).
Saleeba et al., "Chemical cleavage of mismatch to detect mutations," Methods Enzymol., 217:286-295 (1992).
Sanger et al., "DNA sequencing with chain-terminating inhibitors," Proc. Natl. Acad. Sci., 74:5463-5467 (1977).
Schiller et al., "Lipid analysis by matrix-assisted laser desorption and ionization mass spectrometry: A methodological approach," Anal. Biochem., 267:46-56 (1999).
Schiller et al., "Matrix-assisted laser desorption and ionization time-of-flight (MALDI-TOF) mass spectrometry in lipid and phospholipid research," Progress in Lipid Research, 43:449-488.
Search Report and Written Opinion issued in corresponding Singapore Application No. 201300215-9, dated Nov. 17, 2015.
Search Report issued in corresponding Chinese Application No. 201180046174.6 dated Jan. 22, 2014.
Search Report issued in corresponding Eurasian Application No. 201390150 dated Jun. 20, 2013.
Segelmark, et al., "Autoimmune Kidney Diseases," Autoimmunity Reviews, 9 (2010) A366-A371.
Sehnert et al., "Optimal detection of fetal chromosomal abnormalities by massively parallel DNA sequencing of cell-free fetal DNA from maternal blood," Clin Chem., 57:1042-1049 (2011).
Seo, J., et al., "Probe Set Algorithms: Is There a Rational Best Bet?" BMC Bioinformatics, 2006, 7:395.
Simpson et al. "Proteomic profiling of exosomes: Current perspectives", Proteomics 2008, 8, 4093-4099.
Sjolander et al., Integrated fluid handling system for biomolecular interaction analysis, Anal. Chem. 63:2338-2345 (1991).
Slonin, Donna K., "From Patterns to Pathways: Gene Expression Data Analysis Comes of Age," Nature Genetics Supplement, vol. 32, Dec. 2002.
Srivastava et al., The Inflammatory versus Constitutive Trafficking of Mononuclear Phagocytes into the Alveolar Space of Mice is Associated with Drastic Changes in Their Gene Expression Profiles; J Immunology. 2005. 175: 1884-1893.
Szabo et al., "Surface plasmon resonance and its use in biomolecular interaction analysis (BIA)," Curr. Opin. Struct. Biol., 5:699-705 (1995).
Takahashi et al.; Gene expression profiling of clear cell renal cell carcinoma: Gene Identification and prognostic classificatio; PNAS vol. 98 No. 17 pp. 9754-9759 Aug. 14, 2001.
Taylor, Marcia L. et al. Flow Cytometric Analysis of Blood Monocytes and Alveolar Macrophages. Methods in Molecular Medicine, vol. 44: Asthma: Mechanisms and Protocols.
Thisted (1998) What is a P-Value. University of Chicago. May 25, 1998. accessed from http://www.stat.uchicago.edu/-thisted.six pages.
Tsuang et al.; Assessing the Validity of Blood-Based Gene Expression Profiles for the Classification of Schizophrenia and Bipolar Disorder: A Preliminary Report; American Journal of Medical Genetics Part B (Neuropsychiatic Genetics) 1338:1 2005).
Van't Veer, L., et al, "Expression Profiling Predicts Outcome in Breast Cancer," Breast Cancer Res., 20003, 5:57-58.
Wachsman et al., "Noninvasive genomic detection of melanoma," Br J Dermatol., 164:797-806 (2011).
Webb, T. 2002 J Natl Cancer Inst 94:413-414.
West, et al., "Embracing the Complexity of Genomic Data for Personalized Medicine," Genome Research, 16:559-566, 2006.
Weylandt et al., "Polyunsaturated fatty acids exert antiarrhythmic actions as free acids rather than in phospholipids," Lipids, 31:977-982 (1996).
Whitney, et al., "Individuality and Variation in Gene Expression Patterns in Human Blood," PNAS, Feb. 18, 2003, vol. 100, No. 4, 1896-1901.

Yang et al.; Circumvention of Normal Constraints on Granule Protein Gene Expression in Peripheral Blood Neutrophils and Monocytes of Patients with Antineutrophil Cytoplastnic Autoantibody-Associated Glomerulonephritis; JAM Soc Nephrol vol. 15 pp. 2103-2114 2004.
Zakynthinos, Epaminondas et al. Inflammatory biomarkers in coronary artery disease. Journal of Cardiology (2009) 53, 317-333.
Zamora, et al., "The Hematologist," Scientific Psychic Poster, 2007.
Zaslona et al., Transcriptome profiling of primary murine monocytes, lung macrophages and lung dendritic cells reveals a distinct expression of genes involved in cell trafficking, Respiratory Research. Jan. 16, 2009. 10:2, pp. 1-16.
Arumugam et al., "S100P promotes pancreatic cancer growth, survival, and invasion." Clinical Cancer Research 11 (15):5356-5364 (2005).
Chaussable et al., "Unique gene expression profiles of human macrophages and dendritic cells to phylogenetically distinct parasites." Blood 102(2):672-681 (2003).
English Translation of Office Action issued in corresponding Chinese Patent Application No. 200980109695.4, dated Mar. 5, 2013.
Galati et al. "In vivo administration of GM-CSF promotes the clearance of apoptotic cells: effects on monocytes and polymorphonuclear leukocytes." Journal of Leukocyte Biology 67(2):174-182 (2000).
Gerna et al., "Comparative quantitation of human cytomegalovirus DNA in blood leukocytes and plasma of transplant and AIDS patients." Journal of Clinical Microbiology 32(11):2709-2717 (1994).
Henry et al., "Antigen-presenting cells that phagocytose apoptotic tumor-derived cells are potent tumor vaccines." Cancer Research 59(14):3329-3332 (1999).
Kagan et al., "Appetizing rancidity of apoptotic cells for macrophages: oxidation, externalization, and recognition of phosphatidylserine." American Journal of Physiology—Lung Cellular and Molecular Physiology 285(1):L1-L17 (2003).
Kruger et al., "The additive effect of p53 Arg72Pro and RNASEL Arg462Gln genotypes on age of disease onset in Lynch syndrome patients with pathogenic germline mutations in MSH2 or MLH1." Cancer Letters 252(1):55-64 (2007).
Larson et al., "Apoptosis of circulating tumor cells in prostate cancer patients." Cytometry Part A 62(1):46-53 (2004).
Loubiere et al. "Maternal microchimerism in healthy adults in lymphocytes, monocyte/macrophages and NK cells." Laboratory Investigation 86(11):1185-1192 (2006).
Merdad et al., "Expression of matrix metalloproteinases (MMPs) in primary human breast cancer: MMP-9 as a potential biomarker for cancer invasion and metastasis." Anticancer Research 34(3):1355-1366 (2014).
Nagorsen et al., "Tumor-infiltrating macrophages and dendritic cells in human colorectal cancer; relation to local regulatory T cells, systemic T-cell response against tumor-associated antigens and survival," Journal of Translational Medicine 5:62 (2007).
Parekh et al., "Therapeutic targeting of the BCL6 oncogene for diffuse large B-cell lymphomas." Leukemia & Lymphoma 49(5):874-882 (2008).
Prasse et al., "IL-10-producing monocytes differentiate to alternatively activated macrophages and are increased in atopic patients." Journal of Allergy and Clinical Immunology 119(2):464-471 (2007).
Rennert et al., "An alternative spliced RNASEL variant in peripheral blood leukocytes." Journal of Interferon & Cytokine Research 26(11):820-826 (2006).
Tang et al., "Gene expression in blood changes rapidly in neutrophils and monocytes after ischemic stroke in humans: a microarray study." Journal of Cerebral Blood Flow & Metabolism 26(8):1089-1102 (2006).
Jjam et al., "Isolation of monocytes from human peripheral blood using immuno-affinity expanded-bed adsorption." Biotechnology and Bioengineering 83(5):554-566 (2003).
Shields et al., "10 new mammals discovered in past 10 years." The Guardian [Retrieved Jul. 12, 2019] <https://www.theguardian.com/environment/2012/sep/13/new-mammals-discovered-10-years> (2012).
Archacki et al. "Expression profiling of cardiovascular disease" Human Genomics 1(5): 355-370 (2004).

(56) References Cited

OTHER PUBLICATIONS

Denmeade et al., "Concentration of Enzymatically Active Prostate-Specific Antigen (PSA) in the Extracellular Fluid of Primary Human Prostate Cancers and Human Prostate Cancer Xenograft Models." The Prostate 48(1): 1-6 (2001).
NCBI Bookshelf ID NBK7572—Strachan et al., "Chromosomes in Cells" Human Molecular Genetics—Chapter 2: 1-16 (1999).
Wu et al., "A Model Based Background Adjustment for Oligonucleotide Expression Arrays." Journal of the American statistical Association 99(468): 909-917 (2004).
Vankayalapati et al. "The NKp46 Receptor Contributes to NK Cell Lysis of Mononuclear Phagocytes Infected with an Intracellular Bacterium" The Journal of Immunology 168(7): 3451-3457 (2002).

* cited by examiner

Table 3. Yield and Quality of RNA Obtained from Mouse WBC

|  | Yield (µg) | 28S/18S Ratio | RNA Integrity Number (RIN) |
|---|---|---|---|
| Macrophage* | 0.53 ± 0.22 | 1.9 ± 0.2 | 9.4 ± 0.8 |
| T cells* | 0.42 ± 0.20 | 1.9 ± 0.3 | 8.4 ± 0.9 |
| Neutrophils* | 0.62 ± 0.16 | 1.9 ± 0.3 | 9.6 ± 0.7 |

*Mean of = 6 cell preparations each.

FIG. 8

Normal Tissue

Tumor Tissue

Neutrophil

T-cells

FIG. 18A
Macrophages
FIG. 18B
T-cells
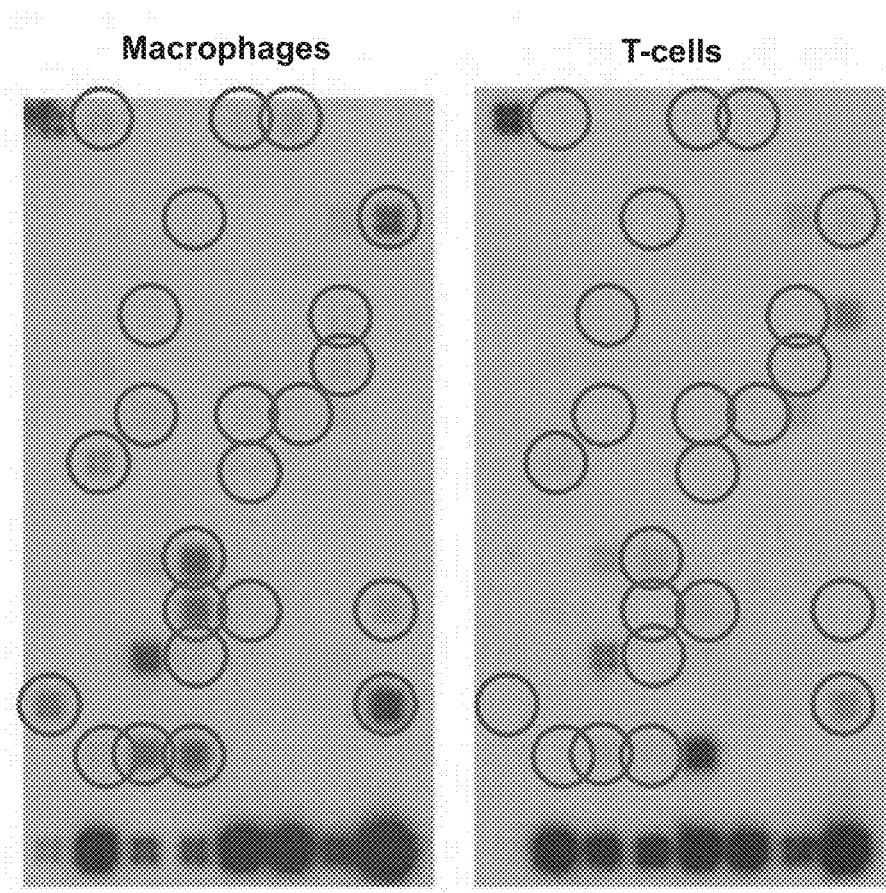
FIG. 19
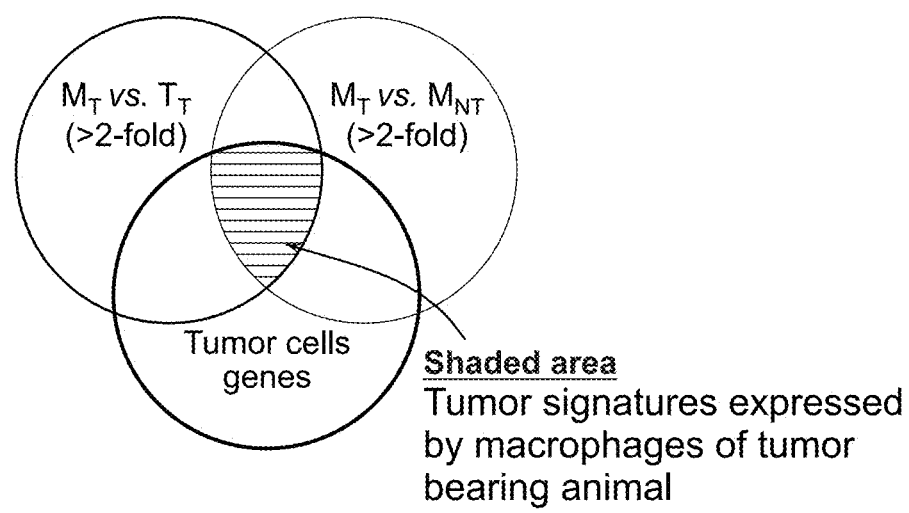

$M_{LNCaP}$ vs. T cells$_{LNCaP}$ $N_{LNCaP}$ vs. $T\ cells_{LNCaP}$

Table 6. Upregulated (>2-fold) cancer-related genes in macrophages of ovarian cancer patient

| Gene Symbol | Macrophages/T cells |
| --- | --- |
| AKT1* | 4.62 |
| APAF1 | 4.95 |
| ATM | 5.26 |
| CDC25A | 2.01 |
| CDKN1A | 4.57 |
| ETS2 | 3.47 |
| FOS | 6.49 |
| IL8 | 3.62 |
| ITGA4 | 6.58 |
| ITGA6 | 3.53 |
| ITGAV | 2.50 |
| JUN | 3.01 |
| MAP2K1 | 3.09 |
| NFKBIA | 2.77 |
| PLAU | 2.13 |
| PLAUR | 38.79 |
| RAF1 | 8.13 |
| SERPINB2 | 5.37 |
| SYK | 20.81 |
| TIMP1 | 2.04 |
| TNF | 3.75 |
| TNFRSF10B | 3.67 |
| TNFRSF1A | 6.96 |

* = oncogene

FIG. 22

METHODS OF DETECTING SIGNATURES OF DISEASE OR CONDITIONS IN BODILY FLUIDS

RELATED U.S. APPLICATIONS

This application is a continuation of U.S. patent application Ser. No. 15/338,786, filed on Oct. 31, 2016, now U.S. Pat. No. 10,934,589, which is a continuation of U.S. patent application Ser. No. 15/069,173, filed on Mar. 14, 2016, which is a continuation of U.S. patent application Ser. No. 14/812,315, filed on Jul. 29, 2015, which is a continuation of U.S. patent application Ser. No. 13/349,670, filed on Jan. 13, 2012, which is a divisional of U.S. patent application Ser. No. 12/836,191, filed on Jul. 14, 2010 which is a continuation of PCT Application number PCT/US2009/031395 designating the United States and filed Jan. 19, 2009 which claims the benefit of the filing date of U.S. Provisional Patent Application Nos. 61/073,434, filed on Jun. 18, 2008 and 61/022,033, filed on Jan. 18, 2008, each of which is hereby incorporated herein by reference in its entirety for all purposes.

STATEMENT OF GOVERNMENT INTERESTS

This invention was made with government support under CA143101 and CA145868 awarded by the National Institutes of Health and W81XWH-09-1-0210 awarded by the U.S. Army/Medical Research and Materiel Command. The government has certain rights in the invention.

FIELD

The present invention relates to methods of identifying markers of conditions such as gender of a fetus or disease such as tumor genomic, proteomic, metabolomic, glycomic, glycoproteomic, lipidomic and/or lipoproteomic signatures in cells obtained from bodily fluids of a patient.

BACKGROUND

Tumors originate from normal cells upon the accumulation of genetic and epigenetic alterations. This multi-step process involves multiple genetic alterations that lead to the progressive transformation of normal cells to a malignant phenotype. These alterations are comprised of irreversible changes in DNA sequence (e.g., mutations, deletions, translocations) and lead to the activation of oncogenes, inactivation of tumor suppressor genes, and fusion of genes. The stochastic nature of these events confers genetic heterogeneity that gives the transformed cells molecular fingerprints (e.g., one or more cellular components such as DNA, RNA, protein, lipid, carbohydrate, and the like) indicative of cancer that give them unique phenotypes. Consequently, unique gene set hallmarks/signatures are known to be expressed by various tumors (Perou et al. (2000) Nature 406:747; Lobenhofer et al. (2001) Health Perspect. 109:881; van't Veer et al. (2002) Nature 415:530 (2002); Liotta and Kohn (2003) Nat. Genet. 33:10; Ginos et al. (2004) Cancer Res. 64:55; Liu (2005) Proc. Natl. Acad. Sci. USA 102:3531; Grigoriadis et al. (2006) Breast Cancer Research 8:R56).

Both primary and metastatic tumors can lie silent and undetected for years. However, these dormant and occult tumors, as well as previously diagnosed primary and metastatic solid tumors, shed daily into the circulation approximately one-to-six million cells per gram of tumor. A large proportion of these circulating tumor cells, known as CTCs, undergo apoptosis and die, whereas distinct cell populations may develop into metastatic disease. Tumor cell apoptotic bodies, DNA, nucleosomes, RNA, and proteins are also found in the blood of cancer patients. Holmgren et al., Blood 93, 3956 (1999). Efforts have been made to investigate whether signatures of tumors can be identified and whether they can be used to detect or monitor cancer. See, Ransohoff, Nature Reviews Cancer 5, 142 (2005) and McLerran et al., Clin. Chem. 54, 44 (2008).

DNA can be easily transfected into various eukaryotic cells, i.e., once it is internalized into the cytoplasm of cells, it is able to integrate its genes into the genome of the host cell. For example, neutrophils and macrophages can be rapidly and very efficiently (50%-90%) transfected. Passage of DNA from prokaryotic to eukaryotic cells has also been demonstrated and is believed to occur from eukaryotic to eukaryotic cells. DNA released from tumor cells has a high transforming activity. Adding supernatant medium from cultured tumor cells to normal cells results in the appearance of as many transformed foci as those occurring after a transfection with a cloned ras gene administered as a calcium precipitate. Furthermore, when healthy rats were injected with plasma from tumor-bearing rats (therefore containing tumor DNA) the tumor marker gene was found in the DNA of their lung cells, i.e., tumor genes have been transcribed in lung cells.

Leukocytes begin as pluripotent hematopoietic stem cells in the bone marrow and develop along either the myeloid lineage (monocytes, macrophages, neutrophils, eosinophils, and basophils) or the lymphoid lineage (T and B lymphocytes and natural killer cells). The major function of the myeloid lineage cells (e.g., neutrophils and macrophages) is the phagocytosis of infectious organisms, live unwanted damaged cells, senescent and dead cells (apoptotic and necrotic), as well as the clearing of cellular debris. Phagocytes from healthy animals do not replicate and are diploid, i.e., have a DNA index of one. On average, each cell contains <10 ng DNA, <20 ng RNA, and <300 ng of protein.

Distinct gene expression patterns of variation, e.g., those associated with cell type, gender, age, interindividual differences and the like, have been recognized in WBCs of healthy donors. For example, a "lymphocyte-associated" cluster has 55 unique genes. In neutrophils, significant variability in the expression of 52 unique gene clusters has also been reported. The genes in this cluster can be grouped into three increasingly specific families: (i) those ubiquitously expressed in many types of circulating immune cells; (ii) those expressed by cells of the myeloid lineage; and (iii) those specific to granulocytes.

The lifetime of various WBC subpopulations varies from a few days (e.g., neutrophils) to several months (e.g., macrophages). Like other cell types, leukocytes age and eventually die. During their aging process, human blood- and tissue-derived phagocytes (e.g., neutrophils) exhibit all the classic markers of programmed cell death (i.e., apoptosis), including caspase activation, pyknotic nuclei, and chromatin fragmentation. These cells also display a number of "eat-me" flags (e.g., phosphatidylserine, sugars) on the extracellular surfaces of their plasma membranes. Consequently, dying and dead cells and subcellular fragments thereof are cleared from tissues and blood by other phagocytic cells.

The apoptosis of phagocytes is accelerated following their activation. For example, following the engulfment of S. aureus by neutrophils, phosphatidylserine is externalized on their plasma membranes, thereby leading to their rapid phagocytosis by macrophages. Activated monocytes have also been shown to bind various tumor-cell lines with elevated levels of phosphatidylserine. Circulating phagocytic cells are known to engulf live and dead CTCs and fragments thereof, a process that leads to an increase in the DNA (and other cellular constituent) contents of the phagocytosing cell. For example, apoptotic tumor cells have been shown to be phagocytosed by macrophages and dendritic cells. Consequent to such phagocytic activity, blood macrophages obtained from prostate cancer patients have been shown to contain intracellularly much higher levels of prostate-specific antigen (PSA) than macrophages obtained from patients with benign prostate conditions. See, Herwig et al., *Clinical Prostate Cancer* 3, 184 (2004) and Herwig et al., *Prostate* 62 290 (2005). This is believed to be a consequence of phagocytosing tumor cells. Fetal stem cells, nucleated erythrocytes, fetal lymphocytes, as well as significant amounts of cell-free fetal nucleic acids are known to circulate in maternal blood. See Cheung et al., *Nat. Genet.* 14, 264 (1996).

It has also been shown that when apoptotic bodies (membrane-encapsulated cell fragments) derived from human Burkitt's lymphoma cells are cultured with human monocytes (phagocytic) or vascular smooth muscle cells (non-phagocytic), the monocytes show a high percentage of Epstein-Barr virus (EBV)-specific, tumor-gene-positive cells, whereas smooth muscle cells exhibit approximately 0.01% frequency of uptake and expression.

Methods are needed that enable the early diagnosis of the presence of disease (e.g., tumors) in individuals, e.g., individuals who are not known to have the disease or who have recurrent disease. One object of the present invention is to facilitate the detection of disease-specific (e.g., tumor-specific) markers, e.g., proteins, RNA, DNA, carbohydrates and/or lipids and the like within subpopulations of white blood cells (WBCs) in an animal, including a human.

SUMMARY

Embodiments of the present invention are based on the use of phagocytes to determine the presence or absence of markers associated with certain diseases or conditions. According to certain embodiments of the present invention, phagocytes incorporate cells and/or fragments and/or components thereof circulating in blood that are characteristic of a particular disease or condition. The contents of the phagocytes provide a marker profile for the disease or condition, for example through DNA and/or proteins content in the cell or through DNA or protein expression by the cell. Comparison of DNA expression profiles of phagocytic and non-phagocytic WBC lead to the detection of tumor specific, disease specific or condition specific DNA signatures within phagocytic cells that were either not expressed or under-expressed in the non-phagocytic cell. Likewise, protein expression profiles of phagocytic and non-phagocytic WBC lead to the detection of tumor specific, disease specific or condition specific protein signatures within phagocytic cells that were either not expressed or under-expressed in the non-phagocytic cell. Accordingly, in certain embodiments, the methods of the present invention identify the presence of solid tumors (e.g., primary and metastatic lesions) in an individual suspected of having cancer and/or identify the presence of cancer prior to the manifestation of pathologic signs and symptoms and detect disease recurrence. According to other embodiments, the methods of the present invention diagnose certain diseases or other conditions by identifying specific signatures from blood or other bodily fluid.

The present invention is based in part on the discovery that blood cell components, such as phagocytic cells and non-phagocytic cells, of an individual are ideally suited for the facile identification and differentiation of tumor specific and normal, non-specific signatures and therefore the elimination of the inequality of baseline consequent to intrinsic interindividual (e.g., age, gender, ethnic background, health status) and temporal variations in gene expressions.

In certain exemplary embodiments, methods for the identification of tumor- and/or other disease-specific signatures within the WBCs (obtained from the blood or other bodily fluids, e.g., urine, stool, saliva, lymph, cerebrospinal fluid and the like) of an individual suspected of having cancer and/or one or more other diseases or disorders or conditions are provided. Embodiments of the present invention provide patient specific results and are not dependent on population-derived average signature profiles and values obtained from "healthy" controls, i.e., the baseline/background signature(s) is/are specific to the genomic, proteomic, metabolomic, glycomic, glycoproteomic, lipidomic, and/or lipoproteomic profile(s) of the individual being evaluated. Embodiments of the present invention provide a personalized predisposition to, screening, diagnosis, and monitoring of disease.

In certain embodiments and with reference to FIG. 1, the present invention is based on the ability of phagocytic cells to engulf and ingest viable, dying and dead cells (e.g., apoptotic cells, necrotic cells), microorganisms (e.g., bacteria (e.g., *Rickettsia*), viruses, fungi, yeast, protozoa and the like) subcellular particles and/or fragments thereof (cajal bodies, cell membrane, centrioles, centrosomes, gems, golgi apparatus, lysosomes, mitochondria, nuclear membrane, nuclei, nucleolus, paraspeckles, promyelocytic leukemia bodies (PML bodies), ribosomes, rough endoplasmic reticulum, smooth endoplasmic reticulum, vacuoles, vesicles, microvesicles, and the like), and cellular debris, e.g. chromosomes, DNA (nuclear and mitochondrial), exons, genes, introns, proteins, prions, carbohydrate-binding proteins, glycoproteins, lipoproteins, RNA, microRNA, lipids, apoptotic bodies, nuclei, microvesicles, exosomes, nucleosomes, polymorphic interphase karyosomal associations (PIKA), splicing spreckles, and the like), and the absence of these characteristics in non-phagocytic cells. Accordingly, the analysis of DNA (nuclear, mitochondrial), RNA, microRNA, protein, prions, carbohydrate binding proteins, glycoproteins, lipids, lipoproteins, apoptotic bodies, nuclei, microvesicles, exosomes and/or nucleosomes and/or expression profiles of phagocytic WBCs and their comparison with those from non-phagocytic cells obtained from the blood or other bodily fluids of the same donor provides an identification of tumor- and/or disease-specific signatures within the phagocytic cells (patient-specific signal) that are either not expressed or significantly differentially expressed in the non-phagocytic cells (patient-specific noise). Since both phagocytic and non-phagocytic cells arise from the same pluripotent stem cell within the bone marrow, subtraction of the non-tumor-associated/induced signature profile (identified in the non-phagocytic cells) from the signatures found in the phagocytic cells allows the identification of tumor- and/or disease-specific signatures in the sample of the particular patient as shown in FIG. 2. According to certain other embodiments, cellular debris in bodily fluids is internalized by entosis (cell absorption), endocytosis and pinocytosis.

According to one embodiment of the present invention and with reference to FIG. 3, a blood sample is obtained from an individual with the blood sample including both phagocytic and non-phagocytic cells (e.g., WBCs). Phagocytic cells(s) (e.g., neutrophils, monocytes, macrophages dendritic cells, foam cells) are then separated from non-phagocytic (e.g., T cells, B cells, null cells, basophils) cell(s) by various methods known to those of skill in the art. According to the present invention, the phenotype of WBCs is altered by the phagocytosis of live/dying/dead CTCs (and subcellular fragments thereof) and/or tumor- and/or disease-specific DNA, RNA, protein, carbohydrate and/or lipid present in blood. Phagocytosis leads to the internalization of these tumor and/or disease signatures into the phagocytosing cell and possibly the integration of tumor-cell DNA with its tumor-specific somatic mutations (or other disease-related mutations) into the normal phagocytic cell DNA (i.e., its transfection of the chromosomes of the target cell). The subsequent transcription of the "transfected" DNA of phagocytic cells into RNA and the translation of the latter into proteins produces a phenotype different from non-phagocytic WBCs.

Therefore, comparison using genomic, proteomic, metabolomic, glycomic, glycoproteomic, lipidomic and/or lipoproteomic methods known to those of skill in the art of the DNA, RNA, protein, and/or lipid expression profiles of phagocytic and non-phagocytic WBCs (as shown in FIG. 3) obtained from an individual with cancer (and/or one or more other diseases) is used to identify tumor-specific (and/or disease-specific and/or condition specific) signature(s) and/or profile(s) selectively in the phagocytic cells which confirm the presence of occult tumor(s) (or other diseases or conditions) in the individual. According to the present invention, the subtraction of the DNA, RNA, protein, carbohydrate and/or lipid profiles of phagocytic cells from non-phagocytic cells provides a method for the identification (e.g., after genomic, proteomic, metabolomic, glycomic, glycoproteomic, lipidomic and/or lipoproteomic analyses) of tumor-specific (and/or disease-specific) signatures in a blood sample (and/or other biological sample) of a particular patient and signify the presence of occult tumor(s) and/or other disease as shown in FIG. 2.

In certain exemplary embodiments, phagocytic and non-phagocytic cells (e.g., obtained from the blood or one or more other biological samples (e.g., urine, stool, saliva, lymph, cerebrospinal fluid and the like), are separated. Since the phagocytosis of CTCs (and subcellular fragments thereof) by phagocytic WBC leads to the internalization of the tumor cells into the cytoplasm of phagocytic cells, the quantity of DNA, RNA, protein, carbohydrate and/or lipid within phagocytic cells will be higher than that of non-phagocytic cells. Therefore, comparison of the quantity and profile of these components between the phagocytic and non-phagocytic cells is used as an indication of the presence of cancer.

In certain exemplary embodiments, a method for diagnosing the presence of a cancer cell in an individual is provided. The method includes the steps of obtaining a first expression profile from a blood phagocytic cell from an individual, obtaining a second expression profile from a blood non-phagocytic cell from the individual, comparing the first and second expression profiles, identifying differential expression of one or more markers specific to the first expression profile, and relating the differential expression of the one or more markers specific to the first expression profile to the presence of a cancer cell in the individual.

In certain exemplary embodiments, a method for identifying a tumor-specific signature in an individual having cancer is provided. The method includes the steps of obtaining a first expression profile from a blood phagocytic cell from an individual having cancer, obtaining a second expression profile from a blood non-phagocytic cell from the individual having cancer, comparing the first and second expression profiles, identifying differential expression of two or more markers specific to the first expression profile, and relating the differential expression of the two or more markers specific to a tumor-specific signature in the individual having cancer.

In certain exemplary embodiments, a method for diagnosing the presence of a cancer cell in an individual including the steps of obtaining a first expression profile from a blood phagocytic cell from an individual and obtaining a second expression profile from a blood non-phagocytic cell from the individual is provided. The method includes the steps of comparing the first and second expression profiles, identifying the presence of a circulating tumor cell or subcellular fragment thereof specific to the first expression profile, and relating the presence of a circulating tumor cell or subcellular fragment thereof to the presence of a cancer cell in the individual. In certain aspects, an increase in the quantity of a marker in the first expression profile relative to the second expression profile indicates the presence of a circulating tumor cell or subcellular fragment thereof.

In certain exemplary embodiments and with reference to FIGS. 4-6, a method for diagnosing the presence of a cancer cell in an individual including the steps of isolating a population of phagocytic cells from an individual and separating 2n phagocytic cells from >2n phagocytic cells is provided. The method includes the steps of obtaining a first expression profile from the 2n phagocytic cells, obtaining a second expression profile from the >2n phagocytic cells, comparing the first and second expression profiles, and identifying differential expression of one or more markers specific to the first expression profile. The method also includes the step of relating the differential expression of the one or more markers specific to the first expression profile to the presence of a cancer cell in the individual.

In certain aspects of the methods described herein, markers include DNA, RNA, microRNA (e.g., DNA or RNA corresponding to cancer gene, oncogene, a tumor suppressor gene or any combination of these), protein (e.g., a protein or polypeptide encoded by a cancer gene, oncogene, a tumor suppressor gene or any combination of these), lipid, carbohydrate and/or any combination of these. In certain aspects, a blood phagocytic cell is a neutrophil, a macrophage, a monocyte, a dendritic cell, an eosinophil, a foam cell or any combination of these. In certain aspects, a blood non-phagocytic cell is a T cell, a B cell, a null cell, a basophil or any combination thereof. In other aspects, a blood phagocytic cell and a blood non-phagocytic cell are isolated from whole blood using methods known to those skilled in the art, such as antibodies. In still other aspects, a blood phagocytic cell and a blood non-phagocytic cell are isolated from a population of white blood cells using methods know to those of skill in the art such as fluorescence activated cell sorting (FACS). In other aspects, the blood phagocytic cell and the blood non-phagocytic cell are separated using a ligand that binds to a molecular receptor expressed on the plasma membranes of WBC populations. In yet other aspects, the blood phagocytic cell and the blood non-phagocytic cell are separated by one or methods including filtration, gradient-based centrifugation, elution, microfluidics and the like. In certain aspects, an individual has one or more of occult (e.g., dormant, undiagnosed, hidden or concealed) cancer, previously diagnosed primary cancer and metastatic cancer. In certain aspects, a method includes the step of relating the presence of one or more markers to efficacy of a cancer therapy.

In certain exemplary embodiments, the above described methods are applied to detect, identify or diagnose the presence of an infectious agent or disease other than cancer by comparing expression profiles of phagocytic and non-phagocytic cells to determine differential expression of markers characteristics of the infectious agent or disease other than cancer. In yet another aspect, one or more of the methods described herein are used to detect the DNA, RNA, protein, carbohydrate and/or lipid profiles of pathogens (e.g., viruses, bacteria, rickettsia, protozoans, helminthes, fungi, yeasts and the like) and other diseases or pathologies (e.g., Alzheimer's, dementia, heart failure, atherosclerosis, arthritis, genetic disorders, bone diseases, gastrointestinal diseases, prion diseases, and infectious diseases).

In certain aspects of the methods described herein, markers include pathogen DNA, pathogen RNA, pathogen protein, pathogen polypeptide, pathogen lipid and any combination of these. In certain aspects, an infectious agent is a virus, a bacterium, a fungus, a parasite, an infectious protein and any combination of these. In certain aspects, a method includes the step of relating the presence of one or more markers to the efficacy of a pathogen therapy.

The methods and compositions described herein, therefore, enable the facile identification of tumor specific signatures in the blood sample of a patient, without depending on population-derived average signature profiles and values obtained from "healthy" controls. Specifically, the methods and compositions described herein can easily and economically: (i) identify tumor (primary and metastatic lesions) presence in an individual prior to the manifestation of pathologic signs and symptoms; (ii) identify tumor (primary and metastatic lesions) presence in an individual suspected of having cancer; and/or (iii) detect tumor (primary and metastatic lesions) recurrence in an individual undergoing/following various treatments.

Accordingly, the methods and compositions described herein (i) enable the noninvasive screening of cancer; (ii) allow the diagnosis of tumors, especially at the earliest time points; (iii) move meaningful intervention(s) to a much earlier point in the path of tumor progression, thereby forestalling the development of metastatic disease; (iv) monitor the early response to routine or experimental treatment(s); (v) predict response to routine or experimental treatment(s); (vi) facilitate the selection of effective treatment by allowing rapid identification of ineffective treatments whose side effects might not be balanced by expected benefits; (vii) minimize patient inconvenience and incapacitation; (viii) allow tumor detection, diagnosis, and treatment to be closely coupled (e.g., personalization of anticancer therapy); (ix) provide for prediction and early detection of tumor type and staging; (x) provide for therapy selection; (xi) determine whether a tumor is metastatic or not; (xii) provide methods for the monitoring of diseases; and (xiii) methods for the prognosis of diseases.

BRIEF DESCRIPTION OF THE DRAWINGS

The foregoing and other features and advantages of the present invention will be more fully understood from the following detailed description of illustrative embodiments taken in conjunction with the accompanying drawings in which:

FIG. 8 lists the yield and quality of RNA obtained from mouse white blood cells (WBCs).

FIG. 18A-18B depict arrays showing 23 up-regulated (≥2 fold), cancer related genes detected in macrophages from patient with ovarian cancer (adenocarcinoma). (A) Macrophages obtained from patient blood ($M_T$). (B) T cells obtained from patient blood ($T_T$). Circled signatures expressed in macrophages from patient (A) and minimally expressed in non-phagocytic T cells (B). Expression in $M_T$ was ≥2-fold than that in $T_T$.

FIG. 19 depicts a method used to identify tumor signatures in phagocytic cells. In this example, expression intensities of cancer associated genes in macrophages from tumor-bearing animals ($M_T$) were quantified compared to those from T cells from the same animals ($T_T$) and those overexpressed by ≥2-fold identified. Next, the intensities of all expressed genes in MT were quantified and compared to those in macrophages obtained from non-tumor bearing animals ($M_{NT}$) and the genes overexpressed ≥2-fold were identified. The genes common to both lists were selected and compared to those expressed by the same tumor (shaded area).

FIG. 22 lists cancer-related genes upregulated (>2-fold) in phagocytic macrophages of a patient with ovarian cancer in comparison to non-phagocytic T cells.

DETAILED DESCRIPTION OF CERTAIN EMBODIMENTS

Embodiments of the present invention are directed to a method of providing a patient-specific expression profile of markers associated with diseases, infectious agents and bodily conditions based on the cellular content and/or expression profiles of phagocytic cells. According to one aspect of the present invention, the cellular contents and/or expression profiles of phagocytic cells is compared to known markers for a particular disease state or condition to detect and/or diagnose the particular disease state or condition. According to an additional aspect of the present invention, the cellular content and/or expression profile of phagocytic cells is compared to the cellular content and/or expression profile of non-phagocytic cells from the blood of a single patient. Subtracting the cellular content and/or expression profile from non-phagocytic cells from that of phagocytic cells creates a cellular content and/or expression profile representative of only the disease state of the individual.

According to an additional embodiment of the present invention, a phagocytic cell population from an individual is obtained and the cellular content and/or expression profile of phagocytic cells from the population where the DNA content is greater than 2n is compared with the cellular content and/or expression profile of phagocytic cells from the same population where the DNA content is 2n. According to a still additional embodiment of the present invention, a phagocytic cell population from an individual is obtained and the expression profile of phagocytic cells from the population where the RNA, protein, carbohydrate and/or lipid content is larger than normal and have a DNA index greater than 1 is compared with the expression profile of phagocytic cells from the same population where the RNA, protein, carbohydrate and/or lipid content is normal and/or have a DNA index of 1.

Such a patient specific expression profile eliminates the dependence on a population-derived average signature profile for a particular disease or infectious agent, which may introduce error into the detection or diagnosis of a particular disease in the individual. Such a patient specific expression profile for a disease state of the present invention allows detection, diagnosis and treatment to be personalized to the individual.

Figure 1:
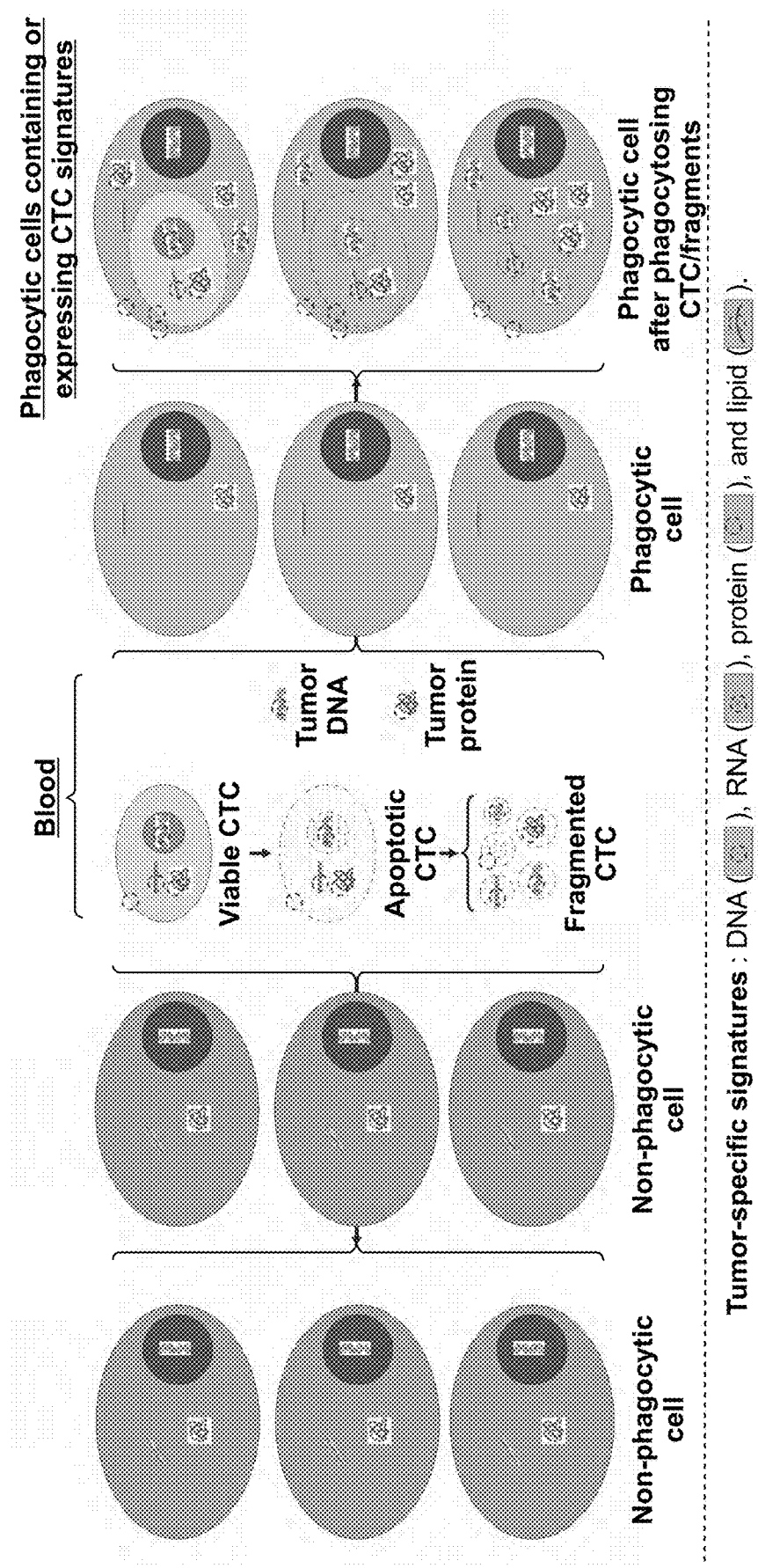
FIG. 1 schematically depicts a proposed pathway leading to acquisition of tumor-specific DNA, RNA, protein and/or lipid signatures by phagocytes following engulfment of live CTCs, apoptotic CTCs, fragmented CTCs, tumor DNA, RNA, proteins, and lipids released by viable and/or apoptotic tumor cells. Note that only phagocytic cells (and not non-phagocytic cells) acquire tumor signatures.
Figure 2:
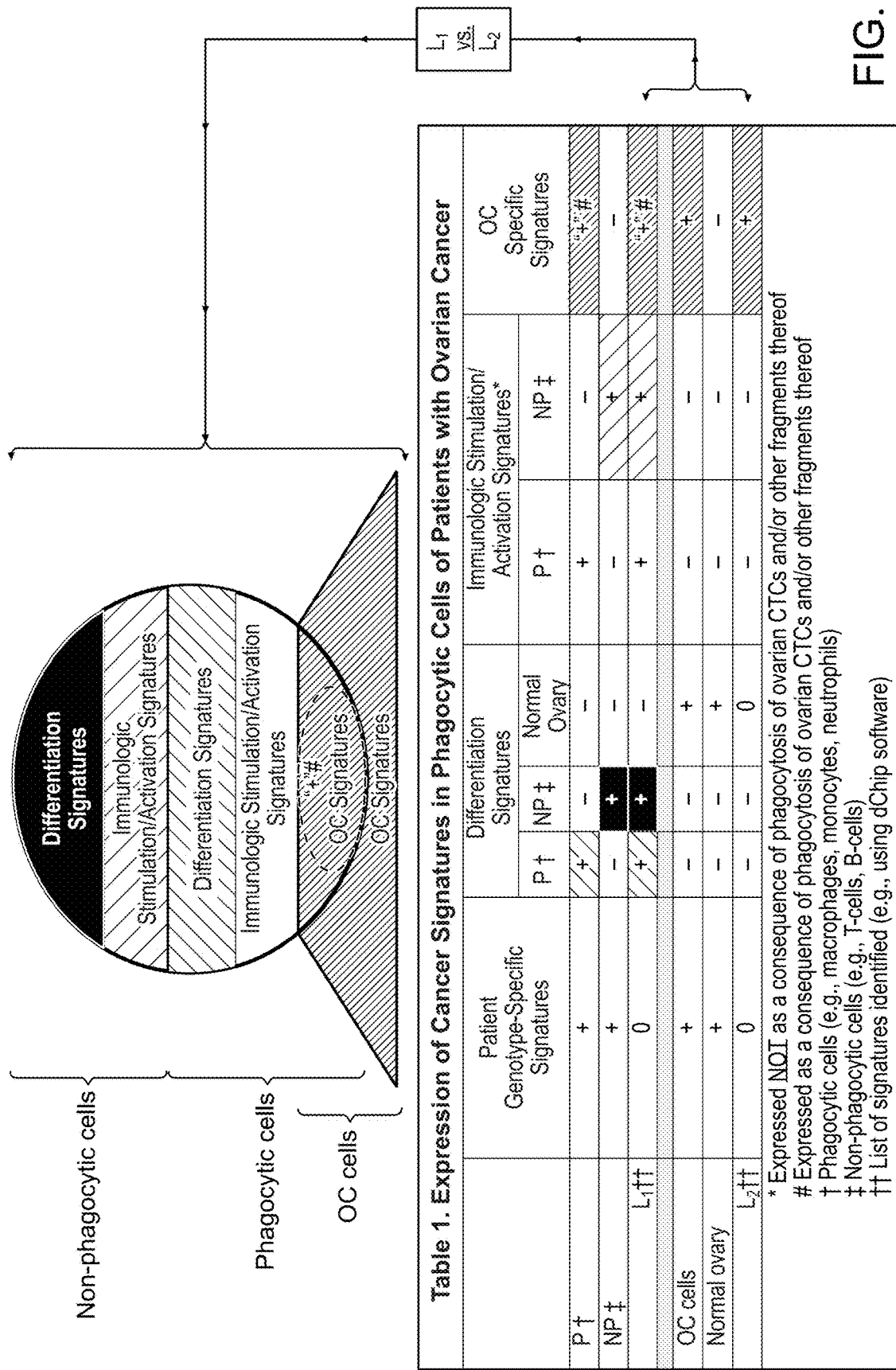
FIG. 2 schematically depicts an analytical method used in the identification of cancer signatures expressed in/by phagocytic cells of patients with ovarian cancer (OC).
Figure 3:
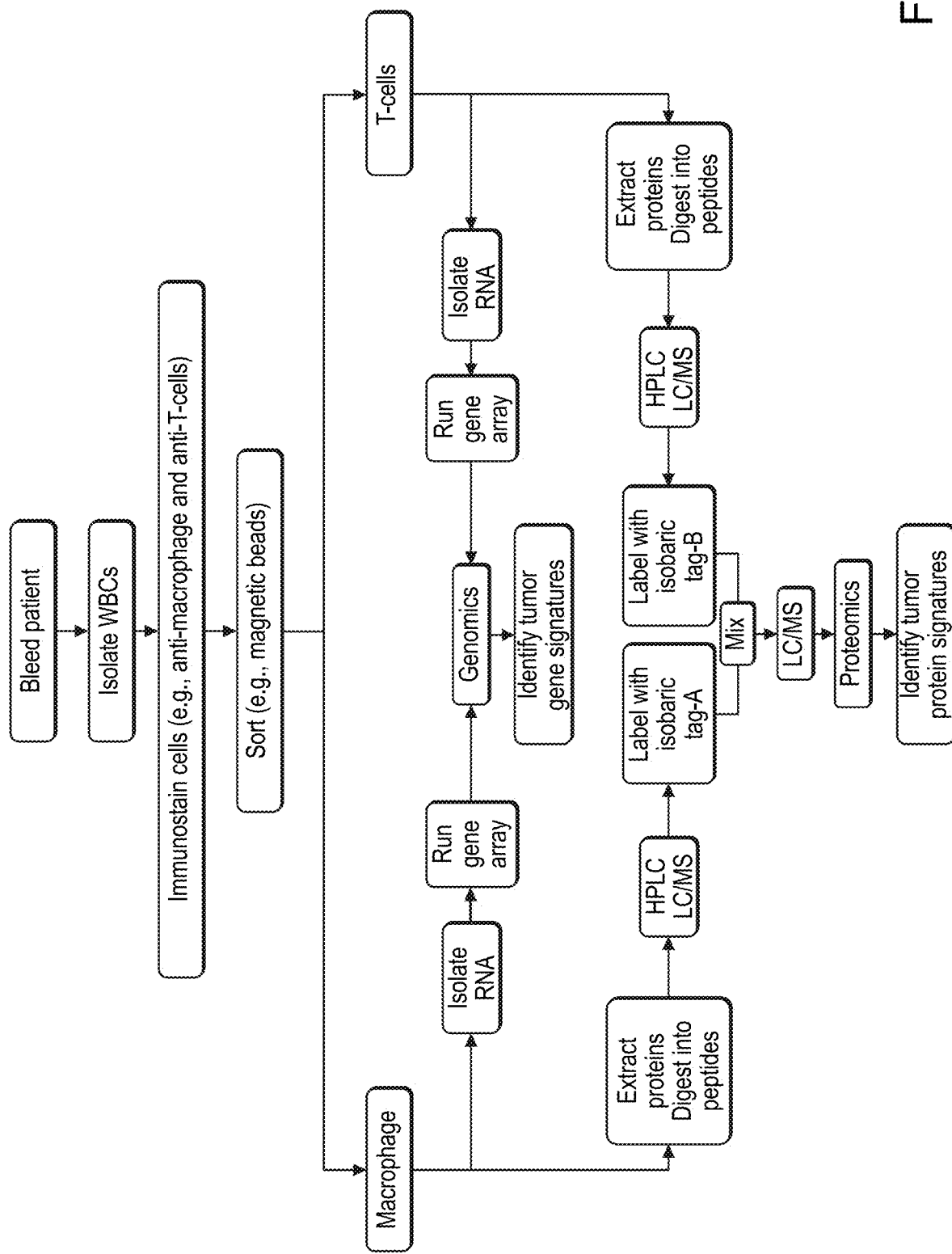
FIG. 3 schematically depicts a general flowchart of one embodiment of a method of the invention.

With reference to FIGS. 1-3 and according to certain embodiments of the present invention, the gene expression profiles of phagocytic and non-phagocytic WBCs obtained from mice bearing approximately three week old human subcutaneous (s.c.) tumors (prostate LNCaP adenocarcinoma or LS174T colon adenocarcinoma) or mouse tumors (B16F10 metastatic melanoma, administered intravenously, or LLC1 lung cancer, injected s.c.), were compared. The results demonstrated that neutrophils and macrophages obtained from these tumor-bearing mice express various oncogenes and other cancer-related gene signatures that are also expressed in each of the respective tumors. See FIGS. 9-16 and 19-21. These cancer-related genes and oncogenes (e.g., ERBB2, Jun, Fos, etc.) are not expressed or are minimally expressed by (i) non-phagocytic T cells isolated from tumor-bearing mice, and (ii) neutrophils and macrophages obtained from non-tumor-bearing mice. Furthermore, only the phagocytic cells from tumor-bearing mice were found to express tumor-specific proteins. See FIGS. 23 and 24. CTCs and/or tumor-specific DNA and/or proteins in the blood of the mice were phagocytosed and some of the tumor-cell DNA, with its tumor-specific mutations and genes, was integrated, likely by transfection (without intending to be bound by theory), into normal phagocyte DNA, transcribed into RNA, and translated into protein.

With reference to FIGS. 1-3 and according to certain exemplary embodiments of the present invention, the gene expression profiles of phagocytic and non-phagocytic WBCs obtained from patients with head and neck tumors or with ovarian cancer were also compared. The results demonstrated that neutrophils and macrophages obtained from these patients express various oncogenes and other cancer-related gene signatures that are also expressed in each of the respective tumors. See FIGS. 17-18 and 22. These cancer-related genes and oncogenes were not expressed or were minimally expressed by non-phagocytic T cells isolated from the same individual patient. CTCs and/or tumor-specific DNA and RNA in the blood of the patient were phagocytosed and some of the tumor-cell DNA and/or RNA, with its tumor-specific mutations and genes, was integrated, likely through transfection (without intending to be bound by theory), into normal phagocyte DNA, transcribed into RNA, and translated into protein.

Figure 4:
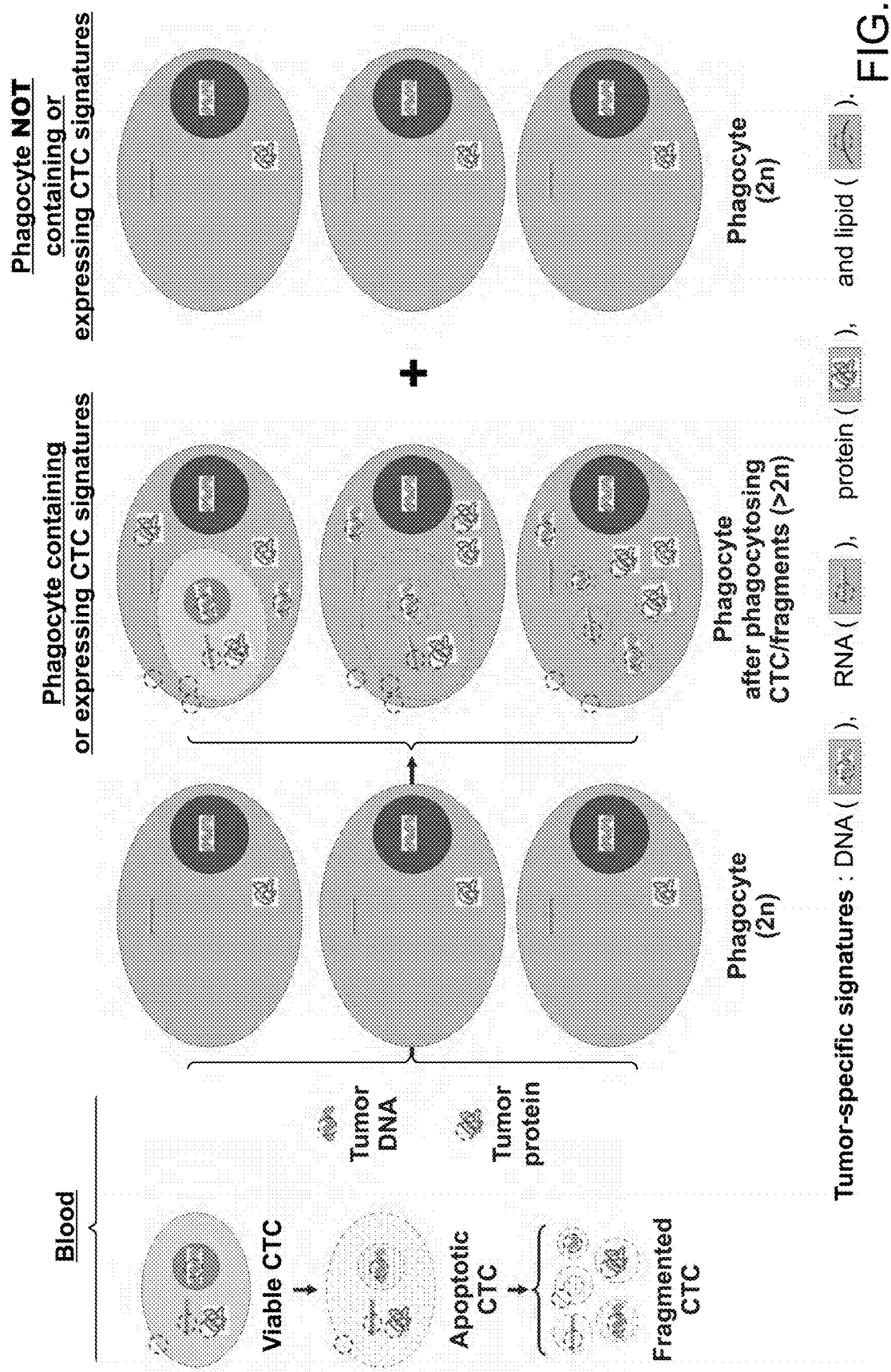
FIG. 4 schematically depicts a proposed pathway leading to acquisition of tumor-specific DNA, RNA, protein and lipid signatures by blood phagocytes following engulfment of live CTCs, apoptotic CTCs, fragmented CTCs, tumor DNA, RNA, proteins and lipids released by viable and/or apoptotic tumor cells. Note that DNA contents of phagocytes following phagocytosis is >2n.
Figure 5:
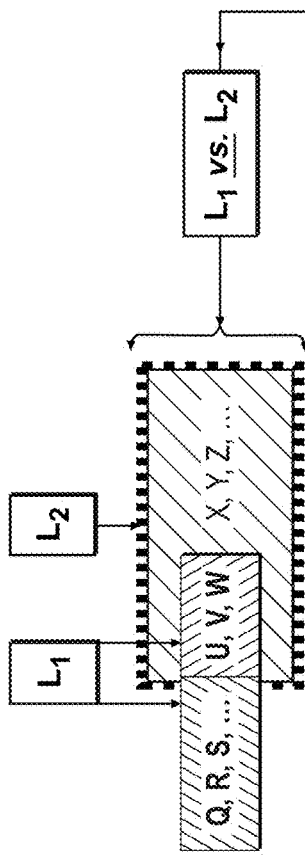
FIG. 5 schematically depicts analytical approaches used in the identification of breast cancer (BC) signatures in BC-bearing animals.
Figure 6:
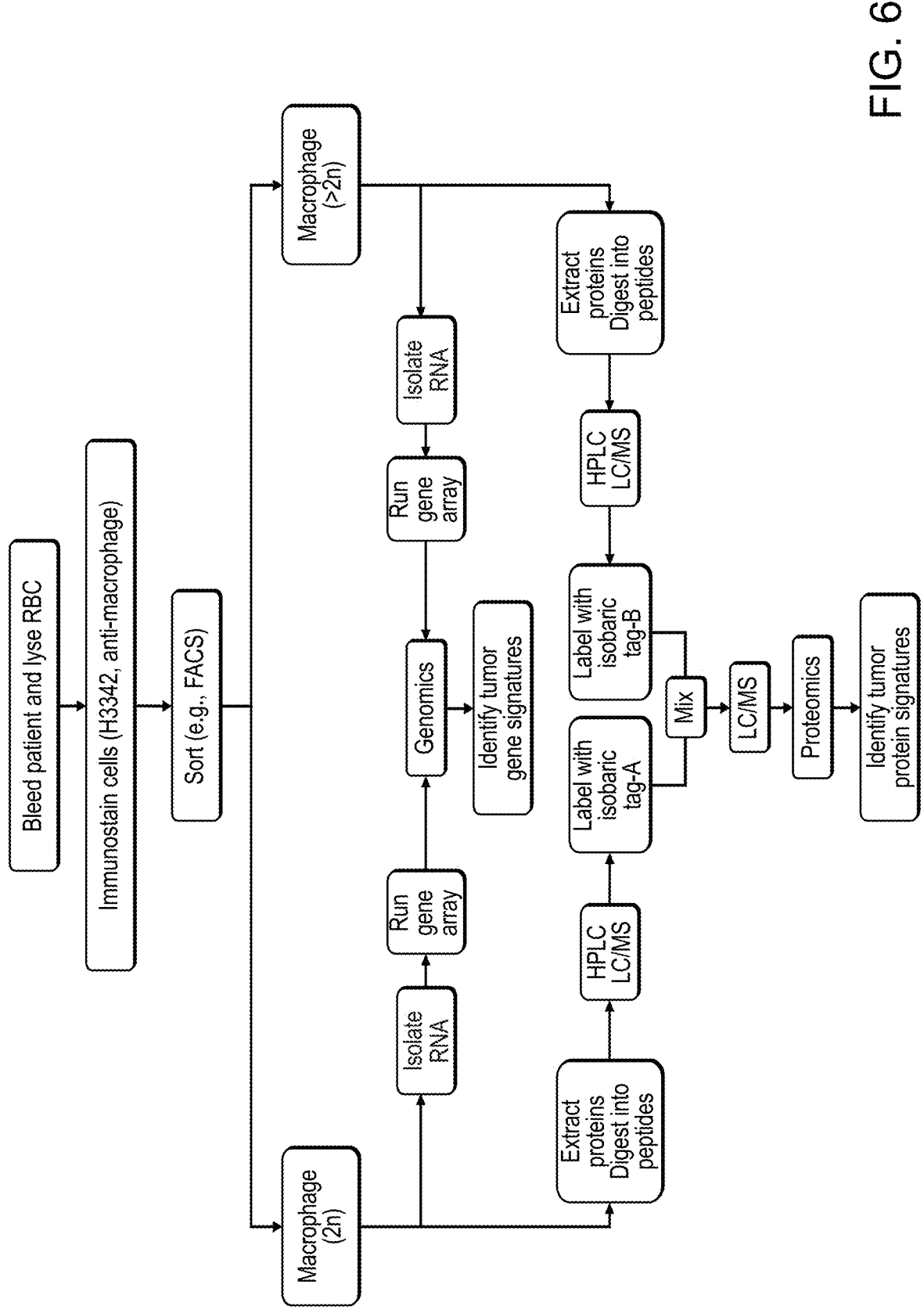
FIG. 6 schematically depicts a general flowchart of another embodiment of a method of the invention.

With reference to FIGS. 4-6 and according to certain exemplary embodiments, the quantitative analysis of DNA (nuclear and/or mitochondrial), RNA, microRNA, protein, and/or lipid expression profiles of phagocytic cells (e.g., macrophages) obtained from the blood or one or more other biological samples (e.g., urine, stool, saliva, lymph, cerebrospinal fluid and the like) whose (1) DNA content is >2n ($P_{n>2}$), or (2) RNA, protein, carbohydrate and/or lipid content is larger than normal, i.e., cells that have phagocytosed CTCs and/or their subcellular fragments or DNA/RNA/lipids (i.e., tumor-specific signatures or other disease-specific signatures) and/or have a DNA index greater than one, and their comparison with the same phagocytic cell population (e.g., macrophages) whose (1) DNA content is 2n ($P_{n=2}$), or (2) RNA, protein, carbohydrate and/or lipid content is normal, i.e., cells that have not phagocytosed CTCs and/or their subcellular fragments and have a DNA index of one, provides a method to detect tumor-specific (or other disease-specific) signatures within the $P_{n>2}$ cells (patient-specific signal) that are either not expressed or minimally expressed in the $P_{n=2}$ cells (patient-specific noise). With reference to FIG. 6, the subtraction of the DNA, RNA, protein, and/or lipid profiles of $P_{n=2}$ from those of $P_{n>2}$ as shown in FIG. 5 provides a method to identify (e.g., after one or more genomic, proteomic, metabolomic, glycomic, glycoproteomic, lipidomic and/or lipoproteomic analyses) tumor-specific (and/or disease-specific and/or condition specific) signatures in a blood sample (or one or more other biological samples such as, e.g., other bodily fluids) of an animal and/or a human with cancer (and/or disease and or bodily conditions) and signify the presence of occult tumor (s) and/or other disease and/or other conditions. Unlike the methods described above in which the genomic, proteomic, metabolomic, glycomic, glycoproteomic, lipidomic and/or lipoproteomic profiles of phagocytic cells are compared with those of non-phagocytic cells, the major advantages of this analytic detection method according to the present invention are: (i) it utilizes a single phagocytic cell subpopulation as a source of the "tumor-specific" (e.g., $P_{n>2}$ macrophage) and "normal-non-specific" (e.g., $P_{n=2}$ macrophage) signatures, i.e., both share the same baseline genotype; and (ii) the signature-acquiring cells (e.g., $P_{n>2}$ neutrophil) are not diluted with those that have not phagocytosed, and therefore have not acquired, dead CTCs and/or fragments thereof (e.g., $P_{n=2}$ neutrophils).

With reference to FIGS. 4-6 and according to certain exemplary embodiments, the quantitative analysis of phagocytic cells (e.g., macrophages) obtained from the blood or one or more other biological samples or bodily fluid (e.g., urine, stool, saliva, lymph, cerebrospinal fluid and the like) whose intracellular content consequent to phagocytosis or internalization of other live, dying, or dead (e.g., apoptotic or necrotic) cells, apoptotic bodies, nuclei, microvesicles, exosomes, nucleosomes, mitochondria, endoplasmic reticulum, and the like, is greater than that of the same phagocytic cell population (e.g., macrophages) with normal intracellular contents ($P_{NIC}$), i.e., cells that have not phagocytosed any of the above mentioned cells and/cellular debris (patient-specific noise), provides a method to detect tumor-specific (or other disease-specific or other condition specific) signatures within the phagocytes with increased intracellular content ($P_{IIC}$) that are either not expressed or minimally expressed in the phagocytes with a normal intracellular contents (patient-specific noise). With reference to FIG. 6, the subtraction of the DNA, RNA, protein, and/or lipid profiles of $P_{NIC}$ from those of $P_{IIC}$ as shown in FIG. 5 provides a method to identify (e.g., after one or more genomic, proteomic, metabolomic, glycomic, glycoproteomic, lipidomic, and/or lipoproteomic analyses) tumor-specific (and/or disease-specific) signatures in a blood sample (or one or more other biological samples such as, e.g., other bodily fluids) of an animal with cancer or other disease and signify the presence of occult tumor(s) and/or other disease. Unlike the methods described above in which the genomic, proteomic, metabolomic, glycomic, glycoproteomic, lipidomic, and/or lipoproteomic profiles of phagocytic cells are compared with those of non-phagocytic cells, the major advantages of this analytic detection method according to the present invention are: (i) it utilizes a single phagocytic cell subpopulation as a source of the "disease-specific" (e.g., $P_{IIC}$ macrophage) and "normal-non-specific" (e.g., $P_{NIC}$ macrophage) signatures, i.e., both share the same baseline genotype; and (ii) the signature-acquiring cells (e.g., $P_{IIC}$ neutrophil) are not diluted with those that have not phagocytosed, and therefore have not acquired, dead CTCs and/or fragments thereof (e.g., $P_{NIC}$ neutrophils).

The methods described herein (i) have high specificity, sensitivity, and accuracy and should enable the detection of tumor-specific (and/or other disease-specific) and normal-nonspecific signatures present within a blood sample (or other biological sample such as, e.g., a bodily fluid); and (ii) eliminate the "inequality of baseline" that is known to occur among individuals due to intrinsic (e.g., age, gender, ethnic background, health status and the like) and temporal variations in gene expression. Accordingly, in certain aspects, the invention provides non-invasive assays for the early detection of occult primary and metastatic tumors (and/or one or more other diseases or conditions) in patients, i.e., before the disease can be diagnosed by conventional imaging techniques (e.g., PET, MRI, CT and the like), and, therefore, provide a foundation for improved decision-making relative to the needs and strategies for intervention, prevention, and treatment of individuals with cancer.

As used herein, the term "tumor specific marker" is intended to include, but is not limited to, one or more cellular components such as one or more DNA sequences, one or more RNA sequences, one or more proteins, one or more polypeptides, one or more lipids and the like. In certain aspects, a tumor specific marker is present in one or more WBCs such as, for example, a neutrophil, a macrophage and/or a dendritic cell.

As used herein, the term "cancer related genes" refers to genes such as, for example, cancer genes, oncogenes and/or tumor suppressor genes, that have altered expression (e.g., increased expression or decreased expression when compared to a non-cancerous cell) in a cancerous cell (e.g., a WBC such as, for example, a macrophage, a neutrophil, a T cell or the like). Many cancer related genes are known in the art. Cancer related genes include for example, but are not limited to, ERBB2, JUN, RB1, SUPP1, MDM2, MAP2K1, MMP2, PDGFB, PLAUR, FGR, MYCL1, BLYM, NRAS1, PE1, SKI, TRK, ABL2, MYCN, RAB1, REL, RALB, LCO, ERBB4, RAF1, ECT2, KIT, FGF5, GRO1, GRO2, GRO3, FMS, PIM, KRAS1P, FYN, MYB, ROS1, MAS1, RALA, MYCLK1, GLI3, ARAF2, MET, BRAF, MOS, LYN, MYBL1, MYC, OVC, VAV2, BMI1, RET, HRAS, SPI1, RELA, SEA, EMS1, ETS1, KRAS2, ERBB3, GLI, FLT, BRCA2, RB1, FOS, AKT1, ELK2, FES, MAF, TP53, CRK, ERBA1, NF1, EVI2, ERBBB2, INT4, BRCA1, YES1, JUND, JUNB, MEL, LPSA, VAV1, AKT2, FOSB, RRAS, HKR1, HKR2, ERBAL2, SRC, MYBL2, ETS2, ERG, ARAF1, YUASA, HS2, INT3, SNO, RMYC, BMYC, HRASP, TC21, TIM, PTI-1, JAK, one or members of the CEA family (see, e.g., Zhou et al. (2001) *Gene* 264:105), PSA, MUC-16 and the like.

As used herein, the term "cancer" refers to various types of malignant neoplasms, most of which can invade surrounding tissues, and may metastasize to different sites (see, for example, *PDR Medical Dictionary,* 1st edition (1995), incorporated herein by reference in its entirety for all purposes). The terms "neoplasm" and "tumor" refer to an abnormal tissue that grows by cellular proliferation more rapidly than normal and continues to grow after the stimuli that initiated proliferation is removed. Id. Such abnormal tissue shows partial or complete lack of structural organization and functional coordination with the normal tissue which may be either benign (i.e., benign tumor) or malignant (i.e., malignant tumor).

Examples of general categories of cancer include, but are not limited to, carcinomas (i.e., malignant tumors derived from epithelial cells such as, for example, common forms of breast, prostate, lung and colon cancer), sarcomas (i.e., malignant tumors derived from connective tissue or mesenchymal cells), lymphomas (i.e., malignancies derived from hematopoietic cells), leukemias (i.e., malignancies derived from hematopoietic cells), germ cell tumors (i.e., tumors derived from totipotent cells. In adults most often found in the testicle or ovary; in fetuses, babies and young children, most often found on the body midline, particularly at the tip of the tailbone), blastic tumors (i.e., a typically malignant tumor which resembles an immature or embryonic tissue) and the like.

Examples of the types of neoplasms intended to be encompassed by the present invention include but are not limited to those neoplasms associated with cancers of neural tissue, blood forming tissue, breast, skin, bone, prostate, ovaries, uterus, cervix, liver, lung, brain, larynx, gallbladder, pancreas, rectum, parathyroid, thyroid, adrenal gland, immune system, head and neck, colon, stomach, bronchi, and/or kidneys.

In certain exemplary embodiments, one or more methods and/or compositions described herein are applied to detect, identify and/or diagnose disorders associated with the presence of fetal chromosomal abnormalities (e.g., Down's syndrome, autism and related autism spectrum disorders (including, but not limited to, Asperger's syndrome and pervasive developmental disorder—not otherwise specified), sickle cell anemia, thalassemia and the like) consequent to the presence of fetal cells and DNA within maternal blood. Screening and diagnosing of one or more of these disorders can be performed using the methods and/or compositions described herein to detect one or more chromosomal markers, e.g., DNA and RNA, and the like, within maternal blood phagocytic cells.

In certain exemplary embodiments, one or more methods and/or compositions described herein can be applied to test the gender of a fetus within a pregnant woman by detecting the presence of fetus-derived proteomic, lipidomic, and/or genomic signatures within blood of the pregnant woman, as fetal stem cells, nucleated erythrocytes, fetal lymphocytes, as well as significant amounts of cell-free fetal nucleic acids are known to circulate in maternal blood. According to the methods described herein, the cellular content and/or expression profile of phagocytic cells is compared to the cellular content and/or expression profile of non-phagocytic cells from the blood of a pregnant woman. Subtracting the cellular content and/or expression profile from non-phagocytic cells from that of phagocytic cells creates a cellular content and/or expression profile representative of the gender of the fetus being carried by the pregnant woman.

In certain exemplary embodiments, one or more methods and/or compositions described herein can be used to detect, identify and/or diagnose disorders associated with the presence of proteomic and/or genomic myocyte signatures within blood of subjects having or at risk of developing cardiac disease (e.g., myocardial infarction, chronic heart failure, ischemic heart disease, cardiovascular death and the like) by detecting the presence of dying/dead myocytes and/or fragments thereof (e.g., DNA, proteins and the like).

Screening and diagnosing of one or more of these disorders is performed using methods and/or compositions described herein to detect one or more markers, e.g., DNA and RNA, protein and the like, within blood phagocytic cells.

In certain exemplary embodiments, one or more methods and/or compositions described herein can be used to detect, identify and/or diagnose disorders associated with the presence of proteomic, lipidomic, and/or genomic signatures within blood of subjects having or at risk of developing atherosclerosis consequent to coronary artery narrowing, abdominal aortic aneurism, and the like. Screening and diagnosing of these disorders can performed using the methods and/or compositions described herein to detect one or more markers, e.g., DNA, RNA, protein and the like, within blood phagocytic cells.

Biopsy-confirmed rejection, one method for diagnosis of allograft rejection, is invasive and subject to sampling errors. Therefore, the development of noninvasive assays that detect molecular biomarkers for diagnosing and managing transplanted organ rejection is useful in management of transplant recipients by (a) detecting a pre-rejection profile that will allow therapeutic interventions before rejection causes graft dysfunction, (b) improving the sensitivity and specificity of rejection diagnosis, (c) developing new classification systems for rejection that will improve prognosis, and (d) providing information for designing individualized immunosuppressive regimens that could prevent rejection while minimizing drug toxicity.

Accordingly, in certain exemplary embodiments, one or more methods and/or compositions described herein can be used to detect, identify or diagnose disorders associated with the presence of proteomic, lipidomic, and genomic signatures within blood of subjects having undergone organ transplants by detecting one or more markers, e.g., DNA, RNA, protein or the like, within blood phagocytic cells.

Mitochondrial diseases result from failures of the mitochondria. Cell injury and even cell death follow. Diseases of the mitochondria appear to cause the most damage to cells of the brain, heart, liver, skeletal muscles, kidney and the endocrine and respiratory systems as well as diabetes, respiratory complications, seizures, Alzheimer's disease, visual/hearing problems, lactic acidosis, developmental delays, susceptibility to infection, and cancer.

Accordingly, in certain exemplary embodiments, one or more methods and/or compositions described herein can be used to screen, diagnose and/or detect mitochondrial disease, by detecting one or more genomic, mitochondria-associated DNA markers within blood phagocytic cells.

In certain exemplary embodiments, one or more methods and/or compositions described herein can be used to screen, diagnose and/or detect Alzheimer's disease and/or dementia by detecting one or more markers, e.g., DNA, RNA, protein and the like, within blood phagocytic cells.

Systemic lupus erythematosus (SLE) is a complex autoimmune disorder that affects various organs and systems. Accordingly, in certain exemplary embodiments, one or more methods and/or compositions described herein can be used to screen, diagnose and/or detect SLE by detecting one or more markers, e.g., DNA, RNA, lipids, protein and the like, within blood phagocytic cells.

In certain exemplary embodiments, one or more methods and/or compositions described herein can be used to screen and/or detect genomic and/or proteomic signatures useful in the development of therapeutic and/or imaging molecules by detecting one or more markers, e.g., DNA, RNA, protein and the like, within blood phagocytic cells.

In certain exemplary embodiments, one or more methods and/or compositions described herein can be used to screen, diagnose and/or detect alteration in genomic, proteomic and/or lipidomic signatures useful in detection of diseases and pathologies consequent to one or more external or internal insults (e.g., dirty bomb exposure, radiation exposure, chemical exposure, radiotherapy, radiopharmaceutical administration, therapeutic molecule exposure, radon exposure, asbestos exposure, pollution exposure and the like) by detecting one or more markers, e.g., DNA, RNA, protein, lipid and the like, within blood phagocytic cells.

As used herein, the term "organism" includes, but is not limited to, a human individual, a non-human primate, a cow, a horse, a sheep, a goat, a pig, a dog, a cat, a rabbit, a mouse, a rat, a gerbil, a frog, a toad and a transgenic species thereof. The term "organism" further includes pathogenic organisms, including, but not limited to, a pathogen such as a parasite, a yeast cell, a yeast tetrad, a yeast colony, a bacterium, a bacterial colony, a virion, a virosome, a virus-like particle and/or cultures of any of these, and the like.

In certain exemplary embodiments, the assays described herein can be used for the detection of an infectious agent and/or the diagnosis of a disorder associated with an infection of a cell, tissue, organ or the like by an infectious agent. In certain aspects, detection of an infectious agent and/or the diagnosis of a disorder associated with an infection is performed using the methods and/or compositions described herein to detect one or more infectious agent markers, e.g., DNA, RNA, proteins, lipids and the like, from one or more infectious agents.

As used herein, the term "infectious agent" includes, but is not limited to, pathogenic organisms such as viruses, bacteria, fungi, parasites, infectious proteins and the like.

Viruses include, but are not limited to, DNA or RNA animal viruses. As used herein, RNA viruses include, but are not limited to, virus families such as Picornaviridae (e.g., polioviruses), Reoviridae (e.g., rotaviruses), Togaviridae (e.g., encephalitis viruses, yellow fever virus, rubella virus), Orthomyxoviridae (e.g., influenza viruses), Paramyxoviridae (e.g., respiratory syncytial virus, measles virus, mumps virus, parainfluenza virus), Rhabdoviridae (e.g., rabies virus), Coronaviridae, Bunyaviridae, Flaviviridae, Filoviridae, Arenaviridae, Bunyaviridae and Retroviridae (e.g., human T cell lymphotropic viruses (HTLV), human immunodeficiency viruses (HIV)). As used herein, DNA viruses include, but are not limited to, virus families such as Papovaviridae (e.g., papilloma viruses), Adenoviridae (e.g., adenovirus), Herpesviridae (e.g., herpes simplex viruses), and Poxviridae (e.g., variola viruses).

Bacteria include, but are not limited to, gram positive bacteria, gram negative bacteria, acid-fast bacteria and the like.

As used herein, gram positive bacteria include, but are not limited to, *Actinomedurae, Actinomyces israelii, Bacillus anthracis, Bacillus cereus, Clostridium botulinum, Clostridium difficile, Clostridium perfringens, Clostridium tetani, Corynebacterium, Enterococcus faecalis, Listeria monocytogenes, Nocardia, Propionibacterium acnes, Staphylococcus aureus, Staphylococcus epiderm, Streptococcus mutans, Streptococcus pneumoniae* and the like.

As used herein, gram negative bacteria include, but are not limited to, *Afipia felis, Bacteroides, Bartonella bacilliformis, Bortadella pertussis, Borrelia burgdorferi, Borrelia recurrentis, Brucella, Calymmatobacterium granulomatis, Campylobacter, Escherichia coli, Francisella tularensis, Gardnerella vaginalis, Haemophilius aegyptius, Haemophilius ducreyi, Haemophilius influenziae, Heliobacter*

*pylori, Legionella pneumophila, Leptospira interrogans, Neisseria meningitidia, Porphyromonas gingivalis, Providencia sturti, Pseudomonas aeruginosa, Salmonella enteridis, Salmonella typhi, Serratia marcescens, Shigella boydii, Streptobacillus moniliformis, Streptococcus pyogenes, Treponema pallidum, Vibrio cholerae, Yersinia enterocolitica, Yersinia pestis* and the like.

As used herein, acid-fast bacteria include, but are not limited to, *Myobacterium avium, Myobacterium leprae, Myobacterium tuberculosis* and the like.

As used herein, other bacteria not falling into the other three categories include, but are not limited to, *Bartonella henseiae, Chlamydia psittaci, Chlamydia trachomatis, Coxiella burnetii, Mycoplasma pneumoniae, Rickettsia akari, Rickettsia prowazekii, Rickettsia rickettsii, Rickettsia tsutsugamushi, Rickettsia typhi, Ureaplasma urealyticum, Diplococcus pneumoniae, Ehrlichia chafensis, Enterococcus faecium, Meningococci* and the like.

As used herein, fungi include, but are not limited to, *Aspergilli, Candidae, Candida albicans, Coccidioides immitis, Cryptococci*, and combinations thereof.

As used herein, parasitic microbes include, but are not limited to, *Balantidium coli, Cryptosporidium parvum, Cyclospora cayatanensis, Encephalitozoa, Entamoeba histolytica, Enterocytozoon bieneusi, Giardia lamblia, Leishmaniae, Plasmodii, Toxoplasma gondii, Trypanosomae, trapezoidal amoeba* and the like.

As used herein, parasites include worms (e.g., helminthes), particularly parasitic worms including, but not limited to, Nematoda (roundworms, e.g., whipworms, hookworms, pinworms, ascarids, filarids and the like), Cestoda (e.g., tapeworms)

As used herein, infectious proteins include prions. Disorders caused by prions include, but are not limited to, human disorders such as Creutzfeldt-Jakob disease (CJD) (including, e.g., iatrogenic Creutzfeldt-Jakob disease (iCJD), variant Creutzfeldt-Jakob disease (vCJD), familial Creutzfeldt-Jakob disease (fCJD), and sporadic Creutzfeldt-Jakob disease (sCJD)), Gerstmann-Sträussler-Scheinker syndrome (GSS), fatal familial insomnia (fFI), sporadic fatal insomnia (sFI), kuru, and the like, as well as disorders in animals such as scrapie (sheep and goats), bovine spongiform encephalopathy (BSE) (cattle), transmissible mink encephalopathy (TME) (mink), chronic wasting disease (CWD) (elk, mule deer), feline spongiform encephalopathy (cats), exotic ungulate encephalopathy (EUE) (nyala, oryx, greater kudu), spongiform encephalopathy of the ostrich and the like.

In certain exemplary embodiments, methods of detecting markers such as nucleic acid sequences (e.g., DNA, RNA and the like), proteins, polypeptides, lipids polysaccharides and the like in a biological sample are provided. As used herein, the term "nucleic acid" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded.

As used herein, the term "amino acid" includes organic compounds containing both a basic amino group and an acidic carboxyl group. Included within this term are natural amino acids (e.g., L-amino acids), modified and unusual amino acids (e.g., D-amino acids and β-amino acids), as well as amino acids which are known to occur biologically in free or combined form but usually do not occur in proteins. Natural protein occurring amino acids include alanine, arginine, asparagine, aspartic acid, cysteine, glutamic acid, glutamine, glycine, histidine, isoleucine, leucine, lysine, methionine, phenylalanine, serine, threonine, tyrosine, tryptophan, proline, and valine. Natural non-protein amino acids include arginosuccinic acid, citrulline, cysteine sulfinic acid, 3,4-dihydroxyphenylalanine, homocysteine, homoserine, ornithine, 3-monoiodotyrosine, 3,5-diiodotryosine, 3,5,5,-triiodothyronine, and 3,3',5,5'-tetraiodothyronine. Modified or unusual amino acids include D-amino acids, hydroxylysine, 4-hydroxyproline, N-Cbz-protected amino acids, 2,4-diaminobutyric acid, homoarginine, norleucine, N-methylaminobutyric acid, naphthylalanine, phenylglycine, .alpha.-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

As used herein, the term "peptide" includes compounds that consist of two or more amino acids that are linked by means of a peptide bond. Peptides may have a molecular weight of less than 10,000 Daltons, less than 5,000 Daltons, or less than 2,500 Daltons. The term "peptide" also includes compounds containing both peptide and non-peptide components, such as pseudopeptide or peptidomimetic residues or other non-amino acid components. Such compounds containing both peptide and non-peptide components may also be referred to as a "peptide analog."

As used herein, the term "protein" includes compounds that consist of amino acids arranged in a linear chain and joined together by peptide bonds between the carboxyl and amino groups of adjacent amino acid residues.

As used herein, the term "lipid" includes synthetic or naturally-occurring compounds which are generally amphipathic and biocompatible. Lipids typically comprise a hydrophilic component and a hydrophobic component. Exemplary lipids include, but are not limited to fatty acids, neutral fats, phosphatides, glycolipids and the like. As used herein, the term "lipid composition" refers to a composition which comprises a lipid compound, typically in an aqueous medium. Exemplary lipid compositions include, but are not limited to, suspensions, emulsions, vesicle compositions and the like.

An exemplary method for detecting the presence or absence of a polypeptide or nucleic acid corresponding to a marker of the invention in a biological sample involves obtaining a biological sample (e.g., a bodily fluid sample (e.g., blood) and/or tumor sample) from a test subject and contacting the biological sample with a compound or an agent capable of detecting one or more markers (e.g., DNA, RNA, protein, polypeptide, carbohydrate, lipid or the like).

Detection methods described herein can be used to detect one or more markers (e.g., DNA, RNA, protein, polypeptide, carbohydrate, lipid or the like) in a biological sample in vitro as well as in vivo. For example, in vitro techniques for detection of mRNA include Northern hybridizations and in situ hybridizations. In vitro techniques for detection of a polypeptide corresponding to a marker of the invention include enzyme linked immunosorbent assays (ELISAs), Western blots, immunoprecipitations and immunofluorescence. In vitro techniques for detection of genomic DNA include Southern hybridizations. Furthermore, in vivo techniques for detection of a polypeptide corresponding to a marker of the invention include introducing into a subject a labeled antibody directed against the polypeptide. For example, the antibody can be labeled with a radioactive marker whose presence and location in a subject can be detected by standard imaging techniques.

Methods for analyzing lipid content in a biological sample are known in the art (See, e.g., Kang et al. (1992) *Biochim. Biophys. Acta.* 1128:267; Weylandt et al. (1996) *Lipids* 31:977; J. Schiller et al. (1999) *Anal. Biochem.* 267:46; Kang et al. (2001) *Proc. Natl. Acad. Sci. USA* 98:4050; Schiller et al. (2004) *Prog. Lipid Res.* 43:499). An exemplary method of lipid analysis is to extract lipids from a biological sample (e.g. using chloroform:methanol (2:1, vol:vol) containing 0.005% butylated hydroxytoluene (BHT, as an antioxidant)), prepare fatty acid methyl esters were (e.g., 14% BF3-methanol reagent), and quantifying the fatty acid methyl esters are quantified (e.g., by HPLC, TLC, by gas chromatography-mass spectroscopy using commercially available gas chromatographs, mass spectrometers, and/or combination gas chromatograph/mass spectrometers). Fatty acid mass is determined by comparing areas of various analyzed fatty acids to that of a fixed concentration of internal standard.

A general principle of diagnostic and prognostic assays involves preparing a sample or reaction mixture that may contain a marker (e.g., one or more of DNA, RNA, protein, polypeptide, carbohydrate, lipid and the like) and a probe under appropriate conditions and for a time sufficient to allow the marker and probe to interact and bind, thus forming a complex that can be removed and/or detected in the reaction mixture. These assays can be conducted in a variety of ways.

For example, one method to conduct such an assay would involve anchoring the marker or probe onto a solid phase support, also referred to as a substrate, and detecting target marker/probe complexes anchored on the solid phase at the end of the reaction. In one embodiment of such a method, a sample from a subject, which is to be assayed for presence and/or concentration of marker, can be anchored onto a carrier or solid phase support. In another embodiment, the reverse situation is possible, in which the probe can be anchored to a solid phase and a sample from a subject can be allowed to react as an unanchored component of the assay.

There are many established methods for anchoring assay components to a solid phase. These include, without limitation, marker or probe molecules which are immobilized through conjugation of biotin and streptavidin. Such biotinylated assay components can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored.

Other suitable carriers or solid phase supports for such assays include any material capable of binding the class of molecule to which the marker or probe belongs. Well known supports or carriers include, but are not limited to, glass, polystyrene, nylon, polypropylene, nylon, polyethylene, dextran, amylases, natural and modified celluloses, polyacrylamides, gabbros, and magnetite.

In order to conduct assays with the above mentioned approaches, the non-immobilized component is added to the solid phase upon which the second component is anchored. After the reaction is complete, uncomplexed components may be removed (e.g., by washing) under conditions such that any complexes formed will remain immobilized upon the solid phase. The detection of marker/probe complexes anchored to the solid phase can be accomplished in a number of methods outlined herein.

In certain exemplary embodiments, the probe, when it is the unanchored assay component, can be labeled for the purpose of detection and readout of the assay, either directly or indirectly, with detectable labels discussed herein and which are well-known to one skilled in the art.

It is also possible to directly detect marker/probe complex formation without further manipulation or labeling of either component (marker or probe), for example by utilizing the technique of fluorescence energy transfer (see, for example, U.S. Pat. Nos. 5,631,169 and 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determination of the ability of a probe to recognize a marker can be accomplished without labeling either assay component (probe or marker) by utilizing a technology such as real-time Biomolecular Interaction Analysis (BIA) (see, e.g., Sjolander, S. and Urbaniczky, C., 1991, *Anal. Chem.* 63:2338 2345 and Szabo et al., 1995, *Curr. Opin. Struct. Biol.* 5:699 705). As used herein, "BIA" or "surface plasmon resonance" is a technology for studying biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another embodiment, analogous diagnostic and prognostic assays can be conducted with marker and probe as solutes in a liquid phase. In such an assay, the complexed marker and probe are separated from uncomplexed components by any of a number of standard techniques, including but not limited to: differential centrifugation, chromatography, electrophoresis and immunoprecipitation. In differential centrifugation, marker/probe complexes may be separated from uncomplexed assay components through a series of centrifugal steps, due to the different sedimentation equilibria of complexes based on their different sizes and densities (see, for example, Rivas and Minton (1993) *Trends Biochem. Sci.* 18:284). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the marker/probe complex as compared to the uncomplexed components may be exploited to differentiate the complex from uncomplexed components, for example through the utilization of ion-exchange chromatography resins. Such resins and chromatographic techniques are well known to one skilled in the art (see, e.g., Heegaard (1998) *J. Mol. Recognit.* 11:141; Hage and Tweed (1997) *J. Chromatogr. B. Biomed. Sci. Appl.* 12:499). Gel electrophoresis may also be employed to separate complexed assay components from unbound components (see, e.g., Ausubel et al., ed., *Current Protocols in Molecular Biology*, John Wiley & Sons, New York, 1987 1999). In this technique, protein or nucleic acid complexes are separated based on size or charge, for example. In order to maintain the binding interaction during the electrophoretic process, non-denaturing gel matrix materials and conditions in the absence of reducing agent are typically preferred. Appropriate conditions to the particular assay and components thereof will be well known to one skilled in the art.

In certain exemplary embodiments, the level of mRNA corresponding to the marker can be determined either by in situ and/or by in vitro formats in a biological sample using methods known in the art. Many expression detection methods use isolated RNA. For in vitro methods, any RNA isolation technique that does not select against the isolation of mRNA can be utilized for the purification of RNA from blood cells (see, e.g., Ausubel et al, ed., *Current Protocols in Molecular Biology*, John Wiley & Sons, New York 1987 1999). Additionally, large numbers of cells and/or samples can readily be processed using techniques well known to those of skill in the art, such as, for example, the single-step RNA isolation process of Chomczynski (1989, U.S. Pat. No. 4,843,155).

Isolated mRNA can be used in hybridization or amplification assays that include, but are not limited to, Southern or Northern analyses, polymerase chain reaction analyses and probe arrays. In certain exemplary embodiments, a diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to an mRNA or genomic DNA encoding a marker of the present invention. Other suitable probes for use in the diagnostic assays of the invention are described herein. Hybridization of an mRNA with the probe indicates that the marker in question is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in a gene chip array. A skilled artisan can readily adapt known mRNA detection methods for use in detecting the level of mRNA encoded by the markers of the present invention.

An alternative method for determining the level of mRNA corresponding to a marker of the present invention in a sample involves the process of nucleic acid amplification, e.g., by rtPCR (the experimental embodiment set forth in U.S. Pat. Nos. 4,683,195 and 4,683,202), COLD-PCR (Li et al. (2008) *Nat. Med.* 14:579), ligase chain reaction (Barany, 1991, *Proc. Natl. Acad. Sci. USA,* 88:189), self sustained sequence replication (Guatelli et al., 1990, *Proc. Natl. Acad. Sci. USA* 87:1874), transcriptional amplification system (Kwoh et al. (1989) *Proc. Natl. Acad. Sci. USA* 86:1173), Q-Beta Replicase (Lizardi et al. (1988) *Bio/Technology* 6:1197), rolling circle replication (U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the sample (e.g., a bodily fluid (e.g., blood cells)) prior to detection. In such methods, a cell or tissue sample is prepared/processed using known histological methods. The sample is then immobilized on a support, typically a glass slide, and then contacted with a probe that can hybridize to mRNA that encodes the marker.

As an alternative to making determinations based on the absolute expression level of the marker, determinations may be based on the normalized expression level of the marker. Expression levels are normalized by correcting the absolute expression level of a marker by comparing its expression to the expression of a gene that is not a marker, e.g., a housekeeping gene that is constitutively expressed. Suitable genes for normalization include housekeeping genes such as the actin gene, or epithelial cell-specific genes. This normalization allows the comparison of the expression level in a patient sample from one source to a patient sample from another source, e.g., to compare a phagocytic blood cell from an individual to a non-phagocytic blood cell from the individual.

In another exemplary embodiment, a protein or polypeptide corresponding to a marker is detected. In certain exemplary embodiments, an agent for detecting a polypeptide of the invention is an antibody capable of binding to a polypeptide corresponding to a marker of the invention, such as an antibody with a detectable label. Antibodies can be polyclonal, or more preferably, monoclonal. An intact antibody, or a fragment thereof (e.g., Fab or $F(ab')_2$) can be used. The term "labeled," with respect to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

A variety of formats can be employed to determine whether a sample contains a protein that binds to a given antibody. Examples of such formats include, but are not limited to, enzyme immunoassay (EIA), radioimmunoassay (RIA), Western blot analysis, enzyme linked immunoabsorbant assay (ELISA) and the like. A skilled artisan can readily adapt known protein/antibody detection methods for use in determining whether cells (e.g., bodily fluid cells such as blood cells) express a marker of the present invention.

In one format, antibodies, or antibody fragments, can be used in methods such as Western blots or immunofluorescence techniques to detect the expressed proteins. In such uses, it is generally preferable to immobilize either the antibody or proteins on a solid support. Suitable solid phase supports or carriers include any support capable of binding an antigen or an antibody. Well known supports or carriers include glass, polystyrene, polypropylene, polyethylene, dextran, nylon, amylases, natural and modified celluloses, polyacrylamides, gabbros, magnetite and the like.

One skilled in the art will know many other suitable carriers for binding antibody or antigen, and will be able to adapt such support for use with the present invention. For example, protein isolated from cells (e.g., bodily fluid cells such as blood cells) can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

In certain exemplary embodiments, diagnostic assays are provided. An exemplary method for detecting the presence or absence of a bodily condition, a disease and/or disorder associated with cancer, an infectious agent, and/or another disease in a biological sample involves obtaining a biological sample from a test subject and contacting the biological sample with a compound or an agent capable of detecting one or more of the markers of a disease and/or disorder associated with cancer, an infectious agent, and/or another disease or condition, e.g., marker nucleic acid (e.g., mRNA, genomic DNA), marker peptide (e.g., polypeptide or protein) or marker lipid encoded by the marker nucleic acid such that the presence of a marker nucleic acid or marker peptide encoded by the nucleic acid is detected in the biological sample. In one embodiment, an agent for detecting marker mRNA or genomic DNA is a labeled nucleic acid probe capable of hybridizing to marker mRNA or genomic DNA. The nucleic acid probe can be, for example, a full-length marker nucleic acid or a portion thereof. Other suitable probes for use in the diagnostic assays of the invention are described herein.

An agent for detecting marker peptide can be an antibody capable of binding to a marker peptide, such as an antibody with a detectable label. Antibodies can be polyclonal or monoclonal. An intact antibody, or a fragment thereof (e.g., Fab or F(ab')$_2$) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

As used herein, the term "biological sample" is intended to include tissues, cells (e.g., phagocytic cells, non-phagocytic cells, 2n cells, >2n cells and the like) and biological fluids (e.g., whole blood, WBCs and the like) isolated from a subject, as well as tissues, cells (e.g., phagocytic cells, non-phagocytic cells, 2n cells, >2n cells and the like) and bodily fluids (e.g., urine, whole blood, WBCs and the like) present within a subject. That is, the detection method of the invention can be used to detect marker polypeptide, protein, carbohydrate, lipid, oligosaccharide, mRNA, microRNA, genomic DNA and the like in a biological sample in vitro as well as in vivo. In one embodiment, the biological sample contains proteins, polypeptides, lipids and/or oligosaccharides from the test subject. Alternatively, the biological sample can contain mRNA molecules from the test subject and/or genomic DNA molecules from the test subject. In one embodiment biological sample is a serum sample, saliva sample or a biopsy sample isolated by conventional means from a subject.

In another embodiment, the methods further involve obtaining a control biological sample from a control subject (e.g., non-phagocytic cell or 2n cell), contacting the control sample (e.g., non-phagocytic cell or 2n cell) with a compound or agent capable of detecting marker polypeptide, protein lipid, oligosaccharide, mRNA, microRNA, genomic DNA and the like is detected in the biological sample, and comparing the presence of marker polypeptide, protein lipid, oligosaccharide, mRNA, genomic DNA and the like in control sample with the presence of marker polypeptide, protein lipid, oligosaccharide, mRNA, genomic DNA and the like in the test sample (e.g., phagocytic cell or >2n cell). Alternatively, the presence of marker polypeptide, protein lipid, oligosaccharide, mRNA, genomic DNA and the like in the test sample (e.g., phagocytic cell or >2n cell) can be compared with information in a database or on a chart to result in detection or diagnosis.

The invention also encompasses kits for detecting the presence of one or more markers associated with cancer and/or an infectious agent in a biological sample. For example, the kit can comprise a labeled compound or agent capable of detecting marker polypeptide, protein lipid, oligosaccharide, mRNA, microRNA, genomic DNA and the like in a biological sample; means for determining the amount of marker in the sample; and means for comparing the amount of marker in the sample with a standard (e.g., a non-phagocytic cell or a 2n cell). The compound or agent can be packaged in a suitable container. The kit can further comprise instructions for using the kit to detect marker peptide or nucleic acid.

In certain exemplary embodiments, prognostic assays are provided. The diagnostic methods described herein can furthermore be utilized to identify subjects having a condition or at risk of developing a disease and/or disorder associated with cancer and/or an infectious agent, or another disorder described herein associated with upregulated (or downregulated) expression of one or more of the markers described herein. For example, the assays described herein, such as the preceding diagnostic assays or the following assays, can be utilized to identify a subject having or at risk of developing a disease and/or disorder associated with cancer and/or an infectious agent and/or one or more other disorders described herein.

The prognostic assays described herein can be used to determine whether a subject can be administered an agent (e.g., an agonist, antagonist, peptidomimetic, protein, peptide, nucleic acid, small molecule, or other drug candidate) to treat a disease and/or disorder associated with cancer and/or an infectious agent, and/or one or more other disorders described herein associated with one or more of the markers described herein. For example, such methods can be used to determine whether a subject can be effectively treated with an agent for treating, ameliorating or reducing one or more symptoms associated with cancer. Thus, the present invention provides methods for determining whether a subject can be effectively treated with an agent for a disease and/or disorder associated with cancer and/or an infectious agent, and/or one or more other disorders described herein.

The methods of the invention can also be used to detect genetic alterations in a marker gene, thereby determining if a subject with the altered gene is at risk for developing a disease and/or disorder associated with cancer and/or an infectious agent, and/or one or more other disorders described herein characterized by misregulation in a marker protein activity or nucleic acid expression, such as cancer. In certain embodiments, the methods include detecting, in a sample of cells (e.g., bodily fluid cells such as blood cells) from the subject, the presence or absence of a genetic alteration characterized by an alteration affecting the integrity of a gene encoding a marker peptide and/or a marker gene. For example, such genetic alterations can be detected by ascertaining the existence of at least one of: 1) a deletion of one or more nucleotides from one or more marker genes; 2) an addition of one or more nucleotides to one or more marker genes; 3) a substitution of one or more nucleotides of one or more marker genes, 4) a chromosomal rearrangement of one or more marker genes; 5) an alteration in the level of a messenger RNA transcript of one or more marker genes; 6) aberrant modification of one or more marker genes, such as of the methylation pattern of the genomic DNA; 7) the presence of a non-wild type splicing pattern of a messenger RNA transcript of one or more marker genes; 8) a non-wild type level of a one or more marker proteins; 9) allelic loss of one or more marker genes; and 10) inappropriate post-translational modification of one or more marker proteins. As described herein, there are a large number of assays known in the art which can be used for detecting alterations in one or more marker genes.

In certain embodiments, detection of the alteration involves the use of a probe/primer in a polymerase chain reaction (PCR) (see, e.g., U.S. Pat. Nos. 4,683,195, 4,683,202 and 5,854,033), such as real-time PCR, COLD-PCR, anchor PCR, recursive PCR or RACE PCR, or, alternatively, in a ligation chain reaction (LCR) (see, e.g., Landegran et al. (1988) *Science* 241:1077; Prodromou and Pearl (1992) *Protein Eng.* 5:827; and Nakazawa et al. (1994) *Proc. Natl. Acad. Sci. USA* 91:360), the latter of which can be particularly useful for detecting point mutations in a marker gene (see Abravaya et al. (1995) *Nucleic Acids Res.* 23:675). This method can include the steps of collecting a sample of cells from a subject, isolating nucleic acid (e.g., genomic, mRNA or both) from the cells of the sample, contacting the nucleic acid sample with one or more primers which specifically hybridize to a marker gene under conditions such that hybridization and amplification of the marker gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al., (1990) *Proc. Natl. Acad. Sci. USA* 87:1874), transcriptional amplification system (Kwoh et al., (1989) *Proc. Natl. Acad. Sci. USA* 86:1173), Q-Beta Replicase (Lizardi et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in one or more marker genes from a sample cell can be identified by alterations in restriction enzyme cleavage patterns. For example, sample and control DNA is isolated, optionally amplified, digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in one or more of the markers described herein can be identified by hybridizing a sample and control nucleic acids, e.g., DNA or RNA, to high density arrays containing hundreds or thousands of oligonucleotides probes (Cronin et al. (1996) *Human Mutation* 7: 244; Kozal et al. (1996) *Nature Medicine* 2:753). For example, genetic mutations in a marker nucleic acid can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence a marker gene and detect mutations by comparing the sequence of the sample marker gene with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) Biotechniques 19:448), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147).

Other methods for detecting mutations in a marker gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes formed by hybridizing (labeled) RNA or DNA containing the wild-type marker sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl. Acad. Sci. USA* 85:4397; Saleeba et al. (1992) *Methods Enzymol.* 217:286. In one embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in marker cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657). According to an exemplary embodiment, a probe based on a marker sequence, e.g., a wild-type marker sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in marker genes. For example, single strand conformation polymorphism (SSCP) may be used to detect differences in electrophoretic mobility between mutant and wild type nucleic acids (Orita et al. (1989) *Proc. Natl. Acad. Sci. USA* 86:2766, see also Cotton (1993) *Mutat. Res.* 285:125; and Hayashi (1992) *Genet. Anal. Tech. Appl.* 9:73). Single-stranded DNA fragments of sample and control marker nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility (Keen et al. (1991) *Trends Genet.* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163; Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucl. Acids Res.* 17:2437) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci. USA* 88:189). In such cases, ligation will occur only if there is a perfect match at the 3' end of the 5' sequence making it possible to detect the presence of a known mutation at a specific site by looking for the presence or absence of amplification.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention. The contents of all references, patents and published patent applications cited throughout this application are hereby incorporated by reference in their entirety for all purposes.

The following examples are set forth as being representative of the present invention. These examples are not to be construed as limiting the scope of the invention as these and other equivalent embodiments will be apparent in view of the present disclosure, figures, and accompanying claims.

EXAMPLE 1

Representative Method I for the Separation of Phagocytic Cells from Non-Phagocytic Cells and the Analysis of Expression Profiles 1. With reference to FIGS. 2 and 3, coat plates with avidin.

2. Add biotinylated antibody to non-phagocytic blood cell (e.g., T cells) to the wells, incubate for 30 min at RT, wash wells.

3. Add magnetic beads.

4. Add WBC blood sample.

5. Incubate at 37° C. (30 minutes-1 hour).

6. Following phagocytosis of beads by phagocytic cells and binding of avidin-biotin-antibody to non-phagocytic cells, place plate on top of magnet and wash (the phagocytic cells that internalized the magnetic beads and the non-phagocytic cells bound to the antibody will stay; all other cells will be washed away).

7. Remove magnet and collect phagocytic cells.

8. Isolate RNA from phagocytic cells (e.g., cells bound to a magnetic bead) and of non-phagocytic cells (e.g., those cells attached to the bottom of the wells via the anti-non-phagocytic cell biotinylated antibody-avidin bound), prepare cDNA, cRNA and use to differentiate genetic profiles (e.g., whole gene arrays and/or cancer gene arrays) of phagocytic and non-phagocytic cells.

9. Isolate DNA from each cell sample and identify tumor-DNA signatures selectively present in phagocytes (i.e., absent in non-phagocytes); compare the profiles (e.g., whole gene arrays, DNA mutations and/or SNPs obtained in phagocytic and non-phagocytic cells).

10. Isolate protein from each cell sample, run Western blots using antibodies to known proteins overexpressed by human tumors (e.g., PSA and PSMA in prostate cancer; CEA in colon cancer; and CA125 in ovarian cancer), and compare the profiles obtained in phagocytic and non-phagocytic cells. Alternatively, use mass spectroscopy to identify the proteins.

11. Isolate lipids from each cell sample and compare quantity and quality, for example using HPLC.

EXAMPLE 2

Representative Method II for the Separation of Phagocytic Cells from Non-Phagocytic Cells and the Analysis of Expression Profiles 1. With reference to FIGS. 2 and 3, lyse RBCs in blood sample.
2. Cytospin WBC on glass slides.
3. Fix cells in acetone/methanol (−20° C. for 5 minutes).
4. Stain with hematoxylin and eosin stain and anti-T cell antibody.
5. Isolate T cells (non-phagocytic) and macrophages (phagocytic) using laser capture microscopy (LCM).
6. Isolate RNA from phagocytic cells and of non-phagocytic cells, prepare cDNA, cRNA and use to differentiate genetic profiles (e.g., whole gene arrays and/or cancer gene arrays) of phagocytic and non-phagocytic cells.
7. Isolate DNA from each cell sample, run DNA arrays, and compare the profiles (e.g., whole gene arrays, DNA mutations and/or SNPs) obtained in phagocytic and non-phagocytic cells.
8. Isolate protein from each cell sample, run Western blots using antibodies to known proteins overexpressed by human tumors (e.g., PSA and PSMA in prostate cancer; CEA in colon cancer; and CA125 in ovarian cancer), and compare the profiles obtained in phagocytic and non-phagocytic cells. Alternatively, use mass spectroscopy to identify the proteins.
9. Isolate lipids from each cell sample and compare quantity and quality, for example using HPLC.

EXAMPLE 3

Representative Method III for the Separation of Phagocytic Cells from Non-Phagocytic Cells and the Analysis of Expression Profiles 1. With reference to FIGS. 2 and 3, lyse RBC from a blood sample.
2. Use magnetic antibody-conjugated beads to isolate non-phagocytic (e.g., T cells) and phagocytic cells (e.g., neutrophils and/or macrophages and/or monocytes) from whole blood.
3. Isolate RNA from each cell sample, prepare cDNA, cRNA and use to differentiate genetic profiles (e.g., cancer gene array) of phagocytic and non-phagocytic cells.
4. Isolate DNA from each cell sample, run DNA arrays, and compare the profiles obtained in phagocytic and non-phagocytic cells.
5. Isolate protein from each cell sample, run Western blots using antibodies to known proteins overexpressed by human tumors (e.g., PSA and PSMA in prostate cancer; CEA in colon cancer; and CA125 in ovarian cancer), and compare the profiles obtained in phagocytic and non-phagocytic cells. Alternatively, use mass spectroscopy to identify the proteins.
6. Isolate lipids from each cell sample and compare quantity and quality, for example using HPLC.

EXAMPLE 4

Representative Method IV for the Separation of Phagocytic Cells from Non-Phagocytic Cells and the Analysis of Expression Profiles 1. With reference to FIGS. 2 and 3, stain WBC with fluorescent antibodies specific against a particular cell subpopulation (e.g., neutrophils, macrophages, monocytes, T cells and the like).
2. Sort the cells (e.g., by FACS).
3. Isolate RNA from each cell sample, prepare cDNA, cRNA and use to differentiate genetic profiles (e.g., cancer gene array) of phagocytic and non-phagocytic cells.
4. Isolate DNA from each cell sample, run DNA arrays, and compare the profiles obtained in phagocytic and non-phagocytic cells.
5. Isolate protein from each cell sample, run Western blots using antibodies to known proteins overexpressed by human tumors (e.g., PSA and PSMA in prostate cancer; CEA in colon cancer; and CA125 in ovarian cancer), and compare the profiles obtained in phagocytic and non-phagocytic cells. Alternatively, use mass spectroscopy to identify the proteins.
6. Isolate lipids from each cell sample and compare quantity and quality, for example using HPLC.

EXAMPLE 5

Representative Method V for the Separation of Phagocytic Cells from Non-Phagocytic Cells and the Analysis of Expression Profiles 1. With reference to FIGS. 5 and 6, stain WBC with fluorescent antibodies to each cell subpopulation (e.g., neutrophils, macrophages, monocytes, and T cells), and then stain with DNA dye (e.g., propidium iodide).
2. Sort the cells (FACS) into T cells, neutrophils (2n), neutrophils (>2n), macrophages (2n), macrophages (>2n), monocytes (2n), and monocytes (>2n).
3. Isolate RNA from T cells, neutrophils (>2n), macrophages (>2n), and monocytes (>2n). Then prepare cDNA, cRNA and use to differentiate genetic profiles (e.g., cancer gene array) of phagocytic and non-phagocytic cells.
4. Isolate DNA from T cells, neutrophils (>2n), macrophages (>2n), and monocytes (>2n). Run DNA arrays and compare the profiles obtained in phagocytic and non-phagocytic cells.
5. Isolate protein from T cells, neutrophils (>2n), macrophages (>2n), and monocytes (>2n). Run Western blots using antibodies to known proteins overexpressed by human tumors (e.g., PSA and PSMA in prostate cancer; CEA in colon cancer; and CA125 in ovarian cancer), and compare the profiles obtained in phagocytic and non-phagocytic cells. Alternatively, use mass spectroscopy to identify the proteins.
6. Isolate lipids from T cells, neutrophils (>2n), macrophages (>2n), and monocytes (>2n). Compare quantity and quality of lipids, for example using HPLC

EXAMPLE 6

Representative Method VI for the Separation of Phagocytic Cells and the Analysis of Expression Profiles 1. With reference to FIGS. 5 and 6, stain WBC with fluorescent antibodies specific against one or more phagocytic cells (e.g., neutrophils, macrophages, or monocytes) and then stain with DNA-binding dye (e.g., propidium iodide).
2. Sort the cells (FACS) into 2n and >2n phagocytes.
3. Isolate RNA from each of the 2n and >2n phagocytes. Prepare cDNA, cRNA and use to differentiate genetic profiles (e.g., cancer gene array) of 2n-phagocytic and >2n-phagocytic cells.
4. Isolate DNA from each of the 2n and >2n phagocytes. Run DNA arrays and compare the profiles obtained from 2n-phagocytic and >2n-phagocytic cells.
5. Isolate protein from each of the 2n and >2n phagocytes. Run Western blots using antibodies to known proteins overexpressed by human tumors (e.g., PSA and PSMA in prostate cancer; CEA in colon cancer; and CA125 in ovarian cancer), and compare the profiles obtained from 2n-phagocytic and >2n-phagocytic cells.
6. Isolate lipids from each of the 2n and >2n phagocytes. Compare quantity and quality of lipids, for example using HPLC.

EXAMPLE 7

Detection of Tumor-Specific Gene Signatures in Phagocytes Obtained from Tumor-Bearing Mice According to embodiments of the present invention, methods are provided to differentiate between "normal non-specific noise" and "tumor-specific" and/or "disease-specific" signatures in blood or other bodily fluids. The gene-expression profiles of blood monocytes/macrophages and neutrophils from tumor-bearing mice were compared with that of non-phagocytic T cells from the same donor mice to identify tumor-specific signatures within the phagocytic cells that were either not expressed or significantly differentially expressed in non-phagocytic cells from the same tumor-bearing mice and from non-tumor-bearing animals.

Human Prostate LNCaP Cancer Cells

Athymic nude mice (n=5) were injected subcutaneously (s.c.) with human prostate LNCaP cancer cells. Twenty-seven days later (tumor size=~0.4 cm), the mice were bled by cardiac puncture (~1 mL/mouse) into EDTA-containing tubes that were then centrifuged. The buffy coat was isolated and washed, and neutrophils, macrophages, and T cells were separated using, respectively, anti-mouse neutrophil-, macrophage-, and T cell-immunomagnetic DynaBeads. RNA was isolated from each cell sample)(Triazol®. The RNA quality was determined as shown in FIG. 3. The RNA yield is shown in FIG. 20. cDNA and biotinylated cRNA (cRNA-B) were prepared. Finally, the cRNA-B samples were incubated with cancer-gene human microarrays (Oligo GEArray® Human Cancer PathwayFinder Microarray—OHS-033—SuperArray Bioscience). Following hybridization, the membranes were washed and stained with avidin-alkaline phosphatase, and the genes were detected using chemiluminescence (X-ray film).

Human LS174T Colon Adenocarcinoma Tumors, LLC1 Carcinoma Cells, B16F10 Mouse Melanoma Cells Similar experiments were carried out with cells isolated from athymic nude mice (n=5) injected s.c. with human LS174T colon adenocarcinoma tumors (tumor size=~0.3 cm), C57Bl mice (n=5) injected s.c. with Lewis lung mouse LLC1 carcinoma cells (tumor size=~0.6 cm), and C57Bl mice (n=5) injected intravenously 22 days earlier with $10^6$ B16F10 mouse melanoma cells (when the tumor cells were of mouse origin, the cRNA-B samples were hybridized with the Oligo GEArray® Mouse Cancer PathwayFinder Microarray—OMM-033—SuperArray Bioscience). RNA was also isolated from exponentially growing LS174T, LLC1, B16F10, and LNCaP cells in culture and from neutrophils, macrophages and T cells isolated from non-tumor-bearing C57Bl and nude mice, and their cancer-related gene profiles were determined.

According to the data obtained from these experiments and shown in FIGS. 9-17, neutrophils and macrophages—obtained from mice injected with human prostate or colon tumor cells and from mice bearing mouse lung cancer or melanoma—have various cancer-related gene signatures that are also found in their respective tumor cells. These cancer-related genes were not expressed or were minimally expressed by (i) non-phagocytic T cells isolated from tumor-bearing mice; and (ii) phagocytic neutrophils and macrophages obtained from non-tumor-bearing mice.

Figure 9A:
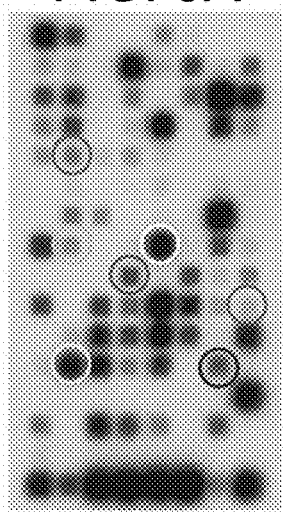
FIGS. 9A-9D depict arrays showing seven up-regulated ($\geq 2$ fold), cancer related genes detected in neutrophils from LNCaP (human prostate cancer) tumor-bearing nude mice. (A) LNCaP tumor. (B) Neutrophils obtained from nude mice bearing LNCaP tumors ($N_T$). (C) T cells obtained from nude mice bearing LNCaP tumors ($T_T$). (D) Neutrophils obtained from non-tumor-bearing nude mice ($N_N$). Circled signatures expressed in tumor cells (A) and in neutrophils from tumor-bearing mice (B), and minimally expressed in neutrophils from non-tumor-bearing mice (D), and in non-phagocytic T cells (C). Expression in $N_T$ was $\geq 2$-fold than that in $N_N$ and $T_T$.
Figure 9B:
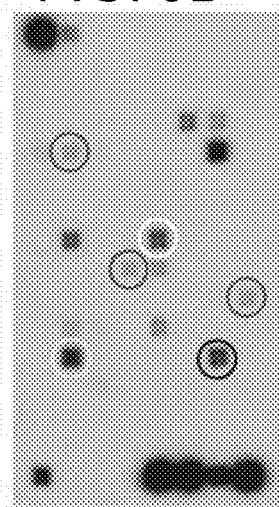
Figure 9C:
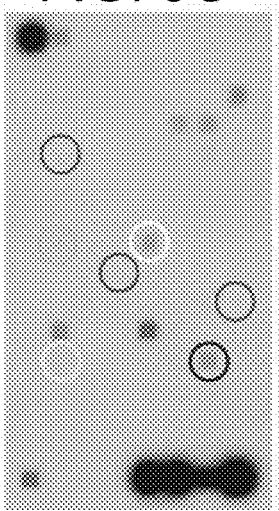
Figure 9D:
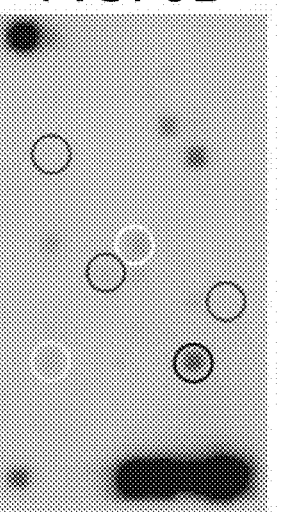
Figure 10A:
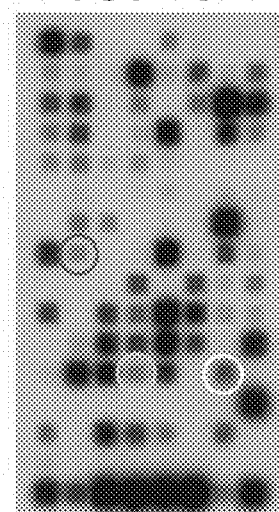
FIGS. 10A-10D depict arrays showing three up-regulated, cancer related genes detected in macrophages from LNCaP (human prostate cancer) tumor-bearing nude mice. (A) LNCaP tumor. (B) macrophages obtained from nude mice bearing LNCaP tumors ($M_T$). (C) T cells obtained from nude mice bearing LNCaP tumors ($T_T$). (D) macrophages obtained from non-tumor-bearing nude mice ($M_N$). Circled signatures expressed in tumor cells (A) and in macrophages from tumor-bearing mice (B), and minimally expressed in macrophages from non-tumor-bearing mice (D), and in non-phagocytic T cells (C). Expression in $M_T$ was $\geq 2$-fold than that in $M_N$ and $T_T$.
Figure 10B:
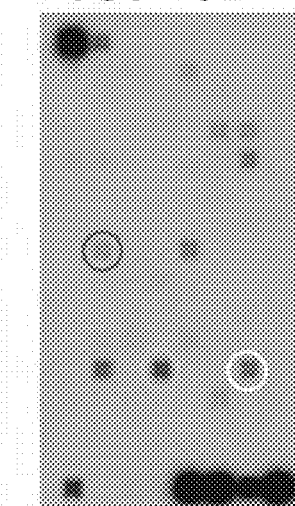
Figure 10C:
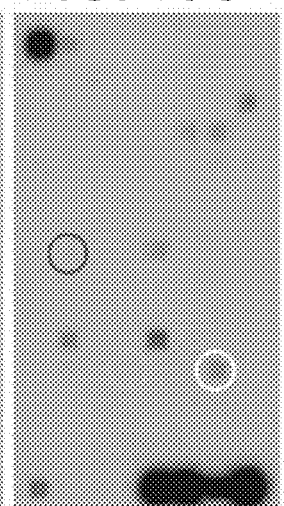
Figure 10D:
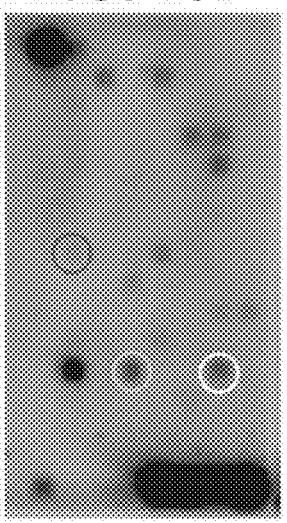
Figure 11A:
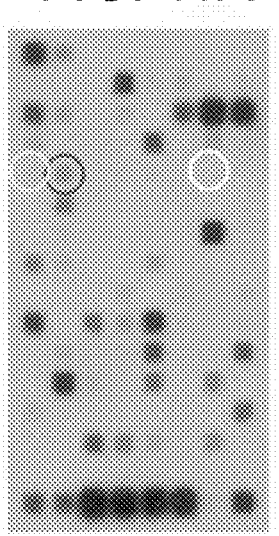
FIGS. 11A-11D depict arrays showing four up-regulated ($\geq 2$ fold), cancer related genes detected in neutrophils from LS174T (human colon cancer) tumor-bearing nude mice. (A) LS174T tumor. (B) Neutrophils obtained from nude mice bearing LS174T tumors ($N_T$). (C) T cells obtained from nude mice bearing LS174T tumors ($T_T$). (D) Neutrophils obtained from non-tumor-bearing nude mice ($N_N$). Circled signatures expressed in tumor cells (A) and in neutrophils from tumor-bearing mice (B), and minimally expressed in neutrophils from non-tumor-bearing mice (D), and in non-phagocytic T cells (C). Expression was $N_T$ is $\geq 2$-fold than that in $N_N$ and $T_T$.
Figure 11B:
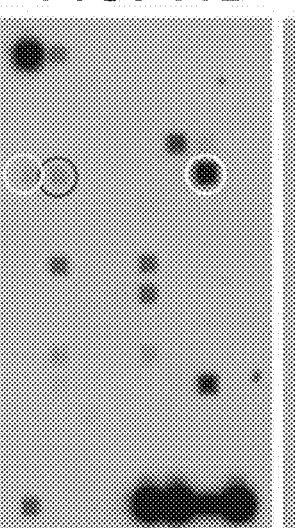
Figure 11C:
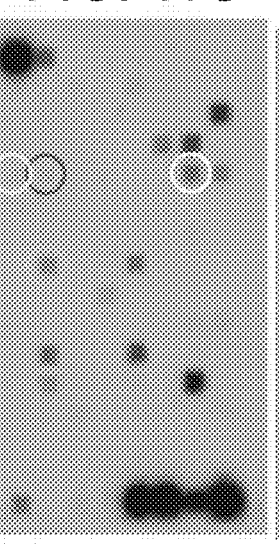
Figure 11D:
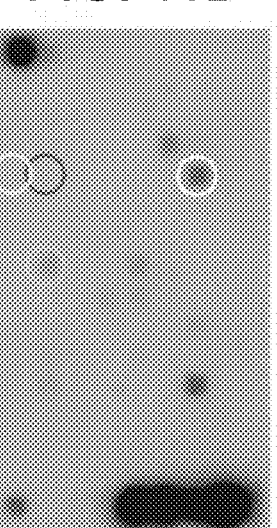
Figure 12A:
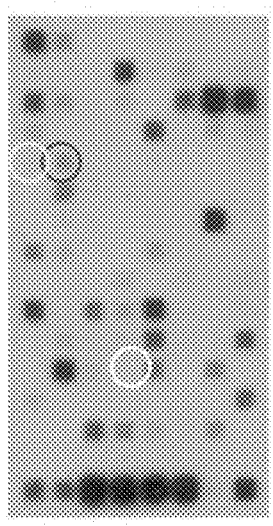
FIGS. 12A-12D depict arrays showing three up-regulated ($\geq 2$ fold), cancer related genes detected in macrophages from LS174T (human colon cancer) tumor-bearing nude mice. (A) LS174T tumor. (B) Macrophages obtained from nude mice bearing LS174T tumors ($M_T$). (C) T cells obtained from nude mice bearing LS174T tumors ($T_T$). (D) Macrophages obtained from non-tumor-bearing nude mice ($M_N$). Circled signatures expressed in tumor cells (A) and in macrophages from tumor-bearing mice (B), and minimally expressed in macrophages from non-tumor-bearing mice (D), and in non-phagocytic T cells (C). Expression in $M_T$ is ≥2-fold than that in $M_N$ and $T_T$.
Figure 12B:
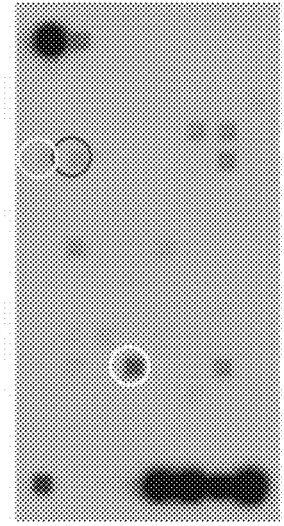
Figure 12C:
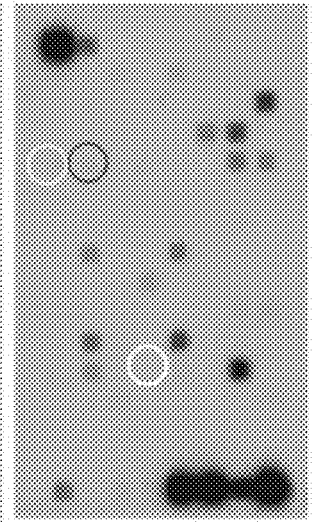
Figure 12D:
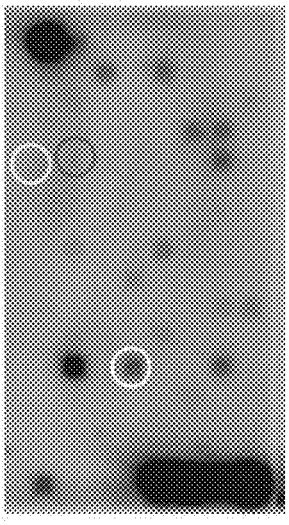

For example, neutrophils isolated from the blood of nude mice bearing LNCaP human prostate cancer cells expressed several human tumor gene signatures (Human Cancer PathwayFinder Microarray) that were also expressed in LNCaP cells (compare profiles of arrays in FIGS. 9A and 9B). These genes were either not expressed or minimally expressed in T cells obtained from tumor-bearing mice or neutrophils isolated from normal mice (see profiles in FIGS. 9C and 9D). Similarly, neutrophils isolated from the blood of mice bearing LLC1 mouse lung cancer cells expressed several mouse tumor gene signatures (Mouse Cancer PathwayFinder Microarray) that were expressed in LLC1 cells (compare profiles of arrays in FIGS. 13A and 13B).

Figure 13A:
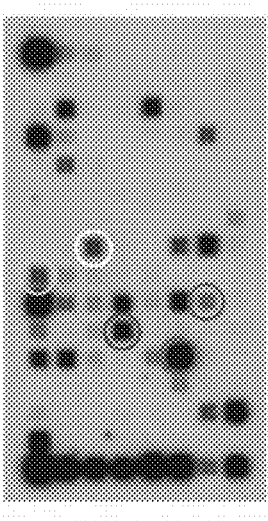
FIGS. 13A-13D depict arrays showing five up-regulated (≥2 fold), cancer related genes detected in neutrophils from LLC1 (mouse metastatic lung cancer) tumor-bearing C57/Bl mice. (A) LLC1 tumor. (B) Neutrophils obtained from C57/Bl mice bearing LLC1 tumors ($N_T$). (C) T cells obtained from C57/Bl mice bearing LLC1 tumors ($T_T$). (D) Neutrophils obtained from non-tumor-bearing C57/Bl mice ($N_N$). Circled signatures expressed in tumor cells (A) and in neutrophils from tumor-bearing mice (B), and minimally expressed in neutrophils from non-tumor-bearing mice (D), and in non-phagocytic T cells (C). Expression in $N_T$ was ≥2-fold than that in $N_N$ and $T_T$.
Figure 13B:
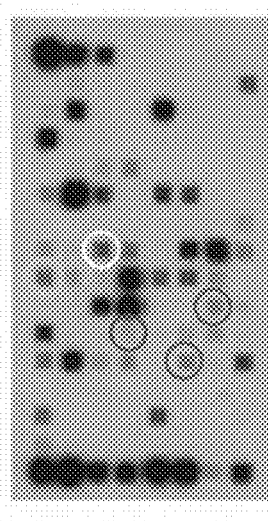
Figure 13C:
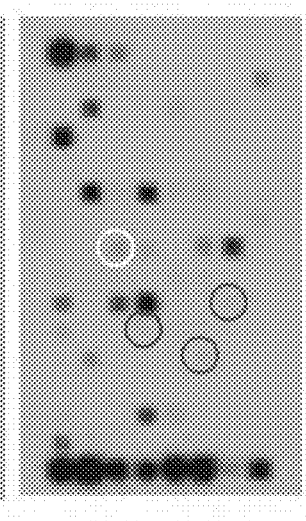
Figure 13D:
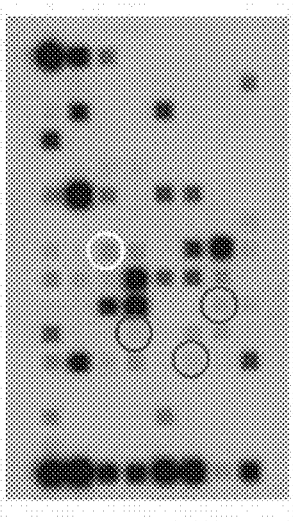
Figure 14A:
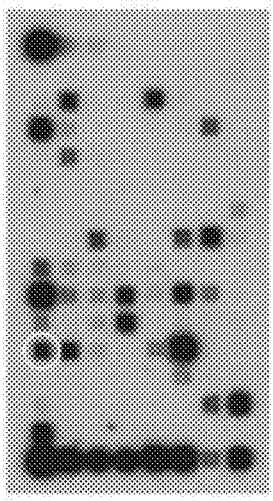
FIGS. 14A-14D depict arrays showing two up-regulated (≥2 fold), cancer related genes detected in macrophages from LLC1 (mouse metastatic lung cancer) tumor-bearing C57/Bl mice. (A) LLC1 tumor. (B) Macrophages obtained from C57/Bl mice bearing LLC1 tumors ($M_T$). (C) T cells obtained from C57/Bl mice bearing LLC1 tumors ($T_T$). (D) Macrophages obtained from non-tumor-bearing C57/Bl mice ($M_N$). Circled signatures expressed in tumor cells (A) and in neutrophils from tumor-bearing mice (B), and minimally expressed in neutrophils from non-tumor-bearing mice (D), and in non-phagocytic T cells (C). Expression in $M_T$ was ≥2-fold than that in $M_N$ and $T_T$.
Figure 14B:
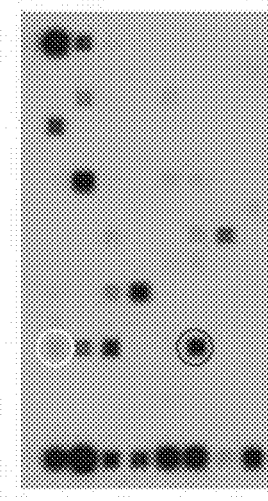
Figure 14C:
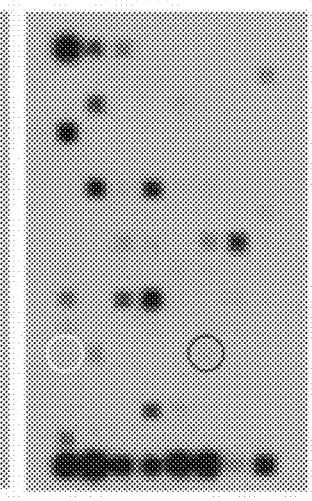
Figure 14D:
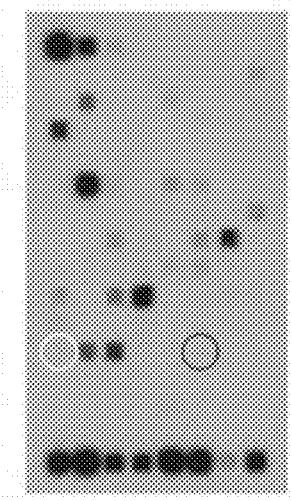
Figure 15A:
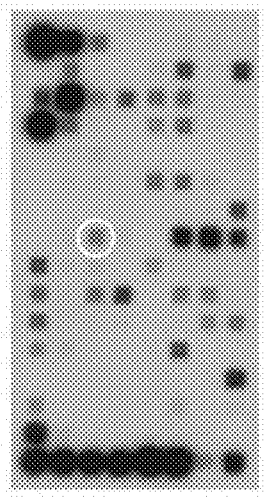
FIG. 15A-15D depict arrays showing two up-regulated (≥2 fold), cancer related genes detected in neutrophils from B16F10 (mouse metastatic melanoma) tumor bearing C57/Bl mice. (A) B16F10 tumor. (B) Neutrophils obtained from C57/Bl mice bearing B16F10 tumors ($N_T$). (C) T cells obtained from C57/Bl mice-bearing B16F10 tumors ($T_T$). (D) Neutrophils obtained from non-tumor-bearing C57/Bl mice ($N_N$). Circled signatures expressed in tumor cells (A) and in neutrophils from tumor-bearing mice (B), and minimally expressed in neutrophils from non-tumor-bearing mice (D), and in non-phagocytic T cells (C). Expression in $N_T$ was ≥2-fold than that in $N_N$ and $T_T$.
Figure 15B:
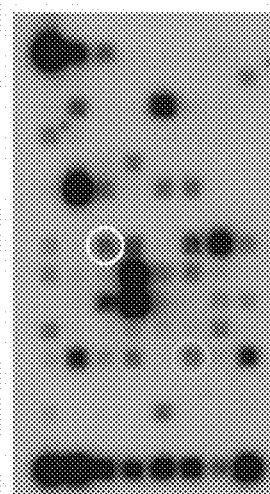
Figure 15C:
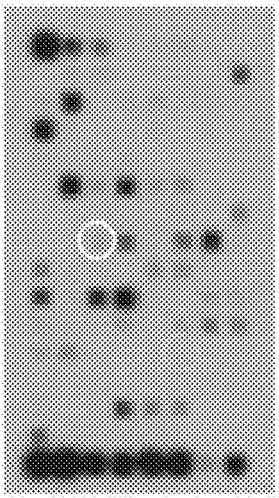
Figure 15D:
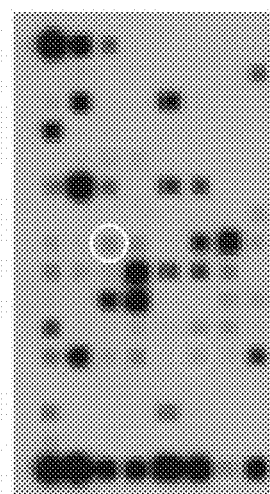
Figure 16A:
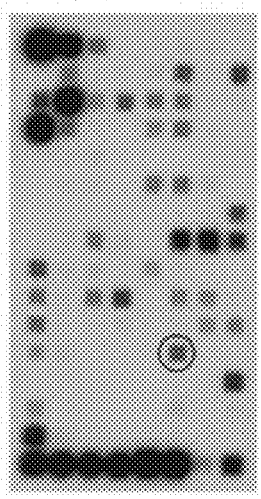
FIGS. 16A-16D depict arrays showing one up-regulated (≥2 fold), cancer related genes detected in macrophages from B16F10 (mouse metastatic melanoma) tumor-bearing C57/Bl mice. (A) B16F10 tumor. (B) Macrophages obtained from C57/Bl mice bearing B16F10 tumors ($M_T$). (C) T cells obtained from C57/Bl mice bearing B16F10 tumors ($T_T$). (D: Macrophages obtained from non-tumor-bearing C57/Bl mice ($M_N$). Circled signatures expressed in tumor cells (A) and in macrophages from tumor-bearing mice (B), and minimally expressed in macrophages from non-tumor-bearing mice (D), and in non-phagocytic T cells (C). Expression in $M_T$ was ≥2-fold than that in $M_N$ and $T_T$.
Figure 16B:
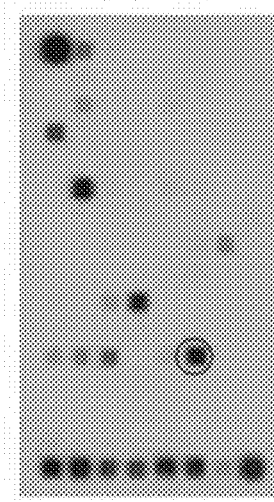
Figure 16C:
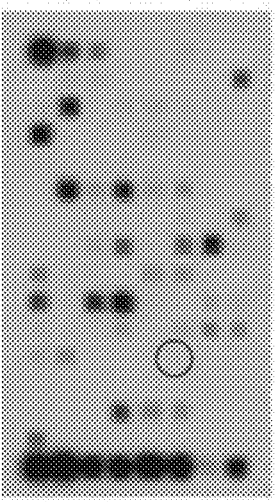
Figure 16D:
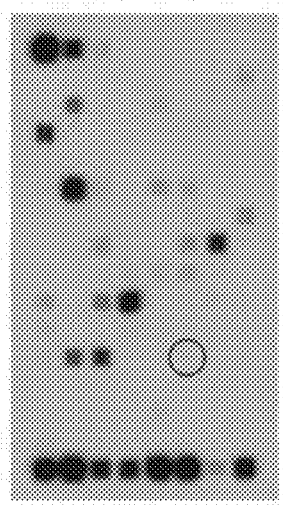
Figure 21:
FIG. 21 lists expression of cancer-related genes within phagocytic neutrophils (N) and macrophages (M).

These genes were either not expressed or minimally expressed in T cells obtained from tumor-bearing mice or neutrophils isolated from normal mice (see profiles shown in FIGS. 13C and 13D). Finally, the arrays were scanned, the intensity of each gene quantified using the software provided by the company, and those genes overexpressed selectively by phagocytic cells identified as shown in FIGS. 19 and 20. FIGS. 21 and 22 list the gene signatures acquired and differentially exhibited by the phagocytic WBCs of tumor-bearing mice. As shown in FIG. 21, many oncogenes (genes depicted in red, e.g., ERBB2 and Jun) were detected and often they were expressed simultaneously in macrophages and neutrophils.

C57Bl mice (n=5) were injected subcutaneously with 1E6 Lewis lung mouse carcinoma cells (LLCl). Twenty days later, the mice were anesthetized and bled by cardiac puncture (approximately 1 mL/mouse) into an EDTA-containing tube. Following centrifugation at 2,000 rpm for 5 minutes at room temperature, the buffy coat was transferred to a tube and washed with PBS.

Anti-mouse macrophage/monocyte rat IgG antibodies (monocyte/macrophage marker—F4/80—IgG2b from AbD Serotec, Raleigh, N.C.) were incubated (room temperature for 30 minutes) with anti-rat IgG antibody magnetic beads (DYNABEAD® sheep anti-rat IgG from INVITROGEN™, Carlsbad, Calif.). The anti-macrophage/monocyte beads were then washed in PBS and stored on ice.

Anti-mouse neutrophil rat IgG (Neutrophil Marker NIMP-R14—IgG2a—Santa Cruz Biotechnology, Santa Cruz, Calif.) was incubated (room temperature for 30 minutes) with anti-rat IgG antibody magnetic beads (DYNABEAD® sheep anti-rat IgG—INVITROGEN™), washed in PBS, and stored on ice.

DYNABEAD® mouse Pan T (Thy1.2) beads (INVITROGEN™) were also washed in PBS and stored on ice.

Mouse blood macrophages and monocytes were isolated from the WBC suspension prepared above using the anti-macrophage/monocyte beads. In essence, the beads were added to the WBC sample and following their incubation (4° C. for 30 minutes), the macrophage-bound beads were isolated using a magnet and washed with PBS three times and stored on ice.

Mouse T cells were then isolated from the remaining WBC. Briefly, the anti-mouse T cell beads were added to the WBC suspension, the samples incubated (4° C. for 30 minutes), the T cell-bound beads were isolated using a magnet, washed with PBS, and stored on ice.

Finally, mouse neutrophils were isolated from the remaining WBC sample. The anti-mouse neutrophil magnetic beads were added to the cells and the samples were incubated (4° C. for 30 minutes). The neutrophil-bound beads were isolated using a magnet, washed with PBS, and stored on ice.

Figure 7:
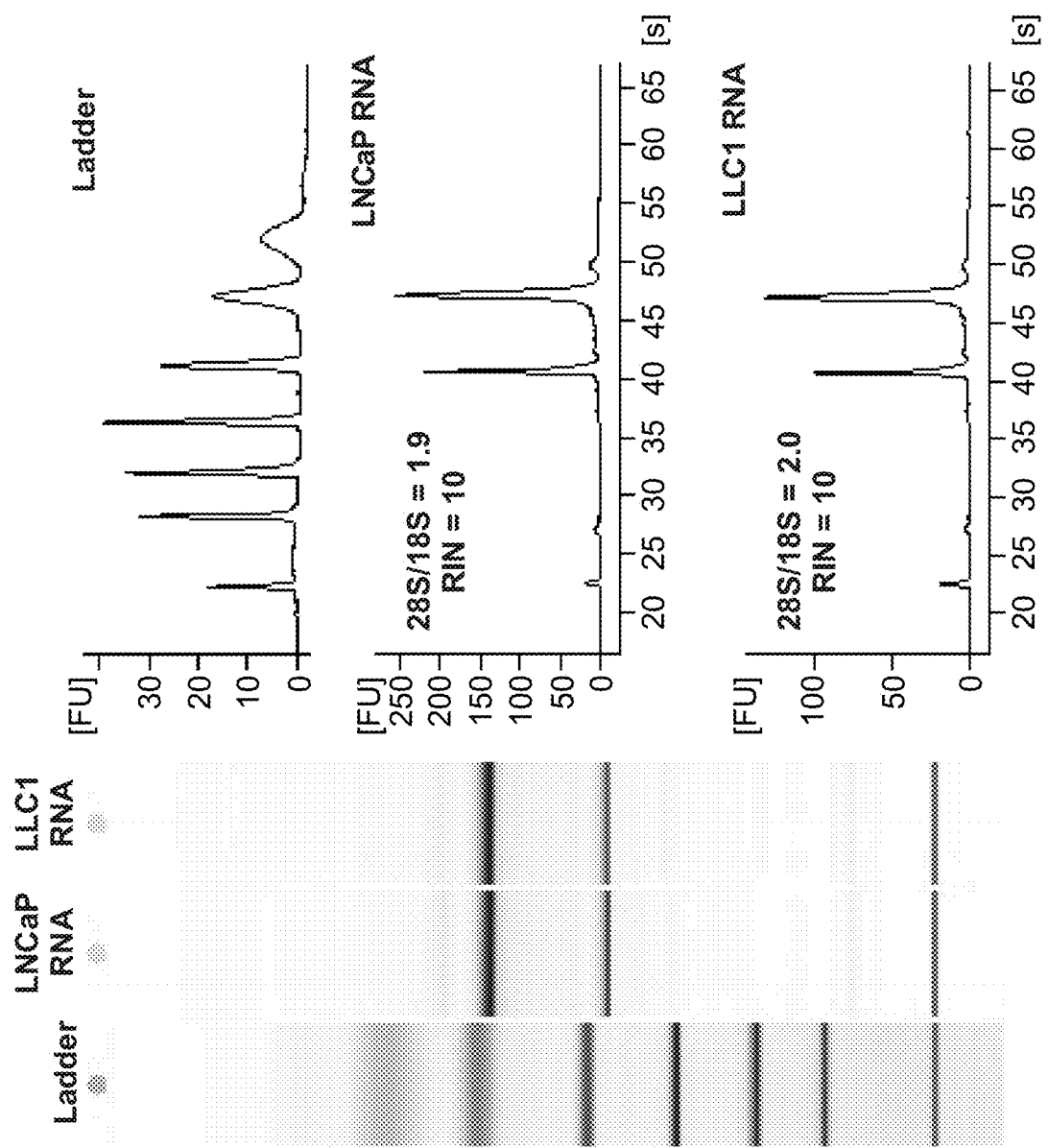
FIG. 7 depicts gel electrophoresis analysis of total RNA isolated from LNCaP and LLC1 cells.

RNA was then isolated from each sample (using TRIZOL®, INVITROGEN™, Carlsbad, Calif.). The RNA quality was determined as shown in FIG. 7. The RNA yield is shown in FIG. 8. Next, cDNA (biotinylated) were prepared and incubated (60° C. overnight) with cancer-gene human microarrays (OLIGO GEARRAY® Human Cancer PathwayFinder Microarray OMM-033, SuperArray Bioscience, Frederick, Md.). Following hybridization, the membranes were washed and stained with avidin-alkaline phosphatase and the genes detected using chemiluminescence (X-ray film).

Human LS175T Colon Adenocarcinoma Tumors, LLC1 Carcinoma and B16F10 Mouse Melanoma Cells Similar experiments were carried out with cells isolated from athymic nude mice (n=5) injected s.c. with human LS174T colon adenocarcinoma tumors (tumor size=~0.3 cm), C57/Bl mice (n=5) injected s.c. with Lewis lung mouse LLC1 carcinoma cells (tumor size=~0.6 cm), and C57Bl mice (n=5) injected intravenously 22 days earlier with $10^6$ B16F10 mouse melanoma cells (when the tumor cells were of mouse origin, the cRNA-B samples were hybridized with the Oligo GEARRAY® Mouse Cancer PathwayFinder Microarray—OMM-033—SuperArray Bioscience (when the tumors were of human origin, the Oligo GEArray® Human Cancer PathwayFinder Microarray—OHS-033— was used). RNA was also isolated from exponentially growing LS174T, LLC1, B16F10, and LNCaP cells in culture and from neutrophils, macrophages and T cells isolated from non-tumor-bearing C57Bl and nude mice, and their cancer-related gene profiles were determined.

According to the data obtained from these experiments and shown in FIGS. 9A-9D, 10A-10D, 11A-11D, 12A-12D, 13A-13D, 14A-14D, 15A-15D, 16A-16D, neutrophils and macrophages (obtained from mice injected with human prostate or colon tumor cells and from mice bearing mouse lung cancer or melanoma) had various cancer-related gene signatures that were also found in their respective tumor cells (FIG. 21). These cancer-related genes were not expressed or were minimally expressed by (i) non-phagocytic T cells isolated from tumor-bearing mice; and (ii) phagocytic neutrophils and macrophages obtained from non-tumor-bearing mice.

For example, neutrophils isolated from the blood of nude mice bearing LNCaP human prostate cancer cells expressed seven human tumor gene signatures (Human Cancer PathwayFinder Microarray) that were also expressed in LNCaP cells (compare profiles of arrays in FIGS. 9A and 9B). These genes were either not expressed or minimally expressed in T cells obtained from tumor-bearing mice or neutrophils isolated from normal mice (see profiles in FIGS. 9C and 9D). Finally, the arrays were scanned, the intensity of each gene quantified using the software provided by the company, and those genes overexpressed selectively by phagocytic cells identified as shown in FIGS. 19 and 20. FIGS. 21 and 22 list the gene signatures acquired and differentially exhibited by the phagocytic WBCs of tumor-bearing mice. As shown in FIG. 21, many oncogenes (e.g., ERBB2 and Jun) were detected and often they were expressed simultaneously in macrophages and neutrophils (shown by the genes highlighted in green).

EXAMPLE 8

Detection of Tumor-Specific Gene Signatures in Phagocytes Obtained from Cancer Patients According to certain embodiments of the present invention, the gene-expression profiles of blood monocytes/macrophages and neutrophils from cancer patients were compared with that of non-phagocytic T cells from the same donor individuals to identify tumor-specific signatures within the phagocytic cells that were either not expressed or significantly differentially expressed in non-phagocytic cells.

Patients with Head and Neck Tumors

Ten milliliters of venous blood was obtained (into an EDTA-containing tube) from patients known to have squamous cell carcinoma of the neck and scheduled for surgery. Following centrifugation at 2,000 rpm for 5 minutes at room temperature, the buffy coat was transferred to a tube and washed with PBS.

The cells were separated employing T cell-, neutrophil-, and macrophage/monocyte-rat anti-human immunomagnetic DynaBeads® from INVITROGEN™, Carlsbad, Calif. In essence, the beads were added consecutively to the WBC sample and following individual 4° C., 30 minute incubations, the T cells-, neutrophils-, and macrophages/monocytes-bound beads were isolated using a magnet and washed with PBS three times.

RNA was then isolated from each sample (using TRIZOL®, INVITROGEN™, Carlsbad, Calif.). The RNA quantity and quality was determined and cDNA and biotinylated cRNA (cRNA-B) were prepared. Finally, the cRNA-B samples were incubated (60° C. overnight) with cancer-gene human microarrays (Oligo GEArray® Human Cancer PathwayFinder Microarray—OHS-033—SuperArray Bioscience, Frederick, Md.). Following hybridization, the membranes were washed and stained with avidin-alkaline phosphatase, and the genes were detected using chemiluminescence (X-ray film).

According to the data obtained from these experiments, neutrophils and macrophages (obtained from head and neck cancer patients) had various cancer-related gene signatures that were also found in their respective tumor cells. These cancer-related genes were not expressed or were minimally expressed by non-phagocytic T cells.

Figure 17A:
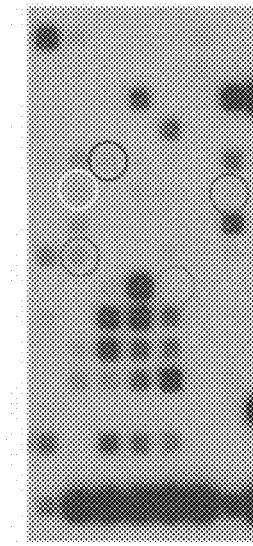
FIGS. 17A-17D depict arrays showing five up-regulated (≥2 fold), cancer related genes detected in neutrophils from patient with head and neck cancer (squamous cell carcinoma). (A) Normal tissue (skin) biopsy. (B) Tumor tissue biopsy. (C) Neutrophils obtained from patient blood ($N_T$). (D) T cells obtained from patient blood ($T_T$). Circled signatures expressed in tumor cells (B) and in neutrophils from patient blood (C), and minimally expressed or not expressed in normal skin (A) or non-phagocytic T cells (D). Expression in $N_T$ was ≥2-fold than that in $T_T$ and skin.
Figure 17B:
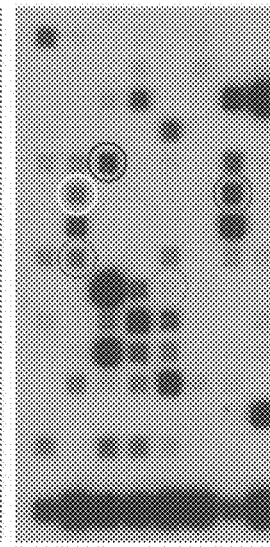
Figure 17C:
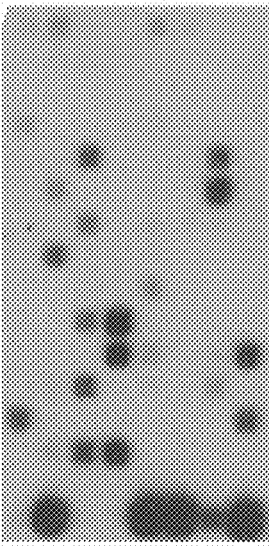
Figure 17D:
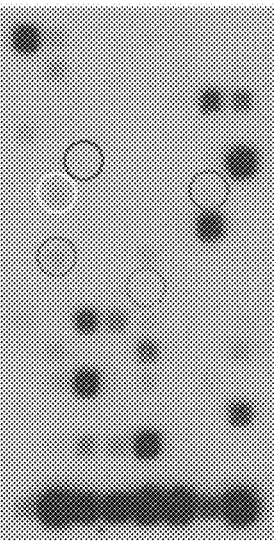
Figure 20A:
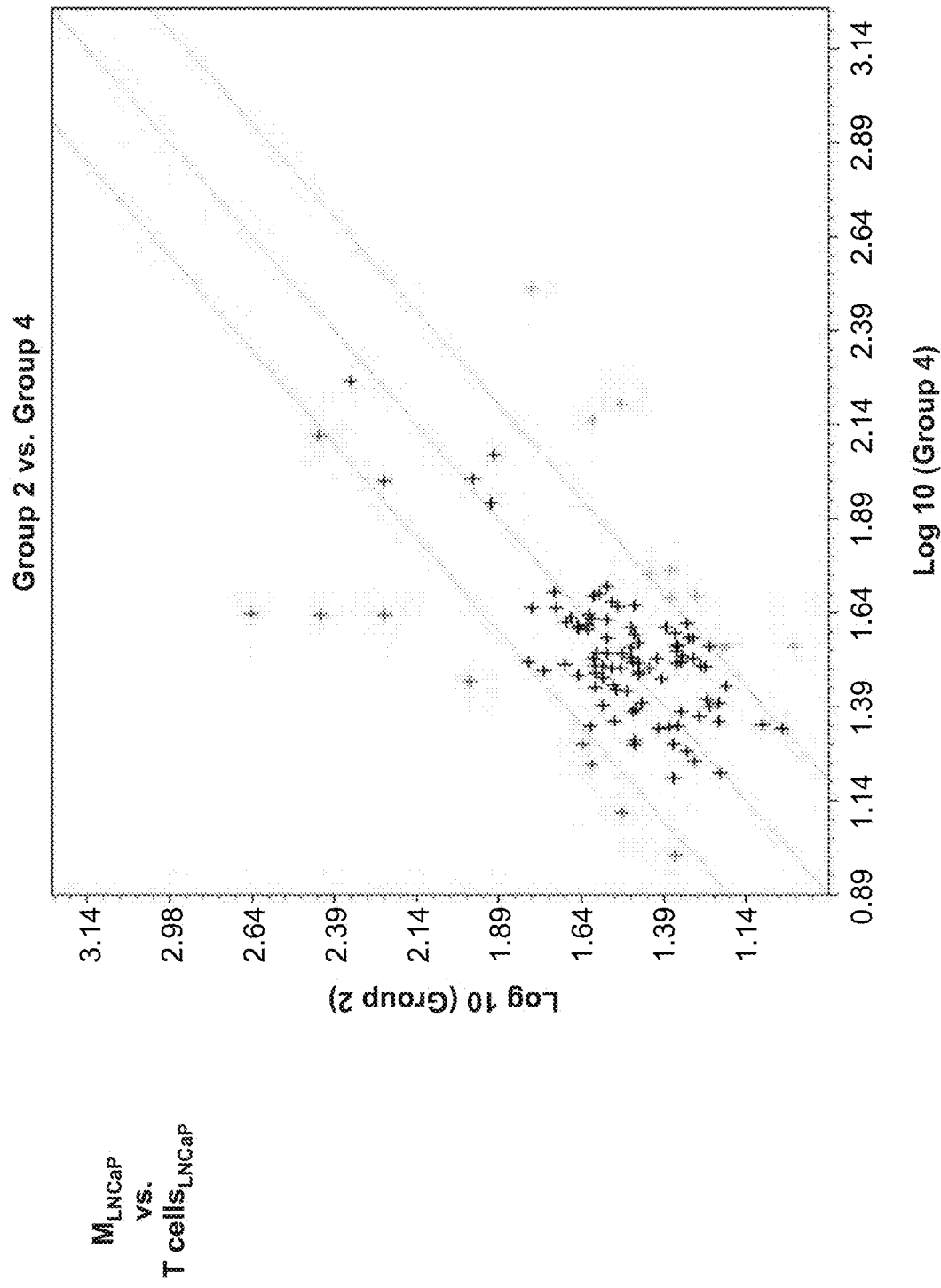
FIGS. 20A-20D depict gene expression intensity comparisons in (A) macrophages obtained from nude mice bearing LNCaP human prostate tumors ($M_{LNCaP}$) and T cells from the same animals (T cells$_{LNCaP}$), (B) $M_{LNCaP}$ and macrophages obtained from non-tumor-bearing mice ($M_{non-tumor}$), (C) neutrophils obtained from nude mice bearing LNCaP human prostate tumors ($N_{LNCaP}$) and T cells from the same animals (T cells$_{LNCaP}$), and (D) $N_{LNCaP}$ and macrophages obtained from non-tumor-bearing mice ($N_{non-tumor}$). Genes in red were overexpressed ≥2 fold; those in green were under-expressed ≥2 fold.
Figure 20B:
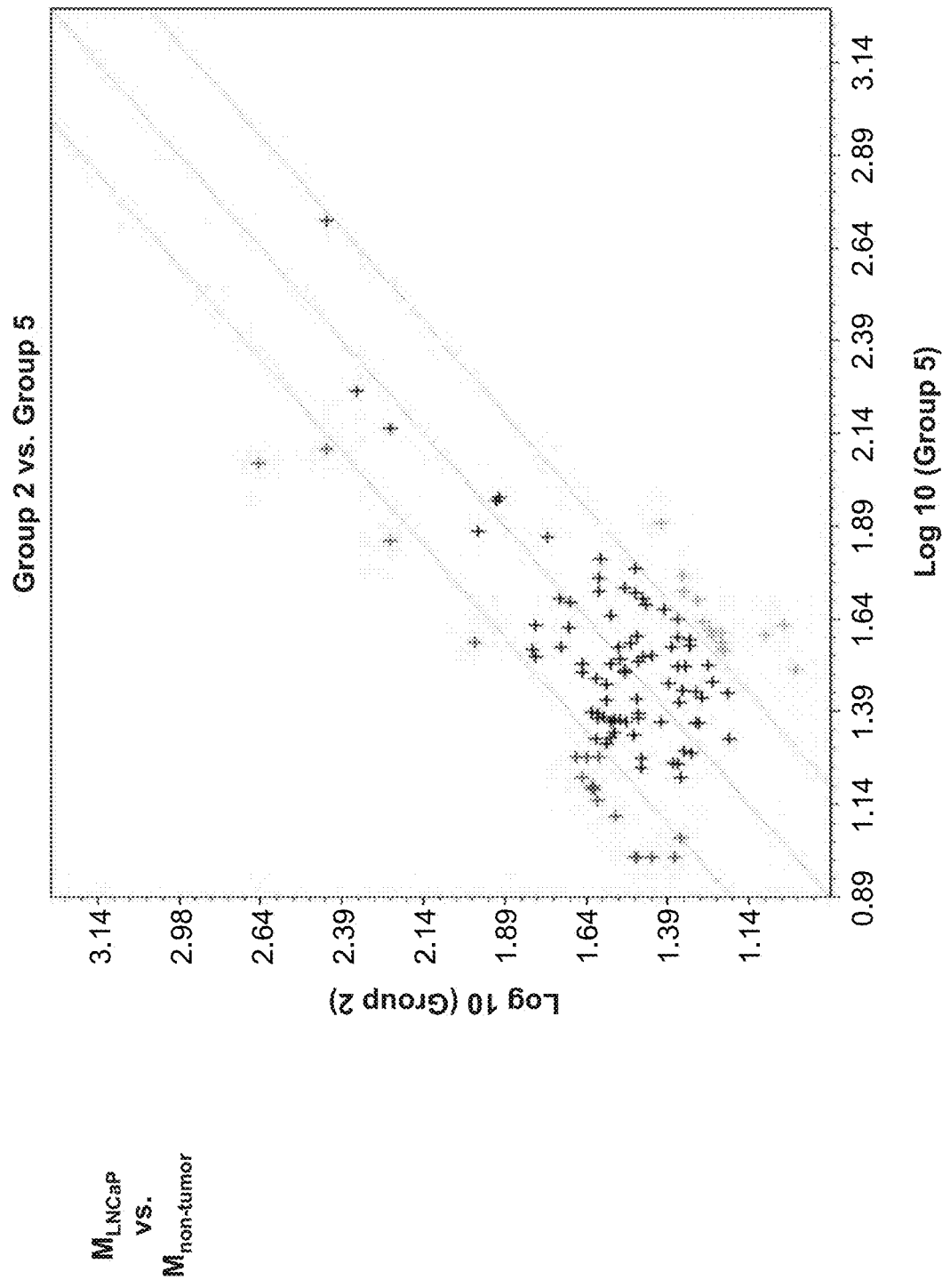
Figure 20C:
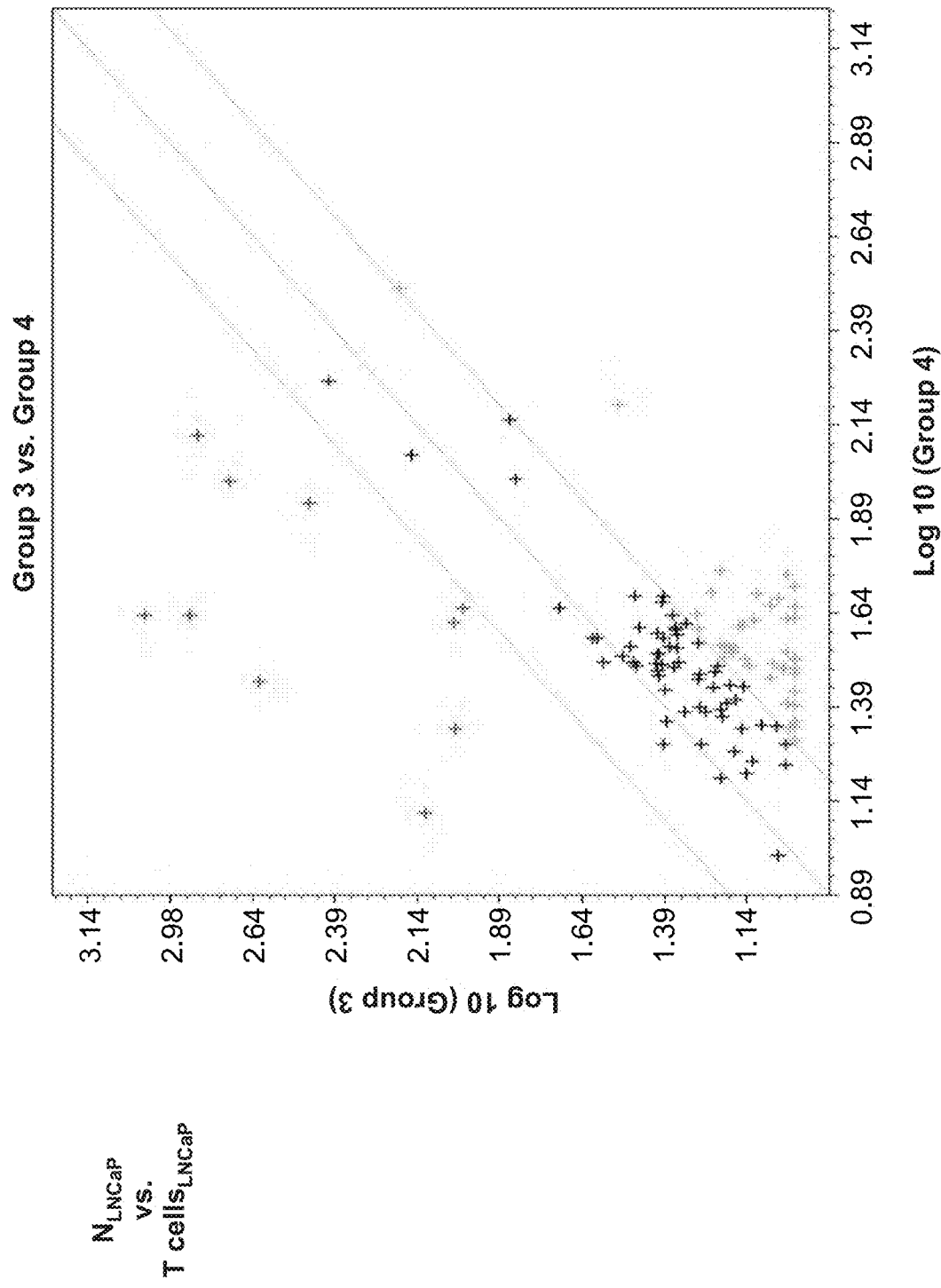
Figure 20D:
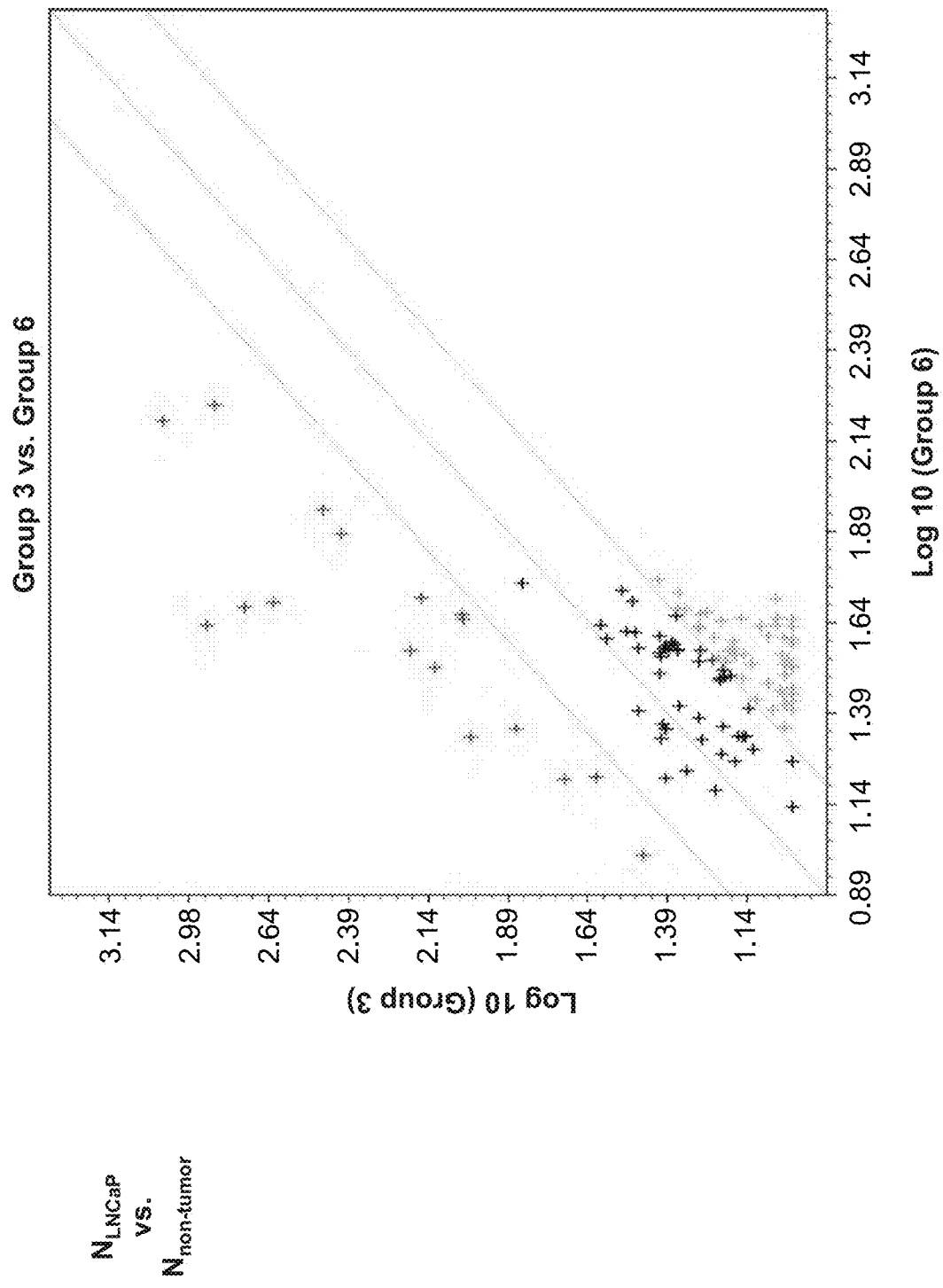

For example, neutrophils isolated from the blood of one such patient expressed four human tumor gene signatures (Human Cancer PathwayFinder Microarray) that were also expressed in the tumor biopsy obtained from the same patient (compare profiles of arrays in FIGS. 17B and 17C). These genes were either not expressed or minimally expressed in normal skin biopsy and in T cells isolated from the same blood sample (see profiles in FIGS. 17A and 17D, respectively). Finally, the arrays were scanned, the intensity of each gene quantified using the software provided by the company, and the following genes that were overexpressed (>2-fold) selectively by phagocytic cells were identified: E26 viral oncogene homolog (ETS2), HIV-1 Tat interactive protein (HTAT1P2), IL8 (neutrophil activation and chemotaxis), Jun oncogene (JUN), and matrix metalloproteinase 9 (MMP9).

Ovarian Cancer Patients

Similar experiments were carried out with cells isolated from a patient with ovarian cancer. According to the data obtained from these experiments, neutrophils and macrophages (obtained from the diseased woman) expressed many cancer-related genes that were not expressed or were minimally expressed by non-phagocytic T cells.

For example, macrophages isolated from the blood of the ovarian cancer patient expressed 23 human tumor gene signatures (Human Cancer PathwayFinder Microarray) that were either not expressed or minimally expressed in T cells isolated from the same blood sample (compare profiles in FIGS. 18A and 18B). Finally, the arrays were scanned, the intensity of each gene quantified using the software provided by the company, and the intensities of each cancer-related gene in each cell type determined. The list of 23 cancer-related genes differentially upregulated/overexpressed in macrophages as well as the macrophage-to-T cell intensity ratios are both shown in FIG. 22. Note that a total of five oncogenes were detected (shown in red in FIG. 21).

EXAMPLE 9

Figure 23:
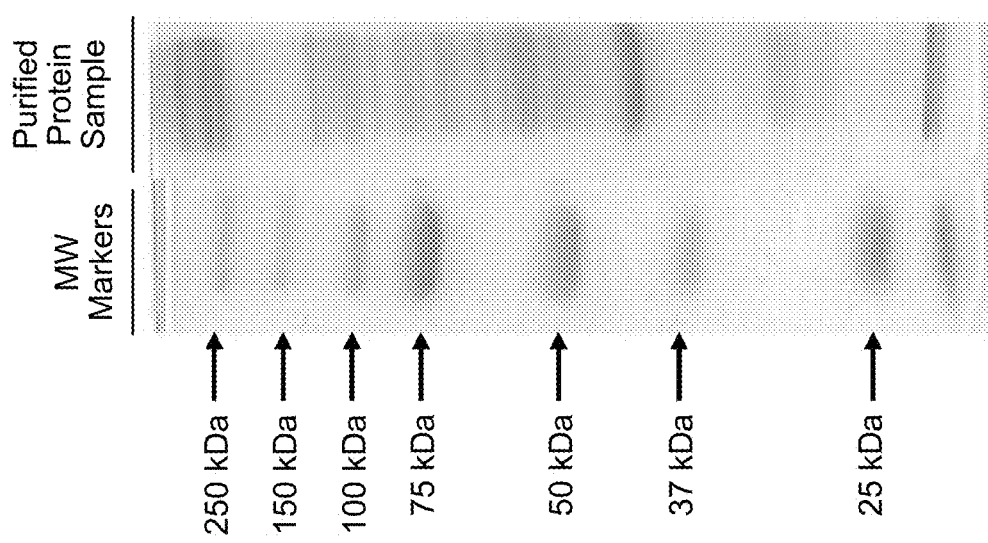
FIG. 23 depicts SDS gel (10%) electrophoresis of protein sample (5.9 µg) obtained from mouse WBC.

Detection of Tumor-Specific Protein Signatures in Phagocytes Obtained from Mice Bearing Human Prostate LNCaP Tumors and Human Colon LS174T Tumors A protein purification kit (Norgen, Incorporated, Product #23500) was used to isolate and purify proteins from mouse WBCs, T cells, and macrophages. The assay was very simple and fast (approximately 30 minutes) and the isolated proteins, which were of high quality and excellent yield (117.6±10.60 µg per 4 mL blood, n=5), could be used in a number of downstream applications, such as SDS-PAGE analysis as shown in FIG. 23 and Western blots.

Protein samples were isolated from phagocytic (monocytes/macrophages) and non-phagocytic (T-lymphocytes) cells obtained from mice bearing LNCaP and LS174T tumors were selected for these studies since the former cell line expresses PSA (Denmeade et al. (2001) *Prostate* 48:1; Lin et al. (2001) *J. Urol.* 166:1943) and the latter exhibits a tumor-specific glycoprotein (TAG-72), a high molecular weight mucin (Colcher et al. (1981) *Proc. Natl. Acad. Sci. USA* 78:3199); Colcher et al. (1984) *Cancer Res.* 44:5744; Kassis et al. (1996) *J. Nucl. Med.* 37:343. Western blot analysis was carried out with 16 µg of the purified protein samples. In essence, each sample was mixed with two volumes of SDS loading buffer and run on 10% SDS-PAGE along with unstained precision plus protein standards (Biorad) in Tris-glycine-SDS buffer (pH 8.4) at 200 volts. The proteins were transferred to a nitrocellulose membrane (overnight at 4° C.) using a Mini Trans-Blot (Biorad) apparatus and a transfer buffer containing 25 mM Tris, pH 8.4, 192 mM glycine, and 20% methanol. The membrane was blocked with 5% nonfat dry milk (60 min at room temperature (RT)) and incubated (1 hour, RT) with either B72.3, a mouse monoclonal antibody against human TAG-72, or ER-PR8, a mouse monoclonal antibody against human PSA. The blots were washed and then incubated with Immun-Star Goat Anti Mouse—HRP conjugate (Biorad), a secondary antibody specific to mouse IgG, and developed by incubation (5 min, RT) with a 1:1 mixture of luminol solution and peroxide buffer (Biorad), followed by autoradiography.

Figure 24:
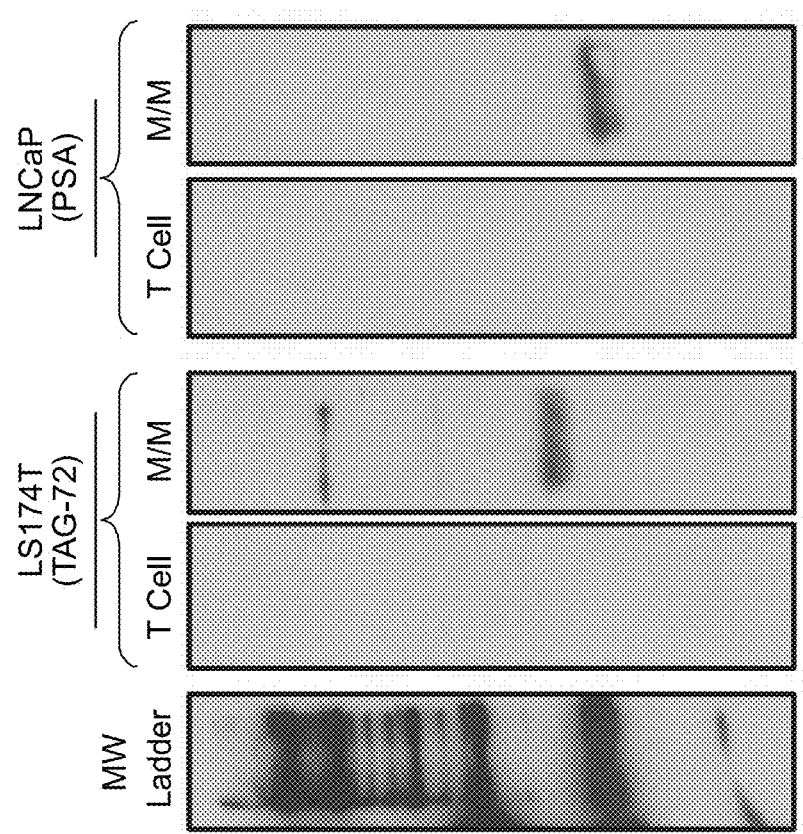
FIG. 24 depicts Western blot analysis of TAG-72 and PSA expression in T cells and monocytes/macrophages (M/M) obtained from tumor-bearing mice, illustrating the presence of signatures in phagocytic cells only.

The data clearly indicated that phagocytic cells from LNCaP tumor-bearing mice were positive for PSA, whereas this protein could not be detected in non-phagocytic T cells from the same animals as shown in FIG. 24. Similarly, TAG-72 was expressed by monocytes/macrophages obtained from LS174T tumor-bearing mice and was completely absent in T cells from the same animals. These findings demonstrate the "acquisition" and expression of tumor-specific protein signatures by phagocytic cells.

While these data are specific to animals with cancer and phagocytic and non-phagocytic cells obtained from the blood of mice, the described methods are also useful in humans and in the diagnosis and/or detection of one or more other disorders and/or diseases and with phagocytic and non-phagocytic cells obtained from other bodily fluids.

EXAMPLE 10

Profiling Experiments

Isolation of Blood Phagocytic Cells

A sample of blood is obtained from a patient. The blood (~5 mL) will be transferred to a 50-mL tube containing 50 µL, 0.5 M EDTA (final EDTA concentration=~4.8 mM). The tube will be vortexed gently and 25 mL RBC Lysis Buffer (Norgen, Incorporated) will be added. The tube will be vortexed gently again, incubated at room temperature until the color of the solution changes to bright red (3-5 min), and centrifuged at 2,000 rpm for 3 min. Following careful aspiration of the supernatant, the WBCs will be washed with 40 mL Ca/Mg-free 0.1 M PBS (containing 2% FBS, 2 mM EDTA, and 20 mM glucose), and the cells ($10^6$/mL) will then be incubated (30 min, 4° C., in the dark) with a cell-staining solution containing (i) the DNA, viable cell-permeable stain Hoechst 33342 (4 µg/mL; Em=483 nm), (ii) the anti-human monocytes/macrophages monoclonal antibody (Alexa Fluor® 647-conjugate; Em=668 nm), which recognizes the human F4/80 antigen expressed by circulating monocytes/macrophages, and (iii) the anti-human neutrophil monoclonal antibody (RPE-conjugate; Em=578 nm), which recognizes human circulating neutrophils. The cells will then be washed and sorted (BD FACSAria) into neutrophils ($N_{n=2}$), neutrophils ($N_{n>2}$), monocytes/macrophages ($M/M_{n=2}$), and monocytes/macrophages ($M/M_{n>2}$).

Gene Profiling

Human whole-genome gene profiling will be performed. For RNA samples obtained from human tumor cells or neutrophils ($N_{n=2}$, $N_{n>2}$) and monocytes/macrophages ($M/M_{n=2}$, $M/M_{n>2}$), the GeneChip® Human Genome U133 Plus 2.0 Array by Affymetrix, Incorporated will be used. This array analyzes the expression level of over 47,000 transcripts and variants, including 38,500 well-characterized human genes. In general, the extracted RNA will be used to determine the expression profiles of human genes using the above-mentioned array. To ensure array reproducibility, each sample will be profiled in triplicate and the experiment repeated once. The microarray data will be filtered for cancer-induction-related genes as described below and validated using quantitative real-time, reverse transcriptase, polymerase chain reaction (RT-PCR).

Upregulation/Downregulation of Cancer-Induction-Related Genes

RNA will be isolated using Triazol (Invitrogen, Incorporated) and purified using the cartridges provided in the kit. The RNA quality and quantity will be assessed with the Bioanalyzer 2100 (Agilent Technologies, Incorporated, Palo Alto, Calif.) and Degradometer software version 1.41 (Worldwide Web: dnaarrays.org). These experimental results will help in distinguishing the molecular pathways perturbed consequent to the presence of tumors.

Analysis of Microarray Experiments

The analysis of the large scale/high throughput molecular expression data generated will rely heavily on the ability to (i) identify genes differentially expressed in phagocytic cells with a DNA content >2, (ii) annotate the identified genes, and (iii) assign the annotated genes to those specifically expressed by a specific tumors. Statistical analysis of the microarray data can be done, for example, using the dChip package which easily accommodates this type of gene list construction in its "Analysis/Compare Samples" menu. When using Affymetrix GeneChips, one or more Gene Chips and associated methods will be applied to ascertain the quality of the raw microarray data (Gautier et al. (2004) *Bioinformatics* 20:307). Furthermore, various background correction and normalization procedures will be utilized to arrive at an optimal protocol for normalization and summarization of the probe sets (to produce expression values) (Huber et al. (2002) *Bioinformatics* 18 (Suppl. 1): S96; Wu et al. (2004) *Journal of the American Statistical Association* 99:909; Seo and Hoffman (2006) *BioMed Central Bioinformatics* 7:395). In a two-step filtration approach, we will compare the gene profiles of $P_{n=2}$ to those of $P_{n>2}$ and construct a list of expressed genes and then compare these genes to the tumor-specific genes identified for each tumor cell line—post filtration of $P_{n=2}$ gene profile as shown in FIG. 5. For example, (i) blood will be obtained from breast cancer patients; (ii) neutrophils (n>2 and n=2) will be isolated and their gene profiles determined in triplicate; (iii) the mean (from the 3 samples) of each identified gene and its respective standard error (SE) will be calculated for each group ($N_{n>2}$ and $N_{n=2}$); (iv) the gene expression profiles of the two groups will then be compared and a list (L-1) of expressed genes identified on the basis of an absolute ≥2-fold log change ($N_{n>2}/N_{n=2}$), according to the Welch modified two-sample t-test; (v) the gene expression profiles of $N_{n=2}$ and that of breast cancer (obtained from tumor and normal breast tissue biopsies) will be compared and a list (L-2) of expressed genes identified; and (vi) breast-cancer-specific gene signatures that have been acquired/expressed by $N_{n>2}$ will be identified by comparing the genes in L-1 and L-2 ("Analysis/Compare Samples/Combine Comparisons," dChip) and filtering common genes.

Protein Profiling

Fifty to one hundred micrograms of the total protein from each type of cells will be denatured and reduced with tris-(2-carboxyethyl)phosphinetrypsin (1 mM) and 0.02% sodium dodecyl sulfate at 60° C. for 1 hour. Cysteines are subsequently blocked and total protein is digested with trypsin at 37° C. for 12-16 hours. The resulting peptides will be iTRAQ-labeled (with tags 113-119 and 121) for 1 hour (4-plex or 8-plex depending on the number of cell types to be compared). Following labeling, the separately tagged samples are combined and injected into an Agilent 1200 Series HPLC system equipped with a strong cation exchange column (Applied Biosystems 4.6×100 Porous). The 96 collected fractions are then pooled into 14 fractions, and each fraction is injected into the LC Packings Ultimate HPLC System for a second round of fractionation under reverse-phase conditions (LC Packings 15 cm×75 µm analytical column). The reverse-phase fractions are spotted directly onto the target plate using an LC Packings Probot and are analyzed with mass spectrometry (Applied Biosystems 4800 Plus Proteomics Analyzer). Following data acquisition, the spectra are processed using the ProteinPilot software package (Applied Biosystems MDS Sciex), and the individual proteins in each of the cell types with their relative expression levels are identified using the ProteinPilot™ software (the analysis and identification of cancer-associated proteomic signatures will be similar to that outlined in FIG. 5 for the genomic signatures).

What is claimed is:

1. A method for measuring gene expression in a hematopoietic cell comprising the steps of:
    isolating by fluorescence activated cell sorting or by using antibodies at least one hematopoietic phagocytic cell and at least one hematopoietic non-phagocytic cell from a sample selected from the group consisting of whole blood, urine, stool, saliva, lymph, and cerebrospinal fluid from an individual having cancer;
    measuring a first expression profile for only two to 14 markers selected from the group consisting of BAK1, EGFR, ERBB2, FOS, JUN, MAP2K1, Mdm2, MMP2, PDGFB, Plaur, RB1, SNCG, SERPINB2, and SPP1 and/or only two to 23 markers selected from the group consisting of AKT1, APAF1, ATM, CDC25A, CDKN1A, ETS2, FOS, IL8, ITGA4, ITGA6, ITGAV, JUN, MAP2K1, NFKBIA, PLAU, PLAUR, RAF1, SERPINB2, SYK, TIMP1, TNF, TNFRSF10B, and TNFRSF1A from a hematopoietic phagocytic cell using a method selected from the group consisting of an amplification assay, a hybridization assay, and a microarray assay from said individual having cancer; and
    measuring a second expression profile of only said markers from a hematopoietic non-phagocytic cell using a method selected from the group consisting of an amplification assay, a hybridization assay, and a microarray assay from the individual having cancer.

2. The method of claim 1, wherein the hematopoietic phagocytic cell and the hematopoietic non-phagocytic cell are isolated using an antibody that binds to a molecular receptor expressed on the plasma membranes of white blood cell populations.

3. The method of claim 1, wherein the hematopoietic phagocytic cell and the hematopoietic non-phagocytic cell are isolated from a population of white blood cells.

4. The method of claim 3, wherein the hematopoietic phagocytic cell and the hematopoietic non-phagocytic cell are separated using an antibody that binds to molecular receptors expressed on the plasma membranes of white blood cell populations.

5. The method of claim 1, wherein the phagocytic cell is a macrophage.

6. The method of claim 1, wherein the phagocytic cell is a neutrophil.

7. The method of claim 1, wherein the phagocytic cell is selected from the group consisting of a neutrophil, a macrophage, a monocyte, a dendritic cell and a foam cell.

8. The method of claim 1, wherein the non-phagocytic cell is selected from the group consisting of a T cell, a B cell, a null cell and a basophil.

9. The method of claim 1, wherein the two or more markers are RNA.

10. The method of claim 1, wherein the two or more markers are selected from the group consisting of RNA, cDNA, and combinations thereof.

\* \* \* \* \*